United States Patent [19]

Baba et al.

[11] Patent Number: 5,094,685

[45] Date of Patent: Mar. 10, 1992

[54] SUBSTITUTED BENZOYL DERIVATIVES AND SELECTIVE HERBICIDES

[75] Inventors: Masatoshi Baba; Takuya Kakuta; Norio Tanaka; Eiichi Oya, all of Funabashi; Takashi Ikai, Tokyo; Tsutomu Nawamaki, Shiraoka; Shigeomi Watanabe, Shiraoka; Koichi Suzuki, Shiraoka, all of Japan

[73] Assignee: Nissan Chemical Industries Ltd., Tokyo, Japan

[21] Appl. No.: 538,089

[22] Filed: Jun. 13, 1990

Related U.S. Application Data

[62] Division of Ser. No. 259,587, Oct. 18, 1988, Pat. No. 4,954,165.

[30] Foreign Application Priority Data

Oct. 19, 1987 [JP] Japan .................. 62-263060
Nov. 20, 1987 [JP] Japan .................. 62-293804

[51] Int. Cl.$^5$ ...................... A01N 35/02; C07C 317/06
[52] U.S. Cl. .......................................... 71/103; 71/98; 568/31; 568/37
[58] Field of Search ................ 568/31, 37; 71/98, 103

[56] References Cited

U.S. PATENT DOCUMENTS 4,957,538 9/1990 Michaely .................. 568/31

Primary Examiner—Johann Richter
Attorney, Agent, or Firm—Oblon, Spivak, McClelland, Maier & Neustadt

[57] ABSTRACT

A substituted benzoyl derivative having the formula:

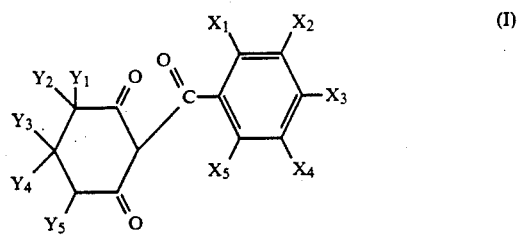

wherein $X_1$ is $C_1$-$C_4$ alkyl, $C_2$-$C_5$ alkoxyalkyl, $C_1$-$C_4$ haloalkyl, $C_1$-$C_4$ alkoxy, $C_1$-$C_4$ haloalkoxy, cyano, nitro or halogen; $X_2$ is —L—$OR_1$ (wherein L is $C_1$-$C_4$ alkylene or $C_1$-$C_4$ alkylidene, and $R_1$ is hydrogen, $C_1$-$C_4$ alkyl, $C_1$-$C_4$ alkenyl or $C_1$-$C_4$ alkynyl), —L—O—L—$OR_1$ (wherein L and $R_1$ are as defined above), —L—$S(O)_n$—$R_2$ (wherein L is as defined above, $R_2$ is $C_1$-$C_4$ alkyl, $C_1$-$C_4$ alkenyl or $C_1$-$C_4$ alkynyl, and n is an integer of 0, 1 or 2), —L—O—$COR_2$ (wherein L and $R_2$ are as defined above), —L—$NR_1R_3$ (wherein L and $R_1$ are as defined above, and $R_3$ is hydrogen or $C_1$-$C_4$ alkyl), —$COOR_1$ (wherein $R_1$ is as defined above) or —COO—L—O—$R_1$ (wherein L and $R_1$ are as defined above), provided that when $X_1$ is $C_1$-$C_4$ alkyl or $C_1$-$C_4$ haloalkyl, $X_2$ is not —$COOR_1$; $X_3$ is trifluoromethyl, $C_1$-$C_3$ alkoxy, halogen, cyano, nitro or —$S(O)_nR_4$ (wherein n is as defined above, and $R_4$ is $C_1C_3$ alkyl); $X_4$ is hydrogen, $C_1$-$C_4$ alkyl, $C_1$-$C_4$ alkoxy or halogen; $X_5$ is hydrogen or fluorine; and each of $Y_1$, $Y_2$, $Y_3$, $Y_4$ and $Y_5$ is hydrogen or $C_1$-$C_4$ alkyl; or a salt thereof.

5 Claims, No Drawings

SUBSTITUTED BENZOYL DERIVATIVES AND SELECTIVE HERBICIDES

This is a continuation of application Ser. No. 07/259,587, filed on Oct. 18, 1988, now U.S. Pat. No. 4,954,165.

BACKGROUND OF THE INVENTION

1. Field of the Invention

The present invention relates to novel substituted benzoyl derivatives and selective herbicides containing such derivatives as active ingredients.

2. Discussion of Background

Various herbicides have been developed for practical use from extensive research and development of herbicides for many years, and such herbicides have contributed to a reduction of the labor force required for controlling weeds or to improvement of the productivity of agricultural or horticultural plants.

Even now, it is still desired to develop a new herbicide having superior herbicidal properties. In particular, it is desired to develop an agricultural or horticultural herbicide which is capable of selectively controlling weeds without adversely affecting the crop plant and at a low dose. However, conventional herbicides do not necessarily provide such desired herbicidal properties.

On the other hand, among substituted benzoyl derivatives, certain compounds of 4-benzoylpyrazole derivatives are known to have herbicidal activities. For example, pyrazolate (common name) and pyrazoxyfen (common name) are practically used as herbicides for paddy fields. While exhibiting excellent herbicidal activities as paddy field herbicides, these compounds are not suitable as upland herbicides since their herbicidal activities are weak against weeds of upland fields. Among substituted benzoyl derivatives, it is desired to develop a superior compound useful as an upland field herbicide.

SUMMARY OF THE INVENTION

The present invention provides a substituted benzoyl derivative having the formula:

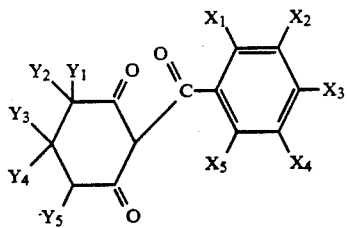

wherein $X_1$ is $C_1$–$C_4$ alkyl, $C_2$–$C_5$ alkoxyalkyl, $C_1$–$C_4$ haloalkyl, $C_1$–$C_4$ alkoxy, $C_1$–$C_4$ haloalkoxy, cyano, nitro or halogen; $X_2$ is —L—$OR_1$ (wherein L is $C_1$–$C_4$ alkylene or $C_1$–$C_4$ alkylidene, and $R_1$ is hydrogen, $C_1$–$C_4$ alkyl, $C_1$–$C_4$ alkenyl or $C_1$–$C_4$ alkynyl), —L—O—L—$OR_1$ (wherein L and $R_1$ are as defined above), —L—$S(O)_n$—$R_2$ (wherein L is as defined above, $R_2$ is $C_1$–$C_4$ alkyl, $C_1$–$C_4$ alkenyl or $C_1$–$C_4$ alkynyl, and n is an integer of 0, 1 or 2), —L—O—$COR_2$ (wherein L and $R_2$ are as defined above), —L—$NR_1R_3$ (wherein L and $R_1$ are as defined above, and $R_3$ is hydrogen or $C_1$–$C_4$ alkyl), —$COOR_1$ (wherein $R_1$ is as defined above) or —COO—L—O—$R_1$ (wherein L and $R_1$ are as defined above), provided that when $X_1$ is $C_1$–$C_4$ alkyl or $C_1$–$C_4$ haloalkyl, $X_2$ is not —$COOR_1$; $X_3$ is trifluoromethyl, $C_1$–$C_3$ alkoxy, halogen, cyano, nitro or —$S(O)_nR_4$ (wherein n is as defined above, and $R_4$ is $C_1$–$C_3$ alkyl); $X_4$ is hydrogen, $C_1$–$C_4$ alkyl, $C_1$–$C_4$ alkoxy or halogen; $X_5$ is hydrogen or fluorine; and each of $Y_1$, $Y_2$, $Y_3$, $Y_4$ and $Y_5$ is hydrogen or $C_1$–$C_4$ alkyl; or a salt thereof.

The present invention also provides a selective herbicide comprising a herbicidally effective amount of at least one substituted benzoyl derivative of the formula I as defined above or its salt and an agricultural carrier or diluent.

As a result of extensive researches for many years, the present inventors have found that the compounds of the formula I of the present invention have herbicidal activities substantially higher than the conventional herbicides. Further, many compounds of the present invention have superior selectivity for certain crop plants such as corn, wheat, rice and rapeseed, and they are thus practically very useful. The present invention is based on these discoveries.

With the compounds of the present invention, the dose of the active ingredient per unit area can be substantially reduced as compared with the conventional compounds, and the phytotoxicity against crop plants is extremely low as compared with the conventional herbicides. The economical merits are thus substantial. Further, with the compounds of the present invention, it is possible to substantially reduce a danger of environmental pollution by the use of a large amount of agricultural drug, and an influence over other crop plants due to the persistent effect in soil is minimum. Therefore, the compounds of the present invention can be regarded as epoch-making herbicides. A feature of the compounds of the present invention is that the benzoyl moiety is substituted by substituents selected from the group consisting of $X_1$, $X_2$, $X_3$, $X_4$ and $X_5$ as defined above.

Heretofore, it has been known that 2-benzoylcyclohexane-1,3-dione derivatives have herbicidal activities, as disclosed, for example, in Japanese Unexamined Patent Publications No. 180451/1983, No. 87238/1985 and No. 155347/1986. However, compounds having such a specific combination of substituents as defined in the present invention have not been known. Moreover, the present inventors have found that by introducing such a combination of substituents as defined in the present invention to the benzoyl moiety, the herbicidal effects and the selectivity for crop plants of the substituted benzoyl derivatives can be remarkably improved.

DETAILED DESCRIPTION OF THE PREFERRED EMBODIMENTS

The compounds of the present invention can readily be prepared by using one of the reactions represented by the following reaction schemes.

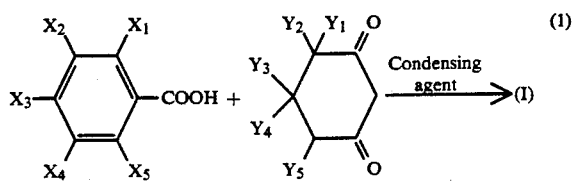

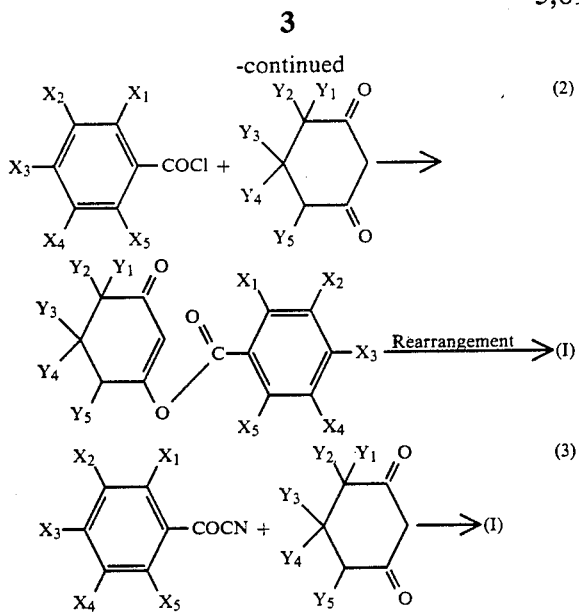

In the above formulas, $X_1$, $X_2$, $X_3$, $X_4$, $X_5$, $Y_1$, $Y_2$, $Y_3$, $Y_4$ and $Y_5$ are as defined above.

Further, the compounds of the present invention may be represented by the following four tautomer structures:

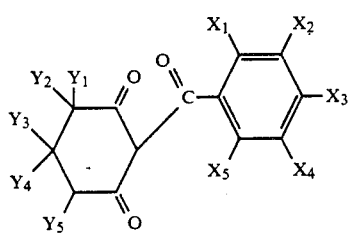

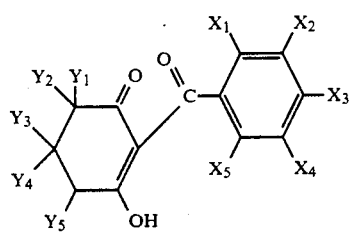

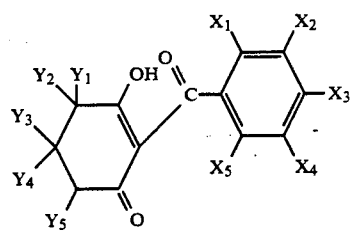

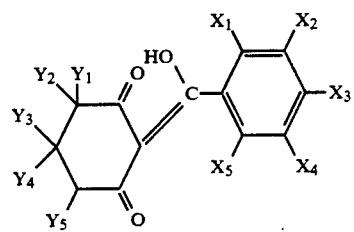

Reaction scheme (1) represents a reaction wherein a benzoic acid having appropriate substituents and a cyclohexane-1,3-dione are reacted in an inert solvent in the presence of a condensing agent and a base to obtain a 2-benzoylcylohexane derivative. As the condensing agent, for example, N,N'-dicyclohexylcarbodiimide may be mentioned. The condensing agent is used preferably in an amount of from 1.0 to 1.5 mols per mol of the benzoic acid and pyrazole. The solvent may be any solvent so long as it is inert to the reaction. Particularly preferred are tert-butyl alcohol, tert-amyl alcohol, and isopropyl alcohol. The base is not necessarily required. However, the yield is usually improved by using the base. There is no particular restriction as to the base, but potassium carbonate or sodium carbonate is preferred. The reaction temperature may range from room temperature to the boiling point of the solvent, and is preferably within a range of from 50° to 100° C. The reaction time is usually from 0.5 to 20 hours.

Reaction scheme (2) represents a reaction wherein a benzoyl chloride having appropriate substituents and a substituted cyclohexane-1,3-dione are reacted to form a benzoyl ester, which is then rearranged to obtain a 2-benzoyl compound.

The benzoyl esterification can be conducted in a solvent inert to the reaction (such as an aromatic hydrocarbon, an aliphatic ester, a halogenated hydrocarbon, an ether, acetonitrile, dimethylsulfoxide or N,N'-dimethylformamide) or in a two phase system or mixture thereof with water in the presence of a suitable dehydrochlorinating agent (e.g. an inorganic base such as sodium hydroxide, potassium hydroxide, sodium hydrogencarbonate or sodium phosphate, or an organic base such as pyridine or triethylamine) at a temperature of from 0° to 100° C. usually for 10 minutes to 5 hours.

The rearrangement reaction can be conducted by a Lewis acid such as anhydrous aluminum chloride, a base, or a cyano compound such as potassium cyanide. As the base, potassium carbonate, calcium hydroxide and sodium carbonate may be used. The Lewis acid, base or potassium cyanide is used usually within a range of from 0.1 to 10 mol times.

No solvent is required. However, in some cases, a solvent inert to the reaction and having a suitable boiling point may improve the operation efficiency or the yield. As a suitable example, the same solvent as used for the benzoyl esterification reaction or dioxane or diglyme may be mentioned.

The reaction temperature is usually from 20° to 150° C. The reaction time is usually from 15 minutes to 10 hours.

Reaction scheme (3) represents a reaction of cyclohexane-1,3-dione with benzoyl cyanide. For this reaction, at least equimolar amount of zinc chloride and at least equimolar amount of a base such as triethylamine are used. There is no particular restriction as to the solvent so long as it is inactive. A preferred solvent may be methylene chloride or ethylene dichloride. The reaction temperature is usually from 0° to 40° C., and the reaction time is usually from 1 to 10 hours.

The benzoic acid or benzoyl chloride used as the starting material of the compound of the present invention can be readily prepared by a combination of various known preparation methods. For example, in the case of a compound wherein the substituent $X_3$ on the benzene ring is $S(O)_nCH_3$, such a compound can be prepared by the following reaction schemes:

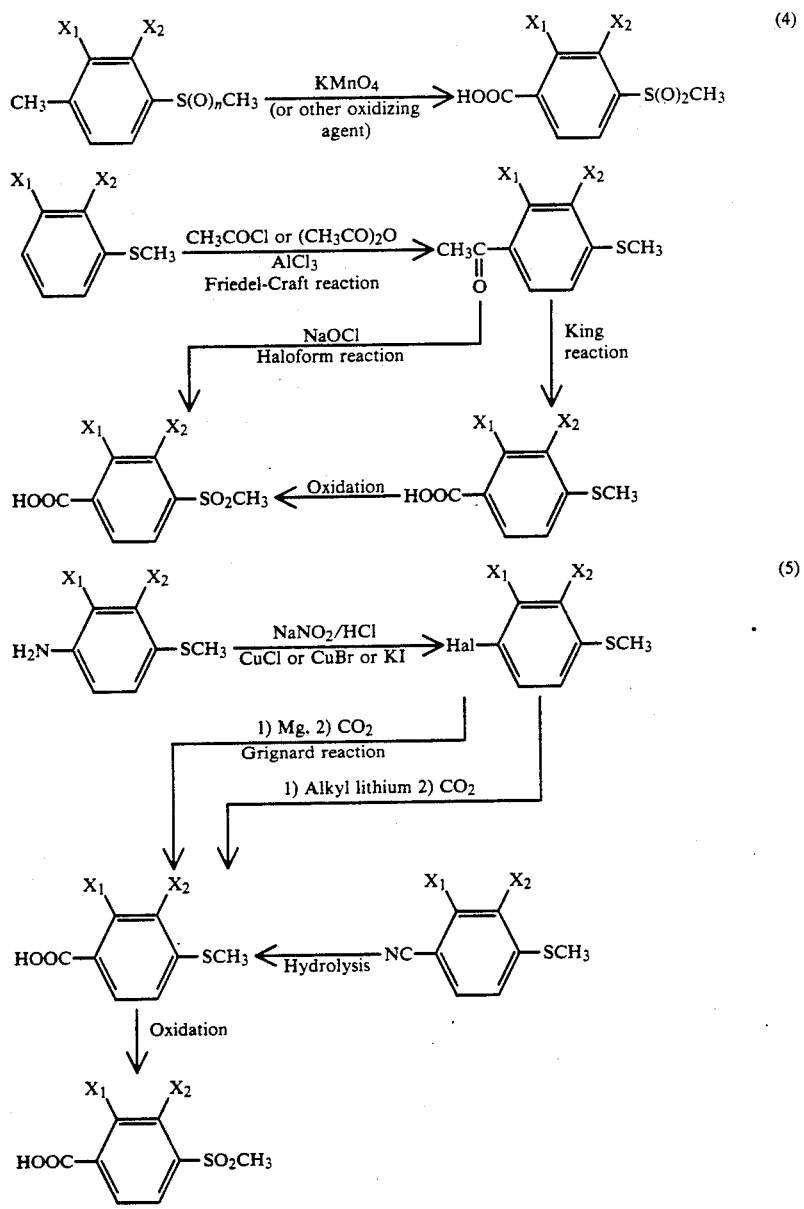

In the above formulas, $X_1$, $X_2$ and n are as defined above, and Hal is bromine or iodine.

These benzoic acids can readily be led to benzoyl chlorides by means of a chlorinating agent such as phosphorus pentachloride, thionyl chloride or sulfuryl chloride. By using the benzoic acids or benzoyl chlorides thus obtained, the compounds of the present invention can readily be prepared in accordance with the reaction schemes (1) to (3).

The present invention will be described in further detail with reference to Examples. However, it should be understood that the present invention is by no means restricted to such specific Examples.

EXAMPLE 1

Preparation of 2-(4-methanesulfonyl-3-methoxymethyl-2-methylbenzoyl)cyclohexane-1,3-dione (Compound No. 1)

1.3 g of potassium carbonate and 3.0 g of N,N'-dicyclohexylcarbodiimide were added to a solution mixture comprising 2.0 g of 4-methanesulfonyl-3-methoxymethyl-2-methylbenzoic acid, 0.9 g of 1,3-cyclohexanedione and 100 ml of t-amyl alcohol. The mixture was stirred at 80° C. for 11 hours. It was concentrated under reduced pressure, and then an aqueous potassium carbonate solution was added. Then, insoluble substances were removed by filtration. The filtrate was washed with chloroform, then acidifed by an addition of concentrated hydrochloric and extracted with chloroform. The chloroform layer was washed with water and with a saturated sodium chloride aqueous solution and then dried over anhydrous sodium sulfate. The solvent was distilled off under reduced pressure to obtain 1.1 g of a crude desired product. This crude product was recrystallized from ethanol to obtain 0.2 g of the desired product. Melting point: 192°–198° C.

EXAMPLE 2

Preparation of 2-(2-chloro-4-methanesulfonyl-3-methoxycarbonylbenzoyl)cyclohexane-1,3-dione (Compound No. 2)

0.28 g of potassium carbonate and 0.77 g of N,N'-dicyclohexylcarbodiimide were added to a solution mixture comprising 1.0 g of 2-chloro-4-methanesulfonyl-3-methoxycarbonyl benzoic acid, 0.38 g of 1,3-cyclohexanedione and 30 ml of t-amyl alcohol. The mixture was stirred at 80° C. for 3 hours. It was concentrated under reduced pressure, and an aqueous potassium carbonate solution was added thereto. Insoluble substances were removed by filtration. The filtrate was washed with chloroform, then acidified by an addition of concentrated hydrochloric acid and extracted with chloroform. The chloroform layer was washed with water and with a saturated sodium chloride aqueous solution and dried over anhydrous sodium sulfate. Then, the solvent was distilled off under reduced pressure to obtain a crude desired product. This crude product was crystallized from ethanol to obtain 0.3 g of the desired product. Melting point: 160°–162° C.

Compounds prepared in the same manner as in the preceding Examples will be given in Tables 1 to 6 including the compounds of the preceding Examples. However, the present invention is not limited by such specific Examples.

The following abbreviations which are used in the Tables, have the following meanings.

Me: methyl, Et: ethyl, Pr-n: n-propyl,
Pr-i: isopropyl, Bu-t: tert-butyl, and
Ms: methanesulfonyl The reference symbols in Tables 1 to 4 have the following meanings.

| | |
|---|---|
| X201; $CH_2OCH_3$ | X202; $CH(CH_3)OCH_3$ |
| X203; $CH(CH_3)OC_2H_5$ | X204; $C(CH_3)_2OCH_3$ |
| X205; $CH_2CH_2OCH_3$ | X206; $CH_2CH_2OH$ |
| X207; $CH_2OH$ | X208; $CH_2OC_2H_5$ |
| X209; $CH_2OCH_2CH=CH_2$ | X210; $CH_2OCH_2C\equiv CH$ |
| X211; $CH_2OCH_2CH_2CH_3$ | X212; $C(CH_3)_2OC_2H_5$ |
| X213; $CH_2CH_2OC_2H_5$ | X214; $CH(C_2H_5)OCH_3$ |
| X215; $CH(C_2H_5)OC_2H_5$ | X216; $CH(CH_3)OH$ |
| X217; $C(CH_3)_2OH$ | X218; $CH(OH)C_2H_5$ |
| X219; $CH_2CH_2OCH(CH_3)_2$ | X220; $CH_2SCH_3$ |
| X221; $CH_2SO_2CH_3$ | X222; $CH_2N(CH_3)_2$ |
| X223; $CH_2N(CH_3)C_2H_5$ | X224; $CH_2CH_2N(CH_3)_2$ |
| X225; $CH_2NHCH_3$ | X226; $CH_2OCOCH_3$ |
| X227; $CH_2OCH(CH_3)_2$ | |

TABLE 1

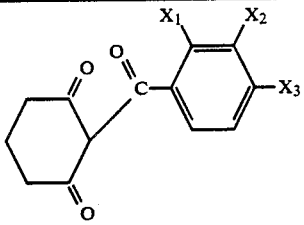

| $X_1$ | $X_2$ | $X_3$ |
|---|---|---|
| Cl | X201 | Ms |
| Cl | X201 | Cl |
| Cl | X202 | Ms |
| Cl | X202 | Cl |
| Cl | X205 | Ms |
| Cl | X205 | Cl |
| Cl | X207 | Ms |

TABLE 1-continued

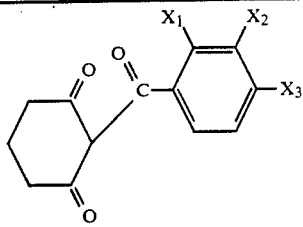

| $X_1$ | $X_2$ | $X_3$ |
|---|---|---|
| Cl | X207 | Cl |
| Cl | X208 | Ms |
| Cl | X208 | Cl |
| Cl | X209 | Ms |
| Cl | X209 | Cl |
| Cl | X210 | Ms |
| Cl | X210 | Cl |
| Cl | X201 | $CF_3$ |
| Cl | X202 | $CF_3$ |
| Cl | X205 | $CF_3$ |
| Cl | X207 | $CF_3$ |
| Cl | X208 | $CF_3$ |
| Cl | X209 | $CF_3$ |
| Cl | X210 | $CF_3$ |
| Me | X201 | Ms |
| Me | X201 | Cl |
| Me | X201 | $CF_3$ |
| Me | X202 | Ms |
| Me | X202 | Cl |
| Me | X202 | $CF_3$ |
| Me | X205 | Ms |
| Me | X205 | Cl |
| Me | X205 | $CF_3$ |
| Me | X207 | Ms |
| Me | X207 | Cl |
| Me | X207 | $CF_3$ |
| Me | X208 | Ms |
| Me | X208 | Cl |
| Me | X208 | $CF_3$ |
| Me | X209 | Ms |
| Me | X209 | Cl |
| Me | X209 | $CF_3$ |
| Me | X210 | Ms |
| Me | X210 | Cl |
| Me | X210 | $CF_3$ |
| Cl | X203 | Ms |
| Cl | X203 | Cl |
| Cl | X203 | $CF_3$ |
| Cl | X204 | Ms |
| Cl | X204 | Cl |
| Cl | X204 | $CF_3$ |
| Cl | X206 | Ms |
| Cl | X206 | Cl |
| Cl | X206 | $CF_3$ |
| Cl | X212 | Ms |
| Cl | X212 | Cl |
| Cl | X212 | $CF_3$ |
| Cl | X213 | Ms |
| Cl | X213 | Cl |
| Cl | X213 | $CF_3$ |
| Cl | X214 | Ms |
| Cl | X214 | Cl |
| Cl | X214 | $CF_3$ |
| Cl | X216 | Ms |
| Cl | X216 | Cl |
| Cl | X216 | $CF_3$ |
| Cl | X217 | Ms |
| Cl | X217 | Cl |
| Cl | X217 | $CF_3$ |
| Cl | X218 | Ms |
| Cl | X218 | Cl |
| Cl | X218 | $CF_3$ |
| Cl | X220 | Ms |
| Cl | X220 | Cl |
| Cl | X220 | $CF_3$ |
| Cl | X222 | Ms |
| Cl | X222 | Cl |
| Cl | X222 | $CF_3$ |
| Cl | X226 | Ms |

TABLE 1-continued

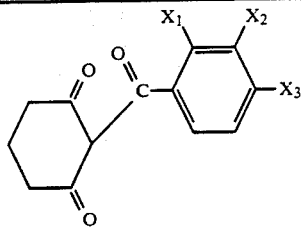

| $X_1$ | $X_2$ | $X_3$ |
|---|---|---|
| Cl | X226 | Cl |
| Cl | X226 | CF$_3$ |
| Cl | X227 | Ms |
| Cl | X227 | Cl |
| Cl | X227 | CF$_3$ |
| Me | X203 | Ms |
| Me | X203 | Cl |
| Me | X203 | CF$_3$ |
| Me | X204 | Ms |
| Me | X204 | Cl |
| Me | X204 | CF$_3$ |
| Me | X206 | Ms |
| Me | X206 | Cl |
| Me | X206 | CF$_3$ |
| Me | X212 | Ms |
| Me | X212 | Cl |
| Me | X212 | CF$_3$ |
| Me | X213 | Ms |
| Me | X213 | Cl |
| Me | X213 | CF$_3$ |
| Me | X214 | Ms |
| Me | X214 | Cl |
| Me | X214 | CF$_3$ |
| Me | X216 | Ms |
| Me | X216 | Cl |
| Me | X216 | CF$_3$ |
| Me | X217 | Ms |
| Me | X217 | Cl |
| Me | X217 | CF$_3$ |
| Me | X218 | Ms |
| Me | X218 | Cl |
| Me | X218 | CF$_3$ |
| Me | X220 | Ms |
| Me | X220 | Cl |
| Me | X220 | CF$_3$ |
| Me | X222 | Ms |
| Me | X222 | Cl |
| Me | X222 | CF$_3$ |
| Me | X226 | Ms |
| Me | X226 | Cl |
| Me | X226 | CF$_3$ |
| Me | X227 | Ms |
| Me | X227 | Cl |
| Me | X227 | CF$_3$ |
| Cl | X211 | Ms |
| Cl | X211 | Cl |
| Cl | X211 | CF$_3$ |
| Cl | X215 | Ms |
| Cl | X215 | Cl |
| Cl | X215 | CF$_3$ |
| Cl | X219 | Ms |
| Cl | X219 | Cl |
| Cl | X219 | CF$_3$ |
| Cl | X221 | Ms |
| Cl | X221 | Cl |
| Cl | X221 | CF$_3$ |
| Cl | X223 | Ms |
| Cl | X223 | Cl |
| Cl | X223 | CF$_3$ |
| Cl | X224 | Ms |
| Cl | X224 | Cl |
| Cl | X224 | CF$_3$ |
| Cl | X225 | Ms |
| Cl | X225 | Cl |
| Cl | X225 | CF$_3$ |
| Me | X211 | Ms |
| Me | X211 | Cl |
| Me | X211 | CF$_3$ |
| Me | X215 | Ms |

TABLE 1-continued

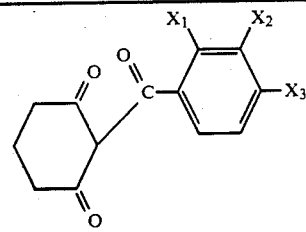

| $X_1$ | $X_2$ | $X_3$ |
|---|---|---|
| Me | X215 | Cl |
| Me | X215 | CF$_3$ |
| Me | X219 | Ms |
| Me | X219 | Cl |
| Me | X219 | CF$_3$ |
| Me | X221 | Ms |
| Me | X221 | Cl |
| Me | X221 | CF$_3$ |
| Me | X223 | Ms |
| Me | X223 | Cl |
| Me | X223 | CF$_3$ |
| Me | X224 | Ms |
| Me | X224 | Cl |
| Me | X224 | CF$_3$ |
| Me | X225 | Ms |
| Me | X225 | Cl |
| Me | X225 | CF$_3$ |
| NO$_2$ | X201 | Ms |
| NO$_2$ | X201 | Cl |
| NO$_2$ | X201 | CF$_3$ |
| NO$_2$ | X202 | Ms |
| NO$_2$ | X202 | Cl |
| NO$_2$ | X202 | CF$_3$ |
| NO$_2$ | X205 | Ms |
| NO$_2$ | X205 | Cl |
| NO$_2$ | X205 | CF$_3$ |
| NO$_2$ | X207 | Ms |
| NO$_2$ | X207 | Cl |
| NO$_2$ | X207 | CF$_3$ |
| NO$_2$ | X208 | Ms |
| NO$_2$ | X208 | Cl |
| NO$_2$ | X208 | CF$_3$ |
| NO$_2$ | X209 | Ms |
| NO$_2$ | X209 | Cl |
| NO$_2$ | X209 | CF$_3$ |
| NO$_2$ | X210 | Ms |
| NO$_2$ | X210 | Cl |
| NO$_2$ | X210 | CF$_3$ |
| Et | X201 | Ms |
| Et | X201 | Cl |
| Et | X201 | CF$_3$ |
| Et | X202 | Ms |
| Et | X202 | Cl |
| Et | X202 | CF$_3$ |
| Et | X205 | Ms |
| Et | X205 | Cl |
| Et | X205 | CF$_3$ |
| Et | X207 | Ms |
| Et | X207 | Cl |
| Et | X207 | CF$_3$ |
| Et | X208 | Ms |
| Et | X208 | Cl |
| Et | X208 | CF$_3$ |
| Et | X209 | Ms |
| Et | X209 | Cl |
| Et | X209 | CF$_3$ |
| Et | X210 | Ms |
| Et | X210 | Cl |
| Et | X210 | CF$_3$ |
| i-Pr | X201 | Ms |
| i-Pr | X201 | Cl |
| i-Pr | X201 | CF$_3$ |
| i-Pr | X202 | Ms |
| i-Pr | X202 | Cl |
| i-Pr | X202 | CF$_3$ |
| i-Pr | X205 | Ms |
| i-Pr | X205 | Cl |
| i-Pr | X205 | CF$_3$ |
| i-Pr | X207 | Ms |

TABLE 1-continued

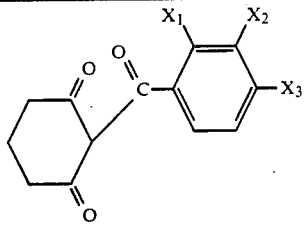

| X₁ | X₂ | X₃ |
|---|---|---|
| i-Pr | X207 | Cl |
| i-Pr | X207 | CF₃ |
| i-Pr | X208 | Ms |
| i-Pr | X208 | Cl |
| i-Pr | X208 | CF₃ |
| i-Pr | X209 | Ms |
| i-Pr | X209 | Cl |
| i-Pr | X209 | CF₃ |
| i-Pr | X210 | Ms |
| i-Pr | X210 | Cl |
| i-Pr | X210 | CF₃ |
| n-Pr | X201 | Ms |
| n-Pr | X201 | Cl |
| n-Pr | X201 | CF₃ |
| n-Pr | X202 | Ms |
| n-Pr | X202 | Cl |
| n-Pr | X202 | CF₃ |
| n-Pr | X205 | Ms |
| n-Pr | X205 | Cl |
| n-Pr | X205 | CF₃ |
| n-Pr | X207 | Ms |
| n-Pr | X207 | Cl |
| n-Pr | X207 | CF₃ |
| n-Pr | X208 | Ms |
| n-Pr | X208 | Cl |
| n-Pr | X208 | CF₃ |
| n-Pr | X209 | Ms |
| n-Pr | X209 | Cl |
| n-Pr | X209 | CF₃ |
| n-Pr | X210 | Ms |
| n-Pr | X210 | Cl |
| n-Pr | X210 | CF₃ |
| CN | X201 | Ms |
| CN | X201 | Cl |
| CN | X201 | CF₃ |
| CN | X202 | Ms |
| CN | X202 | Cl |
| CN | X202 | CF₃ |
| CN | X205 | Ms |
| CN | X205 | Cl |
| CN | X205 | CF₃ |
| CN | X207 | Ms |
| CN | X207 | Cl |
| CN | X207 | CF₃ |
| CN | X208 | Ms |
| CN | X208 | Cl |
| CN | X208 | CF₃ |
| CN | X209 | Ms |
| CN | X209 | Cl |
| CN | X209 | CF₃ |
| CN | X210 | Ms |
| CN | X210 | Cl |
| CN | X210 | CF₃ |
| CF₃ | X201 | Ms |
| CF₃ | X201 | Cl |
| CF₃ | X201 | CF₃ |
| CF₃ | X202 | Ms |
| CF₃ | X202 | Cl |
| CF₃ | X202 | CF₃ |
| CF₃ | X205 | Ms |
| CF₃ | X205 | Cl |
| CF₃ | X205 | CF₃ |
| CF₃ | X207 | Ms |
| CF₃ | X207 | Cl |
| CF₃ | X207 | CF₃ |
| CF₃ | X208 | Ms |
| CF₃ | X208 | Cl |
| CF₃ | X208 | CF₃ |
| CF₃ | X209 | Ms |

TABLE 1-continued

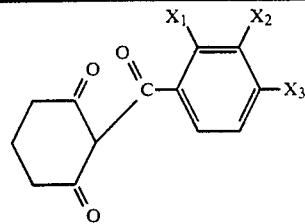

| X₁ | X₂ | X₃ |
|---|---|---|
| CF₃ | X209 | Cl |
| CF₃ | X209 | CF₃ |
| CF₃ | X210 | Ms |
| CF₃ | X210 | Cl |
| CF₃ | X210 | CF₃ |
| F | X201 | Ms |
| F | X201 | Cl |
| F | X201 | CF₃ |
| F | X202 | Ms |
| F | X202 | Cl |
| F | X202 | CF₃ |
| F | X205 | Ms |
| F | X205 | Cl |
| F | X205 | CF₃ |
| F | X207 | Ms |
| F | X207 | Cl |
| F | X207 | CF₃ |
| F | X208 | Ms |
| F | X208 | Cl |
| F | X208 | CF₃ |
| F | X209 | Ms |
| F | X209 | Cl |
| F | X209 | CF₃ |
| F | X210 | Ms |
| F | X210 | Cl |
| F | X210 | CF₃ |
| Br | X201 | Ms |
| Br | X201 | Cl |
| Br | X201 | CF₃ |
| Br | X202 | Ms |
| Br | X202 | Cl |
| Br | X202 | CF₃ |
| Br | X205 | Ms |
| Br | X205 | Cl |
| Br | X205 | CF₃ |
| Br | X207 | Ms |
| Br | X207 | Cl |
| Br | X207 | CF₃ |
| Br | X208 | Ms |
| Br | X208 | Cl |
| Br | X208 | CF₃ |
| Br | X209 | Ms |
| Br | X209 | Cl |
| Br | X209 | CF₃ |
| Br | X210 | Ms |
| Br | X210 | Cl |
| Br | X210 | CF₃ |
| I | X201 | Ms |
| I | X201 | Cl |
| I | X201 | CF₃ |
| I | X202 | Ms |
| I | X202 | Cl |
| I | X202 | CF₃ |
| I | X205 | Ms |
| I | X205 | Cl |
| I | X205 | CF₃ |
| I | X207 | Ms |
| I | X207 | Cl |
| I | X207 | CF₃ |
| I | X208 | Ms |
| I | X208 | Cl |
| I | X208 | CF₃ |
| I | X209 | Ms |
| I | X209 | Cl |
| I | X209 | CF₃ |
| I | X210 | Ms |
| I | X210 | Cl |
| I | X210 | CF₃ |
| MeO | X201 | Ms |

TABLE 1-continued

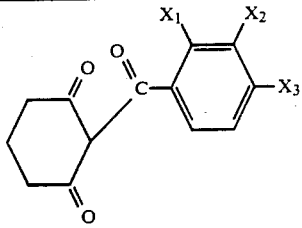

| $X_1$ | $X_2$ | $X_3$ |
|---|---|---|
| MeO | X201 | Cl |
| MeO | X201 | CF$_3$ |
| MeO | X202 | Ms |
| MeO | X202 | Cl |
| MeO | X202 | CF$_3$ |
| MeO | X205 | Ms |
| MeO | X205 | Cl |
| MeO | X205 | CF$_3$ |
| MeO | X207 | Ms |
| MeO | X207 | Cl |
| MeO | X207 | CF$_3$ |
| MeO | X208 | Ms |
| MeO | X208 | Cl |
| MeO | X208 | CF$_3$ |
| MeO | X209 | Ms |
| MeO | X209 | Cl |
| MeO | X209 | CF$_3$ |
| MeO | X210 | Ms |
| MeO | X210 | Cl |
| MeO | X210 | CF$_3$ |
| EtO | X201 | Ms |
| EtO | X201 | Cl |
| EtO | X201 | CF$_3$ |
| EtO | X202 | Ms |
| EtO | X202 | Cl |
| EtO | X202 | CF$_3$ |
| EtO | X205 | Ms |
| EtO | X205 | Cl |
| EtO | X205 | CF$_3$ |
| EtO | X207 | Ms |
| EtO | X207 | Cl |
| EtO | X207 | CF$_3$ |
| EtO | X208 | Ms |
| EtO | X208 | Cl |
| EtO | X208 | CF$_3$ |
| EtO | X209 | Ms |
| EtO | X209 | Cl |
| EtO | X209 | CF$_3$ |
| EtO | X210 | Ms |
| EtO | X210 | Cl |
| EtO | X210 | CF$_3$ |
| i-PrO | X201 | Ms |
| i-PrO | X201 | Cl |
| i-PrO | X201 | CF$_3$ |
| i-PrO | X202 | Ms |
| i-PrO | X202 | Cl |
| i-PrO | X202 | CF$_3$ |
| i-PrO | X205 | Ms |
| i-PrO | X205 | Cl |
| i-PrO | X205 | CF$_3$ |
| i-PrO | X207 | Ms |
| i-PrO | X207 | Cl |
| i-PrO | X207 | CF$_3$ |
| i-PrO | X208 | Ms |
| i-PrO | X208 | Cl |
| i-PrO | X208 | CF$_3$ |
| i-PrO | X209 | Ms |
| i-PrO | X209 | Cl |
| i-PrO | X209 | CF$_3$ |
| i-PrO | X210 | Ms |
| i-PrO | X210 | Cl |
| i-PrO | X210 | CF$_3$ |
| n-PrO | X201 | Ms |
| n-PrO | X201 | Cl |
| n-PrO | X201 | CF$_3$ |
| n-PrO | X202 | Ms |
| n-PrO | X202 | Cl |
| n-PrO | X202 | CF$_3$ |
| n-PrO | X205 | Ms |
| n-PrO | X205 | Cl |
| n-PrO | X205 | CF$_3$ |
| n-PrO | X207 | Ms |
| n-PrO | X207 | Cl |
| n-PrO | X207 | CF$_3$ |
| n-PrO | X208 | Ms |
| n-PrO | X208 | Cl |
| n-PrO | X208 | CF$_3$ |
| n-PrO | X209 | Ms |
| n-PrO | X209 | Cl |
| n-PrO | X209 | CF$_3$ |
| n-PrO | X210 | Ms |
| n-PrO | X210 | Cl |
| n-PrO | X210 | CF$_3$ |
| CHF$_2$ | X201 | Ms |
| CHF$_2$ | X201 | Cl |
| CHF$_2$ | X201 | CF$_3$ |
| CHF$_2$ | X202 | Ms |
| CHF$_2$ | X202 | Cl |
| CHF$_2$ | X202 | CF$_3$ |
| CHF$_2$ | X205 | Ms |
| CHF$_2$ | X205 | Cl |
| CHF$_2$ | X205 | CF$_3$ |
| CHF$_2$ | X207 | Ms |
| CHF$_2$ | X207 | Cl |
| CHF$_2$ | X207 | CF$_3$ |
| CHF$_2$ | X208 | Ms |
| CHF$_2$ | X208 | Cl |
| CHF$_2$ | X208 | CF$_3$ |
| CHF$_2$ | X209 | Ms |
| CHF$_2$ | X209 | Cl |
| CHF$_2$ | X209 | CF$_3$ |
| CHF$_2$ | X210 | Ms |
| CHF$_2$ | X210 | Cl |
| CHF$_2$ | X210 | CF$_3$ |
| CH$_2$CF$_3$ | X201 | Ms |
| CH$_2$CF$_3$ | X201 | Cl |
| CH$_2$CF$_3$ | X201 | CF$_3$ |
| CH$_2$CF$_3$ | X202 | Ms |
| CH$_2$CF$_3$ | X202 | Cl |
| CH$_2$CF$_3$ | X202 | CF$_3$ |
| CH$_2$CF$_3$ | X205 | Ms |
| CH$_2$CF$_3$ | X205 | Cl |
| CH$_2$CF$_3$ | X205 | CF$_3$ |
| CH$_2$CF$_3$ | X207 | Ms |
| CH$_2$CF$_3$ | X207 | Cl |
| CH$_2$CF$_3$ | X207 | CF$_3$ |
| CH$_2$CF$_3$ | X208 | Ms |
| CH$_2$CF$_3$ | X208 | Cl |
| CH$_2$CF$_3$ | X208 | CF$_3$ |
| CH$_2$CF$_3$ | X209 | Ms |
| CH$_2$CF$_3$ | X209 | Cl |
| CH$_2$CF$_3$ | X209 | CF$_3$ |
| CH$_2$CF$_3$ | X210 | Ms |
| CH$_2$CF$_3$ | X210 | Cl |
| CH$_2$CF$_3$ | X210 | CF$_3$ |
| X201 | X201 | Ms |
| X201 | X201 | Cl |
| X201 | X201 | CF$_3$ |
| X201 | X202 | Ms |
| X201 | X202 | Cl |
| X201 | X202 | CF$_3$ |
| X201 | X205 | Ms |
| X201 | X205 | Cl |
| X201 | X205 | CF$_3$ |
| X201 | X207 | Ms |
| X201 | X207 | Cl |
| X201 | X207 | CF$_3$ |
| X201 | X208 | Ms |

TABLE 1-continued

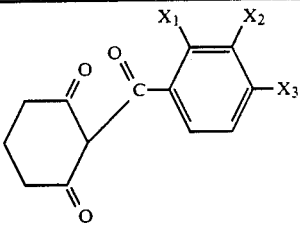

| $X_1$ | $X_2$ | $X_3$ |
|---|---|---|
| X201 | X208 | Cl |
| X201 | X208 | CF$_3$ |
| X201 | X209 | Ms |
| X201 | X209 | Cl |
| X201 | X209 | CF$_3$ |
| X201 | X210 | Ms |
| X201 | X210 | Cl |
| X201 | X210 | CF$_3$ |
| X201 | X203 | Ms |
| X201 | X203 | Cl |
| X201 | X203 | CF$_3$ |
| X201 | X204 | Ms |
| X201 | X204 | Cl |
| X201 | X204 | CF$_3$ |
| X201 | X206 | Ms |
| X201 | X206 | Cl |
| X201 | X206 | CF$_3$ |
| X201 | X212 | Ms |
| X201 | X212 | Cl |
| X201 | X212 | CF$_3$ |
| X201 | X213 | Ms |
| X201 | X213 | Cl |
| X201 | X213 | CF$_3$ |
| X201 | X214 | Ms |
| X201 | X214 | Cl |
| X201 | X214 | CF$_3$ |
| X201 | X216 | Ms |
| X201 | X216 | Cl |
| X201 | X216 | CF$_3$ |
| X201 | X217 | Ms |
| X201 | X217 | Cl |
| X201 | X217 | CF$_3$ |
| X201 | X218 | Ms |
| X201 | X218 | Cl |
| X201 | X218 | CF$_3$ |
| X201 | X220 | Ms |
| X201 | X220 | Cl |
| X201 | X220 | CF$_3$ |
| X201 | X222 | Ms |
| X201 | X222 | Cl |
| X201 | X222 | CF$_3$ |
| X201 | X226 | Ms |
| X201 | X226 | Cl |
| X201 | X226 | CF$_3$ |
| X201 | X227 | Ms |
| X201 | X227 | Cl |
| X201 | X227 | CF$_3$ |
| X201 | X228 | Ms |
| X201 | X228 | Cl |
| X201 | X228 | CF$_3$ |
| X201 | X229 | Ms |
| X201 | X229 | Cl |
| X201 | X229 | CF$_3$ |
| X201 | X230 | Ms |
| X201 | X230 | Cl |
| X201 | X230 | CF$_3$ |
| X201 | X231 | Ms |
| X201 | X231 | Cl |
| X201 | X231 | CF$_3$ |
| X201 | X232 | Ms |
| X201 | X232 | Cl |
| X201 | X232 | CF$_3$ |
| X201 | X233 | Ms |
| X201 | X233 | Cl |
| X201 | X233 | CF$_3$ |
| X201 | X234 | Ms |
| X201 | X234 | Cl |
| X201 | X234 | CF$_3$ |
| X201 | X235 | Ms |

TABLE 1-continued

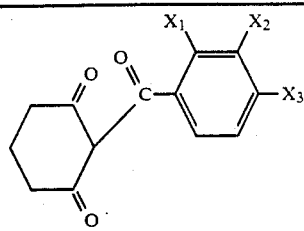

| $X_1$ | $X_2$ | $X_3$ |
|---|---|---|
| X201 | X235 | Cl |
| X201 | X235 | CF$_3$ |
| X202 | X201 | Ms |
| X202 | X201 | Cl |
| X202 | X201 | CF$_3$ |
| X202 | X202 | Ms |
| X202 | X202 | Cl |
| X202 | X202 | CF$_3$ |
| X202 | X205 | Ms |
| X202 | X205 | Cl |
| X202 | X205 | CF$_3$ |
| X202 | X207 | Ms |
| X202 | X207 | Cl |
| X202 | X207 | CF$_3$ |
| X202 | X208 | Ms |
| X202 | X208 | Cl |
| X202 | X208 | CF$_3$ |
| X202 | X209 | Ms |
| X202 | X209 | Cl |
| X202 | X209 | CF$_3$ |
| X202 | X210 | Ms |
| X202 | X210 | Cl |
| X202 | X210 | CF$_3$ |
| X202 | X203 | Ms |
| X202 | X203 | Cl |
| X202 | X203 | CF$_3$ |
| X202 | X204 | Ms |
| X202 | X204 | Cl |
| X202 | X204 | CF$_3$ |
| X202 | X206 | Ms |
| X202 | X206 | Cl |
| X202 | X206 | CF$_3$ |
| X202 | X212 | Ms |
| X202 | X212 | Cl |
| X202 | X212 | CF$_3$ |
| X202 | X213 | Ms |
| X202 | X213 | Cl |
| X202 | X213 | CF$_3$ |
| X202 | X214 | Ms |
| X202 | X214 | Cl |
| X202 | X214 | CF$_3$ |
| X202 | X216 | Ms |
| X202 | X216 | Cl |
| X202 | X216 | CF$_3$ |
| X202 | X217 | Ms |
| X202 | X217 | Cl |
| X202 | X217 | CF$_3$ |
| X202 | X218 | Ms |
| X202 | X218 | Cl |
| X202 | X218 | CF$_3$ |
| X202 | X220 | Ms |
| X202 | X220 | Cl |
| X202 | X220 | CF$_3$ |
| X202 | X222 | Ms |
| X202 | X222 | Cl |
| X202 | X222 | CF$_3$ |
| X202 | X226 | Ms |
| X202 | X226 | Cl |
| X202 | X226 | CF$_3$ |
| X202 | X227 | Ms |
| X202 | X227 | Cl |
| X202 | X227 | CF$_3$ |
| X202 | X228 | Ms |
| X202 | X228 | Cl |
| X202 | X228 | CF$_3$ |
| X202 | X229 | Ms |
| X202 | X229 | Cl |
| X202 | X229 | CF$_3$ |
| X202 | X230 | Ms |

TABLE 1-continued

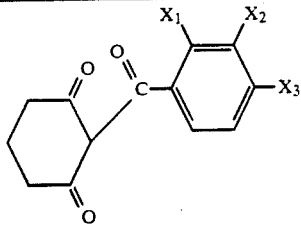

| $X_1$ | $X_2$ | $X_3$ |
|---|---|---|
| X202 | X230 | Cl |
| X202 | X230 | $CF_3$ |
| X202 | X231 | Ms |
| X202 | X231 | Cl |
| X202 | X231 | $CF_3$ |
| X202 | X232 | Ms |
| X202 | X232 | Cl |
| X202 | X232 | $CF_3$ |
| X202 | X233 | Ms |
| X202 | X233 | Cl |
| X202 | X233 | $CF_3$ |
| X202 | X234 | Ms |
| X202 | X234 | Cl |
| X202 | X234 | $CF_3$ |
| X202 | X235 | Ms |
| X202 | X235 | Cl |
| X202 | X235 | $CF_3$ |
| X205 | X201 | Ms |
| X205 | X201 | Cl |
| X205 | X201 | $CF_3$ |
| X205 | X202 | Ms |
| X205 | X202 | Cl |
| X205 | X202 | $CF_3$ |
| X205 | X205 | Ms |
| X205 | X205 | Cl |
| X205 | X205 | $CF_3$ |
| X205 | X207 | Ms |
| X205 | X207 | Cl |
| X205 | X207 | $CF_3$ |
| X205 | X208 | Ms |
| X205 | X208 | Cl |
| X205 | X208 | $CF_3$ |
| X205 | X209 | Ms |
| X205 | X209 | Cl |
| X205 | X209 | $CF_3$ |
| X205 | X210 | Ms |
| X205 | X210 | Cl |
| X205 | X210 | $CF_3$ |
| X205 | X203 | Ms |
| X205 | X203 | Cl |
| X205 | X203 | $CF_3$ |
| X205 | X204 | Ms |
| X205 | X204 | Cl |
| X205 | X204 | $CF_3$ |
| X205 | X206 | Ms |
| X205 | X206 | Cl |
| X205 | X206 | $CF_3$ |
| X205 | X212 | Ms |
| X205 | X212 | Cl |
| X205 | X212 | $CF_3$ |
| X205 | X213 | Ms |
| X205 | X213 | Cl |
| X205 | X213 | $CF_3$ |
| X205 | X214 | Ms |
| X205 | X214 | Cl |
| X205 | X214 | $CF_3$ |
| X205 | X216 | Ms |
| X205 | X216 | Cl |
| X205 | X216 | $CF_3$ |
| X205 | X217 | Ms |
| X205 | X217 | Cl |
| X205 | X217 | $CF_3$ |
| X205 | X218 | Ms |
| X205 | X218 | Cl |
| X205 | X218 | $CF_3$ |
| X205 | X220 | Ms |
| X205 | X220 | Cl |
| X205 | X220 | $CF_3$ |
| X205 | X222 | Ms |

TABLE 1-continued

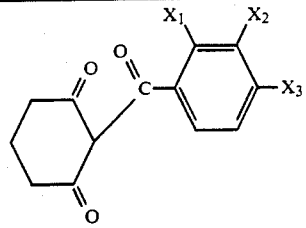

| $X_1$ | $X_2$ | $X_3$ |
|---|---|---|
| X205 | X222 | Cl |
| X205 | X222 | $CF_3$ |
| X205 | X226 | Ms |
| X205 | X226 | Cl |
| X205 | X226 | $CF_3$ |
| X205 | X227 | Ms |
| X205 | X227 | Cl |
| X205 | X227 | $CF_3$ |
| X205 | X228 | Ms |
| X205 | X228 | Cl |
| X205 | X228 | $CF_3$ |
| X205 | X229 | Ms |
| X205 | X229 | Cl |
| X205 | X229 | $CF_3$ |
| X205 | X230 | Ms |
| X205 | X230 | Cl |
| X205 | X230 | $CF_3$ |
| X205 | X231 | Ms |
| X205 | X231 | Cl |
| X205 | X231 | $CF_3$ |
| X205 | X232 | Ms |
| X205 | X232 | Cl |
| X205 | X232 | $CF_3$ |
| X205 | X233 | Ms |
| X205 | X233 | Cl |
| X205 | X233 | $CF_3$ |
| X205 | X234 | Ms |
| X205 | X234 | Cl |
| X205 | X234 | $CF_3$ |
| X207 | X201 | Ms |
| X207 | X201 | Cl |
| X207 | X201 | $CF_3$ |
| X207 | X202 | Ms |
| X207 | X202 | Cl |
| X207 | X202 | $CF_3$ |
| X207 | X205 | Ms |
| X207 | X205 | Cl |
| X207 | X205 | $CF_3$ |
| X207 | X207 | Ms |
| X207 | X207 | Cl |
| X207 | X207 | $CF_3$ |
| X207 | X208 | Ms |
| X207 | X208 | Cl |
| X207 | X208 | $CF_3$ |
| X207 | X209 | Ms |
| X207 | X209 | Cl |
| X207 | X209 | $CF_3$ |
| X207 | X210 | Ms |
| X207 | X210 | Cl |
| X207 | X210 | $CF_3$ |
| X207 | X203 | Ms |
| X207 | X203 | Cl |
| X207 | X203 | $CF_3$ |
| X207 | X204 | Ms |
| X207 | X204 | Cl |
| X207 | X204 | $CF_3$ |
| X207 | X206 | Ms |
| X207 | X206 | Cl |
| X207 | X206 | $CF_3$ |
| X207 | X212 | Ms |
| X207 | X212 | Cl |
| X207 | X212 | $CF_3$ |
| X207 | X213 | Ms |
| X207 | X213 | Cl |
| X207 | X213 | $CF_3$ |
| X207 | X214 | Ms |
| X207 | X214 | Cl |
| X207 | X214 | $CF_3$ |
| X207 | X216 | Ms |

TABLE 1-continued

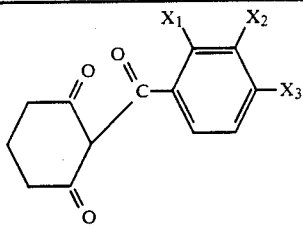

| $X_1$ | $X_2$ | $X_3$ |
|---|---|---|
| X207 | X216 | Cl |
| X207 | X216 | CF$_3$ |
| X207 | X217 | Ms |
| X207 | X217 | Cl |
| X207 | X217 | CF$_3$ |
| X207 | X218 | Ms |
| X207 | X218 | Cl |
| X207 | X218 | CF$_3$ |
| X207 | X220 | Ms |
| X207 | X220 | Cl |
| X207 | X220 | CF$_3$ |
| X207 | X222 | Ms |
| X207 | X222 | Cl |
| X207 | X222 | CF$_3$ |
| X207 | X226 | Ms |
| X207 | X226 | Cl |
| X207 | X226 | CF$_3$ |
| X207 | X227 | Ms |
| X207 | X227 | Cl |
| X207 | X227 | CF$_3$ |
| X208 | X201 | Ms |
| X208 | X201 | Cl |
| X208 | X201 | CF$_3$ |
| X208 | X202 | Ms |
| X208 | X202 | Cl |
| X208 | X202 | CF$_3$ |
| X208 | X205 | Ms |
| X208 | X205 | Cl |
| X208 | X205 | CF$_3$ |
| X208 | X207 | Ms |
| X208 | X207 | Cl |
| X208 | X207 | CF$_3$ |
| X208 | X208 | Ms |
| X208 | X208 | Cl |
| X208 | X208 | CF$_3$ |
| X208 | X209 | Ms |
| X208 | X209 | Cl |
| X208 | X209 | CF$_3$ |
| X208 | X210 | Ms |
| X208 | X210 | Cl |
| X208 | X210 | CF$_3$ |
| X208 | X203 | Ms |
| X208 | X203 | Cl |
| X208 | X203 | CF$_3$ |
| X208 | X204 | Ms |
| X208 | X204 | Cl |
| X208 | X204 | CF$_3$ |
| X208 | X206 | Ms |
| X208 | X206 | Cl |
| X208 | X206 | CF$_3$ |
| X208 | X212 | Ms |
| X208 | X212 | Cl |
| X208 | X212 | CF$_3$ |
| X208 | X213 | Ms |
| X208 | X213 | Cl |
| X208 | X213 | CF$_3$ |
| X208 | X214 | Ms |
| X208 | X214 | Cl |
| X208 | X214 | CF$_3$ |
| X208 | X216 | Ms |
| X208 | X216 | Cl |
| X208 | X216 | CF$_3$ |
| X208 | X217 | Ms |
| X208 | X217 | Cl |
| X208 | X217 | CF$_3$ |
| X208 | X218 | Ms |
| X208 | X218 | Cl |
| X208 | X218 | CF$_3$ |
| X208 | X220 | Ms |

TABLE 1-continued

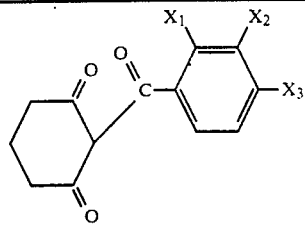

| $X_1$ | $X_2$ | $X_3$ |
|---|---|---|
| X208 | X220 | Cl |
| X208 | X220 | CF$_3$ |
| X208 | X222 | Ms |
| X208 | X222 | Cl |
| X208 | X222 | CF$_3$ |
| X208 | X226 | Ms |
| X208 | X226 | Cl |
| X208 | X226 | CF$_3$ |
| X208 | X227 | Ms |
| X208 | X227 | Cl |
| X208 | X227 | CF$_3$ |
| X209 | X201 | Ms |
| X209 | X201 | Cl |
| X209 | X201 | CF$_3$ |
| X209 | X202 | Ms |
| X209 | X202 | Cl |
| X209 | X202 | CF$_3$ |
| X209 | X205 | Ms |
| X209 | X205 | Cl |
| X209 | X205 | CF$_3$ |
| X209 | X207 | Ms |
| X209 | X207 | Cl |
| X209 | X207 | CF$_3$ |
| X209 | X208 | Ms |
| X209 | X208 | Cl |
| X209 | X208 | CF$_3$ |
| X209 | X209 | Ms |
| X209 | X209 | Cl |
| X209 | X209 | CF$_3$ |
| X209 | X210 | Ms |
| X209 | X210 | Cl |
| X209 | X210 | CF$_3$ |
| X209 | X203 | Ms |
| X209 | X203 | Cl |
| X209 | X203 | CF$_3$ |
| X209 | X204 | Ms |
| X209 | X204 | Cl |
| X209 | X204 | CF$_3$ |
| X209 | X206 | Ms |
| X209 | X206 | Cl |
| X209 | X206 | CF$_3$ |
| X209 | X212 | Ms |
| X209 | X212 | Cl |
| X209 | X212 | CF$_3$ |
| X209 | X213 | Ms |
| X209 | X213 | Cl |
| X209 | X213 | CF$_3$ |
| X209 | X214 | Ms |
| X209 | X214 | Cl |
| X209 | X214 | CF$_3$ |
| X209 | X216 | Ms |
| X209 | X216 | Cl |
| X209 | X216 | CF$_3$ |
| X209 | X217 | Ms |
| X209 | X217 | Cl |
| X209 | X217 | CF$_3$ |
| X209 | X218 | Ms |
| X209 | X218 | Cl |
| X209 | X218 | CF$_3$ |
| X209 | X220 | Ms |
| X209 | X220 | Cl |
| X209 | X220 | CF$_3$ |
| X209 | X222 | Ms |
| X209 | X222 | Cl |
| X209 | X222 | CF$_3$ |
| X209 | X226 | Ms |
| X209 | X226 | Cl |
| X209 | X226 | CF$_3$ |
| X209 | X227 | Ms |

TABLE 1-continued

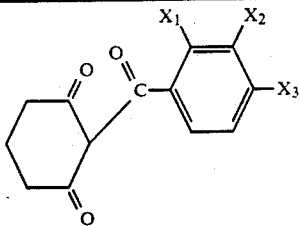

| $X_1$ | $X_2$ | $X_3$ |
|---|---|---|
| X209 | X227 | Cl |
| X209 | X227 | CF$_3$ |
| X210 | X201 | Ms |
| X210 | X201 | Cl |
| X210 | X201 | CF$_3$ |
| X210 | X202 | Ms |
| X210 | X202 | Cl |
| X210 | X202 | CF$_3$ |
| X210 | X205 | Ms |
| X210 | X205 | Cl |
| X210 | X205 | CF$_3$ |
| X210 | X207 | Ms |
| X210 | X207 | Cl |
| X210 | X207 | CF$_3$ |
| X210 | X208 | Ms |
| X210 | X208 | Cl |
| X210 | X208 | CF$_3$ |
| X210 | X209 | Ms |
| X210 | X209 | Cl |
| X210 | X209 | CF$_3$ |
| X210 | X210 | Ms |
| X210 | X210 | Cl |
| X210 | X210 | CF$_3$ |
| X210 | X203 | Ms |
| X210 | X203 | Cl |
| X210 | X203 | CF$_3$ |
| X210 | X204 | Ms |
| X210 | X204 | Cl |
| X210 | X204 | CF$_3$ |
| X210 | X206 | Ms |
| X210 | X206 | Cl |
| X210 | X206 | CF$_3$ |
| X210 | X212 | Ms |
| X210 | X212 | Cl |
| X210 | X212 | CF$_3$ |
| X210 | X213 | Ms |
| X210 | X213 | Cl |
| X210 | X213 | CF$_3$ |
| X210 | X214 | Ms |
| X210 | X214 | Cl |
| X210 | X214 | CF$_3$ |
| X210 | X216 | Ms |
| X210 | X216 | Cl |
| X210 | X216 | CF$_3$ |
| X210 | X217 | Ms |
| X210 | X217 | Cl |
| X210 | X217 | CF$_3$ |
| X210 | X218 | Ms |
| X210 | X218 | Cl |
| X210 | X218 | CF$_3$ |
| X210 | X220 | Ms |
| X210 | X220 | Cl |
| X210 | X220 | CF$_3$ |
| X210 | X222 | Ms |
| X210 | X222 | Cl |
| X210 | X222 | CF$_3$ |
| X210 | X226 | Ms |
| X210 | X226 | Cl |
| X210 | X226 | CF$_3$ |
| X210 | X227 | Ms |
| X210 | X227 | Cl |
| X210 | X227 | CF$_3$ |
| Cl | X201 | NO$_2$ |
| Cl | X201 | MeO |
| Cl | X201 | CN |
| Cl | X201 | SMe |
| Cl | X201 | SOMe |
| Cl | X201 | SO$_2$CF$_3$ |
| Cl | X201 | Br |

TABLE 1-continued

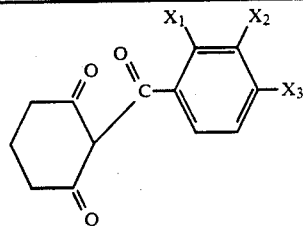

| $X_1$ | $X_2$ | $X_3$ |
|---|---|---|
| Cl | X201 | I |
| Cl | X201 | EtO |
| Cl | X202 | NO$_2$ |
| Cl | X202 | MeO |
| Cl | X202 | CN |
| Cl | X202 | SMe |
| Cl | X202 | SOMe |
| Cl | X202 | SO$_2$CF$_3$ |
| Cl | X202 | Br |
| Cl | X202 | I |
| Cl | X202 | EtO |
| Cl | X205 | NO$_2$ |
| Cl | X205 | MeO |
| Cl | X205 | CN |
| Cl | X205 | SMe |
| Cl | X205 | SOMe |
| Cl | X205 | SO$_2$CF$_3$ |
| Cl | X205 | Br |
| Cl | X205 | I |
| Cl | X205 | EtO |
| Cl | X207 | NO$_2$ |
| Cl | X207 | MeO |
| Cl | X207 | CN |
| Cl | X207 | SMe |
| Cl | X207 | SOMe |
| Cl | X207 | SO$_2$CF$_3$ |
| Cl | X207 | Br |
| Cl | X207 | I |
| Cl | X207 | EtO |
| Cl | X208 | NO$_2$ |
| Cl | X208 | MeO |
| Cl | X208 | CN |
| Cl | X208 | SMe |
| Cl | X208 | SOMe |
| Cl | X208 | SO$_2$CF$_3$ |
| Cl | X208 | Br |
| Cl | X208 | I |
| Cl | X208 | EtO |
| Cl | X209 | NO$_2$ |
| Cl | C209 | MeO |
| Cl | X209 | CN |
| Cl | X209 | SMe |
| Cl | X209 | SOMe |
| Cl | X209 | SO$_2$CF$_3$ |
| Cl | X209 | Br |
| Cl | X209 | I |
| Cl | X209 | EtO |
| Cl | X210 | NO2 |
| Cl | X210 | MeO |
| Cl | X210 | CN |
| Cl | X210 | SMe |
| Cl | X210 | SOMe |
| Cl | X210 | SO$_2$CF$_3$ |
| Cl | X210 | Br |
| Cl | X210 | I |
| Cl | X210 | EtO |
| Me | X201 | NO$_2$ |
| Me | X201 | MeO |
| Me | X201 | CN |
| Me | X201 | SMe |
| Me | X201 | SOMe |
| Me | X201 | SO$_2$CF$_3$ |
| Me | X201 | Br |
| Me | X201 | I |
| Me | X201 | EtO |
| Me | X202 | NO$_2$ |
| Me | X202 | MeO |
| Me | X202 | CN |
| Me | X202 | SMe |

TABLE 1-continued

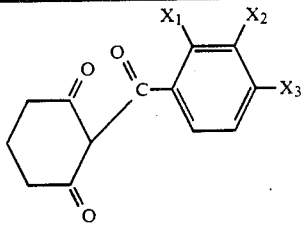

| X₁ | X₂ | X₃ |
|---|---|---|
| Me | X202 | SOMe |
| Me | X202 | SO₂CF₃ |
| Me | X202 | Br |
| Me | X202 | I |
| Me | X202 | EtO |
| Me | X205 | NO₂ |
| Me | X205 | MeO |
| Me | X205 | CN |
| Me | X205 | SMe |
| Me | X205 | SOMe |
| Me | X205 | SO₂CF₃ |
| Me | X205 | Br |
| Me | X205 | I |
| Me | X205 | EtO |
| Me | X207 | NO₂ |
| Me | X207 | MeO |
| Me | X207 | CN |
| Me | X207 | SMe |
| Me | X207 | SOMe |
| Me | X207 | SO₂CF₃ |
| Me | X207 | Br |
| Me | X207 | I |
| Me | X207 | EtO |
| Me | X208 | NO₂ |
| Me | X208 | MeO |
| Me | X208 | CN |
| Me | X208 | SMe |
| Me | X208 | SOMe |
| Me | X208 | SO₂CF₃ |
| Me | X208 | Br |
| Me | X208 | I |
| Me | X208 | EtO |
| Me | X209 | NO₂ |
| Me | X209 | MeO |
| Me | X209 | CN |
| Me | X209 | SMe |
| Me | X209 | SOMe |
| Me | X209 | SO₂CF₃ |
| Me | X209 | Br |
| Me | X209 | I |
| Me | X209 | EtO |
| Me | X210 | NO₂ |
| Me | X210 | MeO |
| Me | X210 | CN |
| Me | X210 | SMe |
| Me | X210 | SOMe |
| Me | X210 | SO₂CF₃ |
| Me | X210 | Br |
| Me | X210 | I |

TABLE 1-continued

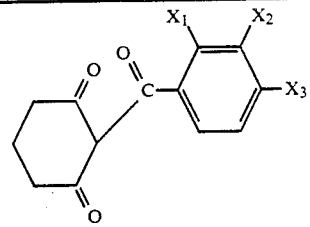

| X₁ | X₂ | X₃ |
|---|---|---|
| Me | X210 | EtO |

TABLE 1

| No. of compound | Substituent R | X | Melting point (°C.) | Nuclear magnetic resonance spectrum (60MHz, d₆-DMSO, δ, ppm) |
|---|---|---|---|---|
| 1 | —CH₂CF₂CHF₂ | H | 170-172 | 3.82(2H, tt, 14Hz, 2Hz), 4.54(2H, s), 6.37(1H, tt, 52Hz, 6Hz), 7.15-8.0(11H, m) |
| 2 | —CH₂CF₂CHF₂ | 2-F | 119-121 | 3.85(2H, tt, 14Hz, 2Hz), 4.57(2H, s), 6.40(1H, tt, 52Hz, 6Hz), 7.15-8.1(10H, m) |
| 3 | —CH₂CF₂CF₃ | H | 156-158 | 3.80(2H, tq, 15Hz, 2Hz), 4.60(2H, s), 6.85(1H, bs), 7.0-8.0(10H, m) |
| 4 | —CH₂CF₂CHFCF₃ | H | 131-133 | 3.50-4.13(2H, m), 4.57(2H, s), 4.57(1H, d, 6-plet, 50Hz, 6Hz), 7.1-8.0(11H, m) |
| 5 | —CH₂CF₂CF₂CF₃ | H | 150-152 | 4.13(2H, tt, 14Hz, 2Hz), 4.67(2H, s), 7.0-8.1(11H, m) |

TABLE 2

| Plant | Compound No. | | | | |
|---|---|---|---|---|---|
| | 1 | 2 | 3 | 4 | 5 |
| Amaranthus retroflexus | 5 | 5 | 5 | 5 | 5 |
| Bidens pilosa | 2 | 2 | 5 | 2 | 5 |
| Brassica arvensis | 5 | 5 | 5 | 5 | 5 |
| Stellaria media | 5 | 5 | 5 | 5 | 5 |
| Solanum nigrum | 3 | 2 | 2 | 4 | 5 |
| Abutilon theophrasti | 3 | 2 | 2 | 5 | 5 |
| Echinochloa crusgalli var. frumentacea | 2 | 1 | 1 | 4 | 5 |
| Digitaria adscendens | 2 | 2 | 2 | 2 | 5 |
| Wheat | — | — | — | — | — |
| Corn | — | — | — | — | — |

Standards for evaluation:
0 ... No herbicidal effect
1 ... Herbicidal effect of below 30%
2 ... Herbicidal effect of 31 to 50%
3 ... Herbicidal effect of 51 to 70%
4 ... Herbicidal effect of 71 to 90%
5 ... Herbicidal effect of 91 to 100%

Phytotoxicity:
—: without any phytotoxicity
±: slight phytotoxicity
+: moderate phytotoxicity
++: strong phytotoxicity
+++: severe phytotoxicity

TABLE 3

| Plant | Compound No. | | | | |
|---|---|---|---|---|---|
| | 1 | 2 | 3 | 4 | 5 |
| Amaranthus retroflexus | 5 | 5 | 5 | 5 | 5 |
| Bidens pilosa | 5 | 5 | 5 | 5 | 5 |
| Brassica arvensis | 5 | 5 | 5 | 5 | 5 |
| Stellaria media | 5 | 5 | 5 | 5 | 5 |
| Solanum nigrum | 5 | 5 | 5 | 5 | 5 |
| Abutilon theophrasti | 5 | 5 | 5 | 5 | 5 |
| Echinochloa crus-galli var. frumentacea | 2 | 2 | 2 | 2 | 2 |
| Digitaria adscendens | 2 | 2 | 2 | 3 | 2 |
| Wheat | — | — | — | — | — |
| Corn | — | — | — | ± | ± |

TABLE 4

| Plant | Compound No. | | | | |
|---|---|---|---|---|---|
| | 1 | 2 | 3 | 4 | 5 |
| *Echinochloa crus-galli* | 5 | 5 | 5 | 5 | 5 |
| *Scripus juncoides* | 5 | 5 | 5 | 5 | 5 |
| *Alisma canaliculatum* | 5 | 5 | 5 | 5 | 5 |
| *Monochoria vaginalis* | 5 | 5 | 5 | 5 | 5 |
| *Cyperus difformis* | 5 | 5 | 5 | 5 | 5 |
| *Sagittaria pygmaea* | 5 | 5 | 5 | 5 | 5 |
| *Cyperus serotinus* | 4 | 4 | 4 | 5 | 5 |
| Rice seedlings | — | — | — | — | — |

TABLE 2

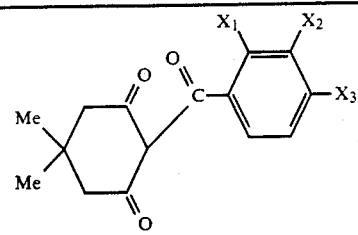

| $X_1$ | $X_2$ | $X_3$ |
|---|---|---|
| Cl | X201 | Ms |
| Cl | X201 | Cl |
| Cl | X202 | Ms |
| Cl | X202 | Cl |
| Cl | X205 | Ms |
| Cl | X205 | Cl |
| Cl | X207 | Ms |
| Cl | X207 | Cl |
| Cl | X208 | Ms |
| Cl | X208 | Cl |
| Cl | X209 | Ms |
| Cl | X209 | Cl |
| Cl | X210 | Ms |
| Cl | X210 | Cl |
| Cl | X201 | $CF_3$ |
| Cl | X202 | $CF_3$ |
| Cl | X205 | $CF_3$ |
| Cl | X207 | $CF_3$ |
| Cl | X208 | $CF_3$ |
| Cl | X209 | $CF_3$ |
| Cl | X210 | $CF_3$ |
| Me | X201 | Ms |
| Me | X201 | Cl |
| Me | X201 | $CF_3$ |
| Me | X202 | Ms |
| Me | X202 | Cl |
| Me | X202 | $CF_3$ |
| Me | X205 | Ms |
| Me | X205 | Cl |
| Me | X205 | $CF_3$ |
| Me | X207 | Ms |
| Me | X207 | Cl |
| Me | X207 | $CF_3$ |
| Me | X208 | Ms |
| Me | X208 | Cl |
| Me | X208 | $CF_3$ |
| Me | X209 | Ms |
| Me | X209 | Cl |
| Me | X209 | $CF_3$ |
| Me | X210 | Ms |
| Me | X210 | Cl |
| Me | X210 | $CF_3$ |
| Cl | X203 | Ms |
| Cl | X203 | Cl |
| Cl | X203 | $CF_3$ |
| Cl | X204 | Ms |
| Cl | X204 | Cl |
| Cl | X204 | $CF_3$ |
| Cl | X206 | Ms |
| Cl | X206 | Cl |
| Cl | X206 | $CF_3$ |
| Cl | X212 | Ms |
| Cl | X212 | Cl |
| Cl | X212 | $CF_3$ |
| Cl | X213 | Ms |
| Cl | X213 | Cl |
| Cl | X213 | $CF_3$ |
| Cl | X214 | Ms |
| Cl | X214 | Cl |
| Cl | X214 | $CF_3$ |
| Cl | X216 | Ms |
| Cl | X216 | Cl |
| Cl | X216 | $CF_3$ |
| Cl | X217 | Ms |
| Cl | X217 | Cl |
| Cl | X217 | $CF_3$ |
| Cl | X218 | Ms |
| Cl | X218 | Cl |
| Cl | X218 | $CF_3$ |
| Cl | X220 | Ms |
| Cl | X220 | Cl |
| Cl | X220 | $CF_3$ |
| Cl | X222 | Ms |
| Cl | X222 | Cl |
| Cl | X222 | $CF_3$ |
| Cl | X226 | Ms |
| Cl | X226 | Cl |
| Cl | X226 | $CF_3$ |
| Cl | X227 | Ms |
| Cl | X227 | Cl |
| Cl | X227 | $CF_3$ |
| Me | X203 | Ms |
| Me | X203 | Cl |
| Me | X203 | $CF_3$ |
| Me | X204 | Ms |
| Me | X204 | Cl |
| Me | X204 | $CF_3$ |
| Me | X206 | Ms |
| Me | X206 | Cl |
| Me | X206 | $CF_3$ |
| Me | X212 | Ms |
| Me | X212 | Cl |
| Me | X212 | $CF_3$ |
| Me | X213 | Ms |
| Me | X213 | Cl |
| Me | X213 | $CF_3$ |
| Me | X214 | Ms |
| Me | X214 | Cl |
| Me | X214 | $CF_3$ |
| Me | X216 | Ms |
| Me | X216 | Cl |
| Me | X216 | $CF_3$ |
| Me | X217 | Ms |
| Me | X217 | Cl |
| Me | X217 | $CF_3$ |
| Me | X218 | Ms |
| Me | X218 | Cl |
| Me | X218 | $CF_3$ |
| Me | X220 | Ms |
| Me | X220 | Cl |
| Me | X220 | $CF_3$ |
| Me | X222 | Ms |
| Me | X222 | Cl |
| Me | X222 | $CF_3$ |
| Me | X226 | Ms |
| Me | X226 | Cl |
| Me | X226 | $CF_3$ |
| Me | X227 | Ms |
| Me | X227 | Cl |
| Me | X227 | $CF_3$ |
| Cl | X211 | Ms |
| Cl | X211 | Cl |
| Cl | X211 | $CF_3$ |
| Cl | X215 | Ms |

TABLE 2-continued

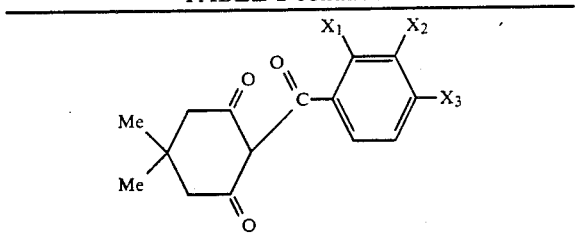

| $X_1$ | $X_2$ | $X_3$ |
|---|---|---|
| Cl | X215 | Cl |
| Cl | X215 | CF$_3$ |
| Cl | X219 | Ms |
| Cl | X219 | Cl |
| Cl | X219 | CF$_3$ |
| Cl | X221 | Ms |
| Cl | X221 | Cl |
| Cl | X221 | CF$_3$ |
| Cl | X223 | Ms |
| Cl | X223 | Cl |
| Cl | X223 | CF$_3$ |
| Cl | X224 | Ms |
| Cl | X224 | Cl |
| Cl | X224 | CF$_3$ |
| Cl | X225 | Ms |
| Cl | X225 | Cl |
| Cl | X225 | CF$_3$ |
| Me | X211 | Ms |
| Me | X211 | Cl |
| Me | X211 | CF$_3$ |
| Me | X215 | Ms |
| Me | X215 | Cl |
| Me | X215 | CF$_3$ |
| Me | X219 | Ms |
| Me | X219 | Cl |
| Me | X219 | CF$_3$ |
| Me | X221 | Ms |
| Me | X221 | Cl |
| Me | X221 | CF$_3$ |
| Me | X223 | Ms |
| Me | X223 | Cl |
| Me | X223 | CF$_3$ |
| Me | X224 | Ms |
| Me | X224 | Cl |
| Me | X224 | CF$_3$ |
| Me | X225 | Ms |
| Me | X225 | Cl |
| Me | X225 | CF$_3$ |
| NO$_2$ | X201 | Ms |
| NO$_2$ | X201 | Cl |
| NO$_2$ | X201 | CF$_3$ |
| NO$_2$ | X202 | Ms |
| NO$_2$ | X202 | Cl |
| NO$_2$ | X202 | CF$_3$ |
| NO$_2$ | X205 | Ms |
| NO$_2$ | X205 | Cl |
| NO$_2$ | X205 | CF$_3$ |
| NO$_2$ | X207 | Ms |
| NO$_2$ | X207 | Cl |
| NO$_2$ | X207 | CF$_3$ |
| NO$_2$ | X208 | Ms |
| NO$_2$ | X208 | Cl |
| NO$_2$ | X208 | CF$_3$ |
| NO$_2$ | X209 | Ms |
| NO$_2$ | X209 | Cl |
| NO$_2$ | X209 | CF$_3$ |
| NO$_2$ | X210 | Ms |
| NO$_2$ | X210 | Cl |
| NO$_2$ | X210 | CF$_3$ |
| Et | X201 | Ms |
| Et | X201 | Cl |
| Et | X201 | CF$_3$ |
| Et | X202 | Ms |
| Et | X202 | Cl |
| Et | X202 | CF$_3$ |
| Et | X205 | Ms |
| Et | X205 | Cl |
| Et | X205 | CF$_3$ |
| Et | X207 | Ms |

TABLE 2-continued

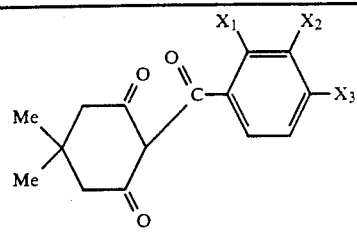

| $X_1$ | $X_2$ | $X_3$ |
|---|---|---|
| Et | X207 | Cl |
| Et | X207 | CF$_3$ |
| Et | X208 | Ms |
| Et | X208 | Cl |
| Et | X208 | CF$_3$ |
| Et | X209 | Ms |
| Et | X209 | Cl |
| Et | X209 | CF$_3$ |
| Et | X210 | Ms |
| Et | X210 | Cl |
| Et | X210 | CF$_3$ |
| i-Pr | X201 | Ms |
| i-Pr | X201 | Cl |
| i-Pr | X201 | CF$_3$ |
| i-Pr | X202 | Ms |
| i-Pr | X202 | Cl |
| i-Pr | X202 | CF$_3$ |
| i-Pr | X205 | Ms |
| i-Pr | X205 | Cl |
| i-Pr | X205 | CF$_3$ |
| i-Pr | X207 | Ms |
| i-Pr | X207 | Cl |
| i-Pr | X207 | CF$_3$ |
| i-Pr | X208 | Ms |
| i-Pr | X208 | Cl |
| i-Pr | X208 | CF$_3$ |
| i-Pr | X209 | Ms |
| i-Pr | X209 | Cl |
| i-Pr | X209 | CF$_3$ |
| i-Pr | X210 | Ms |
| i-Pr | X210 | Cl |
| i-Pr | X210 | CF$_3$ |
| n-Pr | X201 | Ms |
| n-Pr | X201 | Cl |
| n-Pr | X201 | CF$_3$ |
| n-Pr | X202 | Ms |
| n-Pr | X202 | Cl |
| n-Pr | X202 | CF$_3$ |
| n-Pr | X205 | Ms |
| n-Pr | X205 | Cl |
| n-Pr | X205 | CF$_3$ |
| n-Pr | X207 | Ms |
| n-Pr | X207 | Cl |
| n-Pr | X207 | CF$_3$ |
| n-Pr | X208 | Ms |
| n-Pr | X208 | Cl |
| n-Pr | X208 | CF$_3$ |
| n-Pr | X209 | Ms |
| n-Pr | X209 | Cl |
| n-Pr | X209 | CF$_3$ |
| n-Pr | X210 | Ms |
| n-Pr | X210 | Cl |
| n-Pr | X210 | CF$_3$ |
| CN | X201 | Ms |
| CN | X201 | Cl |
| CN | X201 | CF$_3$ |
| CN | X202 | Ms |
| CN | X202 | Cl |
| CN | X202 | CF$_3$ |
| CN | X205 | Ms |
| CN | X205 | Cl |
| CN | X205 | CF$_3$ |
| CN | X207 | Ms |
| CN | X207 | Cl |
| CN | X207 | CF$_3$ |
| CN | X208 | Ms |
| CN | X208 | Cl |
| CN | X208 | CF$_3$ |
| CN | X209 | Ms |

TABLE 2-continued

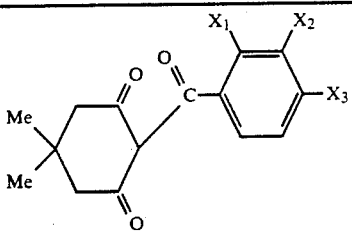

| $X_1$ | $X_2$ | $X_3$ |
|---|---|---|
| CN | X209 | Cl |
| CN | X209 | CF$_3$ |
| CN | X210 | Ms |
| CN | X210 | Cl |
| CN | X210 | CF$_3$ |
| CF$_3$ | X201 | Ms |
| CF$_3$ | X201 | Cl |
| CF$_3$ | X201 | CF$_3$ |
| CF$_3$ | X202 | Ms |
| CF$_3$ | X202 | Cl |
| CF$_3$ | X202 | CF$_3$ |
| CF$_3$ | X205 | Ms |
| CF$_3$ | X205 | Cl |
| CF$_3$ | X205 | CF$_3$ |
| CF$_3$ | X207 | Ms |
| CF$_3$ | X207 | Cl |
| CF$_3$ | X207 | CF$_3$ |
| CF$_3$ | X208 | Ms |
| CF$_3$ | X208 | Cl |
| CF$_3$ | X208 | CF$_3$ |
| CF$_3$ | X209 | Ms |
| CF$_3$ | X209 | Cl |
| CF$_3$ | X209 | CF$_3$ |
| CF$_3$ | X210 | Ms |
| CF$_3$ | X210 | Cl |
| CF$_3$ | X210 | CF$_3$ |
| F | X201 | Ms |
| F | X201 | Cl |
| F | X201 | CF$_3$ |
| F | X202 | Ms |
| F | X202 | Cl |
| F | X202 | CF$_3$ |
| F | X205 | Ms |
| F | X205 | Cl |
| F | X205 | CF$_3$ |
| F | X207 | Ms |
| F | X207 | Cl |
| F | X207 | CF$_3$ |
| F | X208 | Ms |
| F | X208 | Cl |
| F | X208 | CF$_3$ |
| F | X209 | Ms |
| F | X209 | Cl |
| F | X209 | CF$_3$ |
| F | X210 | Ms |
| F | X210 | Cl |
| F | X210 | CF$_3$ |
| Br | X201 | Ms |
| Br | X201 | Cl |
| Br | X201 | CF$_3$ |
| Br | X202 | Ms |
| Br | X202 | Cl |
| Br | X202 | CF$_3$ |
| Br | X205 | Ms |
| Br | X205 | Cl |
| Br | X205 | CF$_3$ |
| Br | X207 | Ms |
| Br | X207 | Cl |
| Br | X207 | CF$_3$ |
| Br | X208 | Ms |
| Br | X208 | Cl |
| Br | X208 | CF$_3$ |
| Br | X209 | Ms |
| Br | X209 | Cl |
| Br | X209 | CF$_3$ |
| Br | X210 | Ms |
| Br | X210 | Cl |
| Br | X210 | CF$_3$ |
| I | X201 | Ms |

TABLE 2-continued

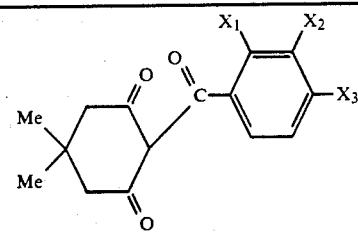

| $X_1$ | $X_2$ | $X_3$ |
|---|---|---|
| I | X201 | Cl |
| I | X201 | CF$_3$ |
| I | X202 | Ms |
| I | X202 | Cl |
| I | X202 | CF$_3$ |
| I | X205 | Ms |
| I | X205 | Cl |
| I | X205 | CF$_3$ |
| I | X207 | Ms |
| I | X207 | Cl |
| I | X207 | CF$_3$ |
| I | X208 | Ms |
| I | X208 | Cl |
| I | X208 | CF$_3$ |
| I | X209 | Ms |
| I | X209 | Cl |
| I | X209 | CF$_3$ |
| I | X210 | Ms |
| I | X210 | Cl |
| I | X210 | CF$_3$ |
| MeO | X201 | Ms |
| MeO | X201 | Cl |
| MeO | X201 | CF$_3$ |
| MeO | X202 | Ms |
| MeO | X202 | Cl |
| MeO | X202 | CF$_3$ |
| MeO | X205 | Ms |
| MeO | X205 | Cl |
| MeO | X205 | CF$_3$ |
| MeO | X207 | Ms |
| MeO | X207 | Cl |
| MeO | X207 | CF$_3$ |
| MeO | X208 | Ms |
| MeO | X208 | Cl |
| MeO | X208 | CF$_3$ |
| MeO | X209 | Ms |
| MeO | X209 | Cl |
| MeO | X209 | CF$_3$ |
| MeO | X210 | Ms |
| MeO | X210 | Cl |
| MeO | X210 | CF$_3$ |
| EtO | X201 | Ms |
| EtO | X201 | Cl |
| EtO | X201 | CF$_3$ |
| EtO | X202 | Ms |
| EtO | X202 | Cl |
| EtO | X202 | CF$_3$ |
| EtO | X205 | Ms |
| EtO | X205 | Cl |
| EtO | X205 | CF$_3$ |
| EtO | X207 | Ms |
| EtO | X207 | Cl |
| EtO | X207 | CF$_3$ |
| EtO | X208 | Ms |
| EtO | X208 | Cl |
| EtO | X208 | CF$_3$ |
| EtO | X209 | Ms |
| EtO | X209 | Cl |
| EtO | X209 | CF$_3$ |
| EtO | X210 | Ms |
| EtO | X210 | Cl |
| EtO | X210 | CF$_3$ |
| i-PrO | X201 | Ms |
| i-PrO | X201 | Cl |
| i-PrO | X201 | CF$_3$ |
| i-PrO | X202 | Ms |
| i-PrO | X202 | Cl |
| i-PrO | X202 | CF$_3$ |
| i-PrO | X205 | Ms |

TABLE 2-continued

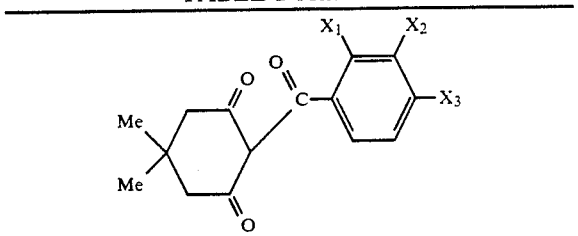

| $X_1$ | $X_2$ | $X_3$ |
|---|---|---|
| i-PrO | X205 | Cl |
| i-PrO | X205 | $CF_3$ |
| i-PrO | X207 | Ms |
| i-PrO | X207 | Cl |
| i-PrO | X207 | $CF_3$ |
| i-PrO | X208 | Ms |
| i-PrO | X208 | Cl |
| i-PrO | X208 | $CF_3$ |
| i-PrO | X209 | Ms |
| i-PrO | X209 | Cl |
| i-PrO | X209 | $CF_3$ |
| i-PrO | X210 | Ms |
| i-PrO | X210 | Cl |
| i-PrO | X210 | $CF_3$ |
| n-PrO | X201 | Ms |
| n-PrO | X201 | Cl |
| n-PrO | X201 | $CF_3$ |
| n-PrO | X202 | Ms |
| n-PrO | X202 | Cl |
| n-PrO | X202 | $CF_3$ |
| n-PrO | X205 | Ms |
| n-PrO | X205 | Cl |
| n-PrO | X205 | $CF_3$ |
| n-PrO | X207 | Ms |
| n-PrO | X207 | Cl |
| n-PrO | X207 | $CF_3$ |
| n-PrO | X208 | Ms |
| n-PrO | X208 | Cl |
| n-PrO | X208 | $CF_3$ |
| n-PrO | X209 | Ms |
| n-PrO | X209 | Cl |
| n-PrO | X209 | $CF_3$ |
| n-PrO | X210 | Ms |
| n-PrO | X210 | Cl |
| n-PrO | X210 | $CF_3$ |
| $CHF_2$ | X201 | Ms |
| $CHF_2$ | X201 | Cl |
| $CHF_2$ | X201 | $CF_3$ |
| $CHF_2$ | X202 | Ms |
| $CHF_2$ | X202 | Cl |
| $CHF_2$ | X202 | $CF_3$ |
| $CHF_2$ | X205 | Ms |
| $CHF_2$ | X205 | Cl |
| $CHF_2$ | X205 | $CF_3$ |
| $CHF_2$ | X207 | Ms |
| $CHF_2$ | X207 | Cl |
| $CHF_2$ | X207 | $CF_3$ |
| $CHF_2$ | X208 | Ms |
| $CHF_2$ | X208 | Cl |
| $CHF_2$ | X208 | $CF_3$ |
| $CHF_2$ | X209 | Ms |
| $CHF_2$ | X209 | Cl |
| $CHF_2$ | X209 | $CF_3$ |
| $CHF_2$ | X210 | Ms |
| $CHF_2$ | X210 | Cl |
| $CHF_2$ | X210 | $CF_3$ |
| $CH_2CF_3$ | X201 | Ms |
| $CH_2CF_3$ | X201 | Cl |
| $CH_2CF_3$ | X201 | $CF_3$ |
| $CH_2CF_3$ | X202 | Ms |
| $CH_2CF_3$ | X202 | Cl |
| $CH_2CF_3$ | X202 | $CF_3$ |
| $CH_2CF_3$ | X205 | Ms |
| $CH_2CF_3$ | X205 | Cl |
| $CH_2CF_3$ | X205 | $CF_3$ |
| $CH_2CF_3$ | X207 | Ms |
| $CH_2CF_3$ | X207 | Cl |
| $CH_2CF_3$ | X207 | $CF_3$ |
| $CH_2CF_3$ | X208 | Ms |

TABLE 2-continued

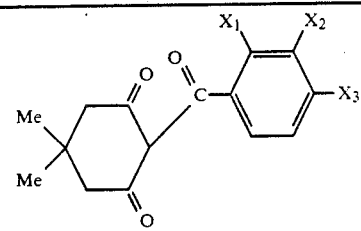

| $X_1$ | $X_2$ | $X_3$ |
|---|---|---|
| $CH_2CF_3$ | X208 | Cl |
| $CH_2CF_3$ | X208 | $CF_3$ |
| $CH_2CF_3$ | X209 | Ms |
| $CH_2CF_3$ | X209 | Cl |
| $CH_2CF_3$ | X209 | $CF_3$ |
| $CH_2CF_3$ | X210 | Ms |
| $CH_2CF_3$ | X210 | Cl |
| $CH_2CF_3$ | X210 | $CF_3$ |
| X201 | X201 | Ms |
| X201 | X201 | Cl |
| X201 | X201 | $CF_3$ |
| X201 | X202 | Ms |
| X201 | X202 | Cl |
| X201 | X202 | $CF_3$ |
| X201 | X205 | Ms |
| X201 | X205 | Cl |
| X201 | X205 | $CF_3$ |
| X201 | X207 | Ms |
| X201 | X207 | Cl |
| X201 | X207 | $CF_3$ |
| X201 | X208 | Ms |
| X201 | X208 | Cl |
| X201 | X208 | $CF_3$ |
| X201 | X209 | Ms |
| X201 | X209 | Cl |
| X201 | X209 | $CF_3$ |
| X201 | X210 | Ms |
| X201 | X210 | Cl |
| X201 | X210 | $CF_3$ |
| X201 | X203 | Ms |
| X201 | X203 | Cl |
| X201 | X203 | $CF_3$ |
| X201 | X204 | Ms |
| X201 | X204 | Cl |
| X201 | X204 | $CF_3$ |
| X201 | X206 | Ms |
| X201 | X206 | Cl |
| X201 | X206 | $CF_3$ |
| X201 | X212 | Ms |
| X201 | X212 | Cl |
| X201 | X212 | $CF_3$ |
| X201 | X213 | Ms |
| X201 | X213 | Cl |
| X201 | X213 | $CF_3$ |
| X201 | X214 | Ms |
| X201 | X214 | Cl |
| X201 | X214 | $CF_3$ |
| X201 | X216 | Ms |
| X201 | X216 | Cl |
| X201 | X216 | $CF_3$ |
| X201 | X217 | Ms |
| X201 | X217 | Cl |
| X201 | X217 | $CF_3$ |
| X201 | X218 | Ms |
| X201 | X218 | Cl |
| X201 | X218 | $CF_3$ |
| X201 | X220 | Ms |
| X201 | X220 | Cl |
| X201 | X220 | $CF_3$ |
| X201 | X222 | Ms |
| X201 | X222 | Cl |
| X201 | X222 | $CF_3$ |
| X201 | X226 | Ms |
| X201 | X226 | Cl |
| X201 | X226 | $CF_3$ |
| X201 | X227 | Ms |
| X201 | X227 | Cl |
| X201 | X227 | $CF_3$ |
| X201 | X228 | Ms |

TABLE 2-continued

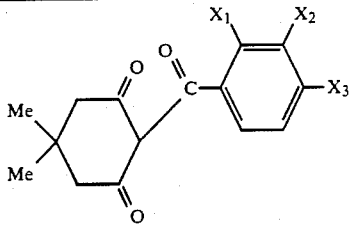

| $X_1$ | $X_2$ | $X_3$ |
|---|---|---|
| X201 | X228 | Cl |
| X201 | X228 | $CF_3$ |
| X201 | X229 | Ms |
| X201 | X229 | Cl |
| X201 | X229 | $CF_3$ |
| X201 | X230 | Ms |
| X201 | X230 | Cl |
| X201 | X230 | $CF_3$ |
| X201 | X231 | Ms |
| X201 | X231 | Cl |
| X201 | X231 | $CF_3$ |
| X201 | X232 | Ms |
| X201 | X232 | Cl |
| X201 | X232 | $CF_3$ |
| X201 | X233 | Ms |
| X201 | X233 | Cl |
| X201 | X233 | $CF_3$ |
| X201 | X234 | Ms |
| X201 | X234 | Cl |
| X201 | X234 | $CF_3$ |
| X201 | X235 | Ms |
| X201 | X235 | Cl |
| X201 | X235 | $CF_3$ |
| X202 | X201 | Ms |
| X202 | X201 | Cl |
| X202 | X201 | $CF_3$ |
| X202 | X202 | Ms |
| X202 | X202 | Cl |
| X202 | X202 | $CF_3$ |
| X202 | X205 | Ms |
| X202 | X205 | Cl |
| X202 | X205 | $CF_3$ |
| X202 | X207 | Ms |
| X202 | X207 | Cl |
| X202 | X207 | $CF_3$ |
| X202 | X208 | Ms |
| X202 | X208 | Cl |
| X202 | X208 | $CF_3$ |
| X202 | X209 | Ms |
| X202 | X209 | Cl |
| X202 | X209 | $CF_3$ |
| X202 | X210 | Ms |
| X202 | X210 | Cl |
| X202 | X210 | $CF_3$ |
| X202 | X203 | Ms |
| X202 | X203 | Cl |
| X202 | X203 | $CF_3$ |
| X202 | X204 | Ms |
| X202 | X204 | Cl |
| X202 | X204 | $CF_3$ |
| X202 | X206 | Ms |
| X202 | X206 | Cl |
| X202 | X206 | $CF_3$ |
| X202 | X212 | Ms |
| X202 | X212 | Cl |
| X202 | X212 | $CF_3$ |
| X202 | X213 | Ms |
| X202 | X213 | Cl |
| X202 | X213 | $CF_3$ |
| X202 | X214 | Ms |
| X202 | X214 | Cl |
| X202 | X214 | $CF_3$ |
| X202 | X216 | Ms |
| X202 | X216 | Cl |
| X202 | X216 | $CF_3$ |
| X202 | X217 | Ms |
| X202 | X217 | Cl |
| X202 | X217 | $CF_3$ |
| X202 | X218 | Ms |

TABLE 2-continued

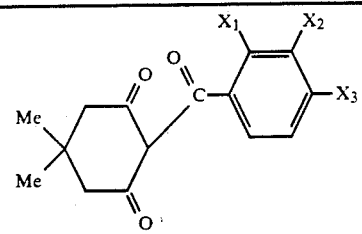

| $X_1$ | $X_2$ | $X_3$ |
|---|---|---|
| X202 | X218 | Cl |
| X202 | X218 | $CF_3$ |
| X202 | X220 | Ms |
| X202 | X220 | Cl |
| X202 | X220 | $CF_3$ |
| X202 | X222 | Ms |
| X202 | X222 | Cl |
| X202 | X222 | $CF_3$ |
| X202 | X226 | Ms |
| X202 | X226 | Cl |
| X202 | X226 | $CF_3$ |
| X202 | X227 | Ms |
| X202 | X227 | Cl |
| X202 | X227 | $CF_3$ |
| X202 | X228 | Ms |
| X202 | X228 | Cl |
| X202 | X228 | $CF_3$ |
| X202 | X229 | Ms |
| X202 | X229 | Cl |
| X202 | X229 | $CF_3$ |
| X202 | X230 | Ms |
| X202 | X230 | Cl |
| X202 | X230 | $CF_3$ |
| X202 | X231 | Ms |
| X202 | X231 | Cl |
| X202 | X231 | $CF_3$ |
| X202 | X232 | Ms |
| X202 | X232 | Cl |
| X202 | X232 | $CF_3$ |
| X202 | X233 | Ms |
| X202 | X233 | Cl |
| X202 | X233 | $CF_3$ |
| X202 | X234 | Ms |
| X202 | X234 | Cl |
| X202 | X234 | $CF_3$ |
| X202 | X235 | Ms |
| X202 | X235 | Cl |
| X202 | X235 | $CF_3$ |
| X205 | X201 | Ms |
| X205 | X201 | Cl |
| X205 | X201 | $CF_3$ |
| X205 | X202 | Ms |
| X205 | X202 | Cl |
| X205 | X202 | $CF_3$ |
| X205 | X205 | Ms |
| X205 | X205 | Cl |
| X205 | X205 | $CF_3$ |
| X205 | X207 | Ms |
| X205 | X207 | Cl |
| X205 | X207 | $CF_3$ |
| X205 | X208 | Ms |
| X205 | X208 | Cl |
| X205 | X208 | $CF_3$ |
| X205 | X209 | Ms |
| X205 | X209 | Cl |
| X205 | X209 | $CF_3$ |
| X205 | X210 | Ms |
| X205 | X210 | Cl |
| X205 | X210 | $CF_3$ |
| X205 | X203 | Ms |
| X205 | X203 | Cl |
| X205 | X203 | $CF_3$ |
| X205 | X204 | Ms |
| X205 | X204 | Cl |
| X205 | X204 | $CF_3$ |
| X205 | X206 | Ms |
| X205 | X206 | Cl |
| X205 | X206 | $CF_3$ |
| X205 | X212 | Ms |

TABLE 2-continued

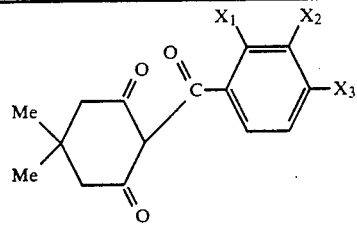

| $X_1$ | $X_2$ | $X_3$ |
|---|---|---|
| X205 | X212 | Cl |
| X205 | X212 | $CF_3$ |
| X205 | X213 | Ms |
| X205 | X213 | Cl |
| X205 | X213 | $CF_3$ |
| X205 | X214 | Ms |
| X205 | X214 | Cl |
| X205 | X214 | $CF_3$ |
| X205 | X216 | Ms |
| X205 | X216 | Cl |
| X205 | X216 | $CF_3$ |
| X205 | X217 | Ms |
| X205 | X217 | Cl |
| X205 | X217 | $CF_3$ |
| X205 | X218 | Ms |
| X205 | X218 | Cl |
| X205 | X218 | $CF_3$ |
| X205 | X220 | Ms |
| X205 | X220 | Cl |
| X205 | X220 | $CF_3$ |
| X205 | X222 | Ms |
| X205 | X222 | Cl |
| X205 | X222 | $CF_3$ |
| X205 | X226 | Ms |
| X205 | X226 | Cl |
| X205 | X226 | $CF_3$ |
| X205 | X227 | Ms |
| X205 | X227 | Cl |
| X205 | X227 | $CF_3$ |
| X205 | X228 | Ms |
| X205 | X228 | Cl |
| X205 | X228 | $CF_3$ |
| X205 | X229 | Ms |
| X205 | X229 | Cl |
| X205 | X229 | $CF_3$ |
| X205 | X230 | Ms |
| X205 | X230 | Cl |
| X205 | X230 | $CF_3$ |
| X205 | X231 | Ms |
| X205 | X231 | Cl |
| X205 | X231 | $CF_3$ |
| X205 | X232 | Ms |
| X205 | X232 | Cl |
| X205 | X232 | $CF_3$ |
| X205 | X233 | Ms |
| X205 | X233 | Cl |
| X205 | X233 | $CF_3$ |
| X205 | X234 | Ms |
| X205 | X234 | Cl |
| X205 | X234 | $CF_3$ |
| X207 | X201 | Ms |
| X207 | X201 | Cl |
| X207 | X201 | $CF_3$ |
| X207 | X202 | Ms |
| X207 | X202 | Cl |
| X207 | X202 | $CF_3$ |
| X207 | X205 | Ms |
| X207 | X205 | Cl |
| X207 | X205 | $CF_3$ |
| X207 | X207 | Ms |
| X207 | X207 | Cl |
| X207 | X207 | $CF_3$ |
| X207 | X208 | Ms |
| X207 | X208 | Cl |
| X207 | X208 | $CF_3$ |
| X207 | X209 | Ms |
| X207 | X209 | Cl |
| X207 | X209 | $CF_3$ |
| X207 | X210 | Ms |

TABLE 2-continued

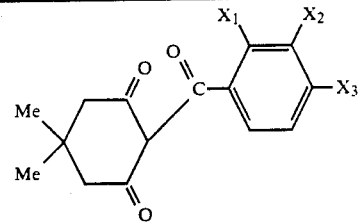

| $X_1$ | $X_2$ | $X_3$ |
|---|---|---|
| X207 | X210 | Cl |
| X207 | X210 | $CF_3$ |
| X207 | X203 | Ms |
| X207 | X203 | Cl |
| X207 | X203 | $CF_3$ |
| X207 | X204 | Ms |
| X207 | X204 | Cl |
| X207 | X204 | $CF_3$ |
| X207 | X206 | Ms |
| X207 | X206 | Cl |
| X207 | X206 | $CF_3$ |
| X207 | X212 | Ms |
| X207 | X212 | Cl |
| X207 | X212 | $CF_3$ |
| X207 | X213 | Ms |
| X207 | X213 | Cl |
| X207 | X213 | $CF_3$ |
| X207 | X214 | Ms |
| X207 | X214 | Cl |
| X207 | X214 | $CF_3$ |
| X207 | X216 | Ms |
| X207 | X216 | Cl |
| X207 | X216 | $CF_3$ |
| X207 | X217 | Ms |
| X207 | X217 | Cl |
| X207 | X217 | $CF_3$ |
| X207 | X218 | Ms |
| X207 | X218 | Cl |
| X207 | X218 | $CF_3$ |
| X207 | X220 | Ms |
| X207 | X220 | Cl |
| X207 | X220 | $CF_3$ |
| X207 | X222 | Ms |
| X207 | X222 | Cl |
| X207 | X222 | $CF_3$ |
| X207 | X226 | Ms |
| X207 | X226 | Cl |
| X207 | X226 | $CF_3$ |
| X207 | X227 | Ms |
| X207 | X227 | Cl |
| X207 | X227 | $CF_3$ |
| X208 | X201 | Ms |
| X208 | X201 | Cl |
| X208 | X201 | $CF_3$ |
| X208 | X202 | Ms |
| X208 | X202 | Cl |
| X208 | X202 | $CF_3$ |
| X208 | X205 | Ms |
| X208 | X205 | Cl |
| X208 | X205 | $CF_3$ |
| X208 | X207 | Ms |
| X208 | X207 | Cl |
| X208 | X207 | $CF_3$ |
| X208 | X208 | Ms |
| X208 | X208 | Cl |
| X208 | X208 | $CF_3$ |
| X208 | X209 | Ms |
| X208 | X209 | Cl |
| X208 | X209 | $CF_3$ |
| X208 | X210 | Ms |
| X208 | X210 | Cl |
| X208 | X210 | $CF_3$ |
| X208 | X203 | Ms |
| X208 | X203 | Cl |
| X208 | X203 | $CF_3$ |
| X208 | X204 | Ms |
| X208 | X204 | Cl |
| X208 | X204 | $CF_3$ |
| X208 | X206 | Ms |

TABLE 2-continued

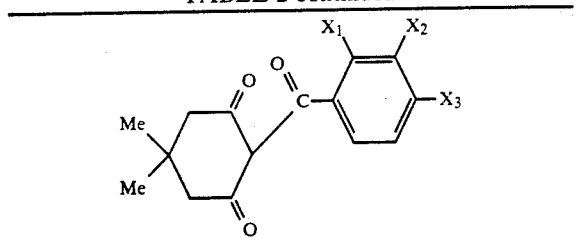

| $X_1$ | $X_2$ | $X_3$ |
|---|---|---|
| X208 | X206 | Cl |
| X208 | X206 | CF$_3$ |
| X208 | X212 | Ms |
| X208 | X212 | Cl |
| X208 | X212 | CF$_3$ |
| X208 | X213 | Ms |
| X208 | X213 | Cl |
| X208 | X213 | CF$_3$ |
| X208 | X214 | Ms |
| X208 | X214 | Cl |
| X208 | X214 | CF$_3$ |
| X208 | X216 | Ms |
| X208 | X216 | Cl |
| X208 | X216 | CF$_3$ |
| X208 | X217 | Ms |
| X208 | X217 | Cl |
| X208 | X217 | CF$_3$ |
| X208 | X218 | Ms |
| X208 | X218 | Cl |
| X208 | X218 | CF$_3$ |
| X208 | X220 | Ms |
| X208 | X220 | Cl |
| X208 | X220 | CF$_3$ |
| X208 | X222 | Ms |
| X208 | X222 | Cl |
| X208 | X222 | CF$_3$ |
| X208 | X226 | Ms |
| X208 | X226 | Cl |
| X208 | X226 | CF$_3$ |
| X208 | X227 | Ms |
| X208 | X227 | Cl |
| X208 | X227 | CF$_3$ |
| X209 | X201 | Ms |
| X209 | X201 | Cl |
| X209 | X201 | CF$_3$ |
| X209 | X202 | Ms |
| X209 | X202 | Cl |
| X209 | X202 | CF$_3$ |
| X209 | X205 | Ms |
| X209 | X205 | Cl |
| X209 | X205 | CF$_3$ |
| X209 | X207 | Ms |
| X209 | X207 | Cl |
| X209 | X207 | CF$_3$ |
| X209 | X208 | Ms |
| X209 | X208 | Cl |
| X209 | X208 | CF$_3$ |
| X209 | X209 | Ms |
| X209 | X209 | Cl |
| X209 | X209 | CF$_3$ |
| X209 | X210 | Ms |
| X209 | X210 | Cl |
| X209 | X210 | CF$_3$ |
| X209 | X203 | Ms |
| X209 | X203 | Cl |
| X209 | X203 | CF$_3$ |
| X209 | X204 | Ms |
| X209 | X204 | Cl |
| X209 | X204 | CF$_3$ |
| X209 | X206 | Ms |
| X209 | X206 | Cl |
| X209 | X206 | CF$_3$ |
| X209 | X212 | Ms |
| X209 | X212 | Cl |
| X209 | X212 | CF$_3$ |
| X209 | X213 | Ms |
| X209 | X213 | Cl |
| X209 | X213 | CF$_3$ |
| X209 | X214 | Ms |

TABLE 2-continued

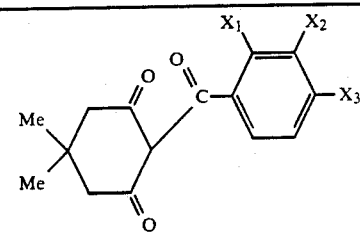

| $X_1$ | $X_2$ | $X_3$ |
|---|---|---|
| X209 | X214 | Cl |
| X209 | X214 | CF$_3$ |
| X209 | X216 | Ms |
| X209 | X216 | Cl |
| X209 | X216 | CF$_3$ |
| X209 | X217 | Ms |
| X209 | X217 | Cl |
| X209 | X217 | CF$_3$ |
| X209 | X218 | Ms |
| X209 | X218 | Cl |
| X209 | X218 | CF$_3$ |
| X209 | X220 | Ms |
| X209 | X220 | Cl |
| X209 | X220 | CF$_3$ |
| X209 | X222 | Ms |
| X209 | X222 | Cl |
| X209 | X222 | CF$_3$ |
| X209 | X226 | Ms |
| X209 | X226 | Cl |
| X209 | X226 | CF$_3$ |
| X209 | X227 | Ms |
| X209 | X227 | Cl |
| X209 | X227 | CF$_3$ |
| X210 | X201 | Ms |
| X210 | X201 | Cl |
| X210 | X201 | CF$_3$ |
| X210 | X202 | Ms |
| X210 | X202 | Cl |
| X210 | X202 | CF$_3$ |
| X210 | X205 | Ms |
| X210 | X205 | Cl |
| X210 | X205 | CF$_3$ |
| X210 | X207 | Ms |
| X210 | X207 | Cl |
| X210 | X207 | CF$_3$ |
| X210 | X208 | Ms |
| X210 | X208 | Cl |
| X210 | X208 | CF$_3$ |
| X210 | X209 | Ms |
| X210 | X209 | Cl |
| X210 | X209 | CF$_3$ |
| X210 | X210 | Ms |
| X210 | X210 | Cl |
| X210 | X210 | CF$_3$ |
| X210 | X203 | Ms |
| X210 | X203 | Cl |
| X210 | X203 | CF$_3$ |
| X210 | X204 | Ms |
| X210 | X204 | Cl |
| X210 | X204 | CF$_3$ |
| X210 | X206 | Ms |
| X210 | X206 | Cl |
| X210 | X206 | CF$_3$ |
| X210 | X212 | Ms |
| X210 | X212 | Cl |
| X210 | X212 | CF$_3$ |
| X210 | X213 | Ms |
| X210 | X213 | Cl |
| X210 | X213 | CF$_3$ |
| X210 | X214 | Ms |
| X210 | X214 | Cl |
| X210 | X214 | CF$_3$ |
| X210 | X216 | Ms |
| X210 | X216 | Cl |
| X210 | X216 | CF$_3$ |
| X210 | X217 | Ms |
| X210 | X217 | Cl |
| X210 | X217 | CF$_3$ |
| X210 | X218 | Ms |

TABLE 2-continued

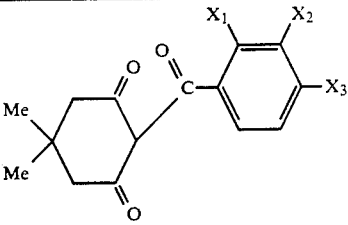

| $X_1$ | $X_2$ | $X_3$ |
|---|---|---|
| X210 | X218 | Cl |
| X210 | X218 | $CF_3$ |
| X210 | X220 | Ms |
| X210 | X220 | Cl |
| X210 | X220 | $CF_3$ |
| X210 | X222 | Ms |
| X210 | X222 | Cl |
| X210 | X222 | $CF_3$ |
| X210 | X226 | Ms |
| X210 | X226 | Cl |
| X210 | X226 | $CF_3$ |
| X210 | X227 | Ms |
| X210 | X227 | Cl |
| X210 | X227 | $CF_3$ |
| Cl | X201 | $NO_2$ |
| Cl | X201 | MeO |
| Cl | X201 | CN |
| Cl | X201 | SMe |
| Cl | X201 | SOMe |
| Cl | X201 | $SO_2CF_3$ |
| Cl | X201 | Br |
| Cl | X201 | I |
| Cl | X201 | EtO |
| Cl | X202 | $NO_2$ |
| Cl | X202 | MeO |
| Cl | X202 | CN |
| Cl | X202 | SMe |
| Cl | X202 | SOMe |
| Cl | X202 | $SO_2CF_3$ |
| Cl | X202 | Br |
| Cl | X202 | I |
| Cl | X202 | EtO |
| Cl | X205 | $NO_2$ |
| Cl | X205 | MeO |
| Cl | X205 | CN |
| Cl | X205 | SMe |
| Cl | X205 | SOMe |
| Cl | X205 | $SO_2CF_3$ |
| Cl | X205 | Br |
| Cl | X205 | I |
| Cl | X205 | EtO |
| Cl | X207 | $NO_2$ |
| Cl | X207 | MeO |
| Cl | X207 | CN |
| Cl | X207 | SMe |
| Cl | X207 | SOMe |
| Cl | X207 | $SO_2CF_3$ |
| Cl | X207 | Br |
| Cl | X207 | I |
| Cl | X207 | EtO |
| Cl | X208 | $NO_2$ |
| Cl | X208 | MeO |
| Cl | X208 | CN |
| Cl | X208 | SMe |
| Cl | X208 | SOMe |
| Cl | X208 | $SO_2CF_3$ |
| Cl | X208 | Br |
| Cl | X208 | I |
| Cl | X208 | EtO |
| Cl | X209 | $NO_2$ |
| Cl | X209 | MeO |
| Cl | X209 | CN |
| Cl | X209 | SMe |
| Cl | X209 | SOMe |
| Cl | X209 | $SO_2CF_3$ |
| Cl | X209 | Br |
| Cl | X209 | I |
| Cl | X209 | EtO |
| Cl | X210 | $NO_2$ |

TABLE 2-continued

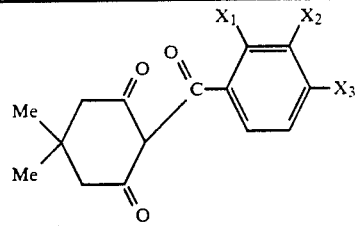

| $X_1$ | $X_2$ | $X_3$ |
|---|---|---|
| Cl | X210 | MeO |
| Cl | X210 | CN |
| Cl | X210 | SMe |
| Cl | X210 | SOMe |
| Cl | X210 | $SO_2CF_3$ |
| Cl | X210 | Br |
| Cl | X210 | I |
| Cl | X210 | EtO |
| Me | X201 | $NO_2$ |
| Me | X201 | MeO |
| Me | X201 | CN |
| Me | X201 | SMe |
| Me | X201 | SOMe |
| Me | X201 | $SO_2CF_3$ |
| Me | X201 | Br |
| Me | X201 | I |
| Me | X201 | EtO |
| Me | X202 | $NO_2$ |
| Me | X202 | MeO |
| Me | X202 | CN |
| Me | X202 | SMe |
| Me | X202 | SOMe |
| Me | X202 | $SO_2CF_3$ |
| Me | X202 | Br |
| Me | X202 | I |
| Me | X202 | EtO |
| Me | X205 | $NO_2$ |
| Me | X205 | MeO |
| Me | X205 | CN |
| Me | X205 | SMe |
| Me | X205 | SOMe |
| Me | X205 | $SO_2CF_3$ |
| Me | X205 | Br |
| Me | X205 | I |
| Me | X205 | EtO |
| Me | X207 | $NO_2$ |
| Me | X207 | MeO |
| Me | X207 | CN |
| Me | X207 | SMe |
| Me | X207 | SOMe |
| Me | X207 | $SO_2CF_3$ |
| Me | X207 | Br |
| Me | X207 | I |
| Me | X207 | EtO |
| Me | X208 | $NO_2$ |
| Me | X208 | MeO |
| Me | X208 | CN |
| Me | X208 | SMe |
| Me | X208 | SOMe |
| Me | X208 | $SO_2CF_3$ |
| Me | X208 | Br |
| Me | X208 | I |
| Me | X208 | EtO |
| Me | X209 | $NO_2$ |
| Me | X209 | MeO |
| Me | X209 | CN |
| Me | X209 | SMe |
| Me | X209 | SOMe |
| Me | X209 | $SO_2CF_3$ |
| Me | X209 | Br |
| Me | X209 | I |
| Me | X209 | EtO |
| Me | X210 | $NO_2$ |
| Me | X210 | MeO |
| Me | X210 | CN |
| Me | X210 | SMe |
| Me | X210 | SOMe |
| Me | X210 | $SO_2CF_3$ |
| Me | X210 | Br |

TABLE 2-continued

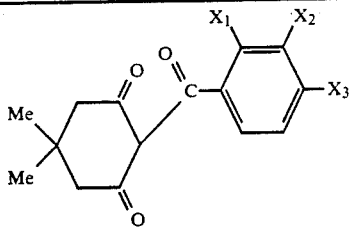

| X₁ | X₂ | X₃ |
|---|---|---|
| Me | X210 | I |
| Me | X210 | EtO |

TABLE 3

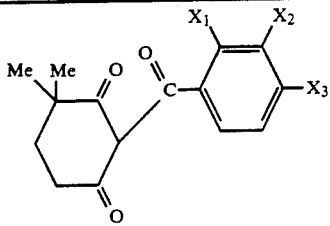

| X₁ | X₂ | X₃ |
|---|---|---|
| Cl | X201 | Ms |
| Cl | X201 | Cl |
| Cl | X202 | Ms |
| Cl | X202 | Cl |
| Cl | X205 | Ms |
| Cl | X205 | Cl |
| Cl | X207 | Ms |
| Cl | X207 | Cl |
| Cl | X208 | Ms |
| Cl | X208 | Cl |
| Cl | X209 | Ms |
| Cl | X209 | Cl |
| Cl | X210 | Ms |
| Cl | X210 | Cl |
| Cl | X201 | CF₃ |
| Cl | X202 | CF₃ |
| Cl | X205 | CF₃ |
| Cl | X207 | CF₃ |
| Cl | X208 | CF₃ |
| Cl | X209 | CF₃ |
| Cl | X210 | CF₃ |
| Me | X201 | Ms |
| Me | X201 | Cl |
| Me | X201 | CF₃ |
| Me | X202 | Ms |
| Me | X202 | Cl |
| Me | X202 | CF₃ |
| Me | X205 | Ms |
| Me | X205 | Cl |
| Me | X205 | CF₃ |
| Me | X207 | Ms |
| Me | X207 | Cl |
| Me | X207 | CF₃ |
| Me | X208 | Ms |
| Me | X208 | Cl |
| Me | X208 | CF₃ |
| Me | X209 | Ms |
| Me | X209 | Cl |
| Me | X209 | CF₃ |
| Me | X210 | Ms |
| Me | X210 | Cl |
| Me | X210 | CF₃ |
| Cl | X203 | Ms |
| Cl | X203 | Cl |
| Cl | X203 | CF₃ |
| Cl | X204 | Ms |
| Cl | X204 | Cl |
| Cl | X204 | CF₃ |
| Cl | X206 | Ms |
| Cl | X206 | Cl |

TABLE 3-continued

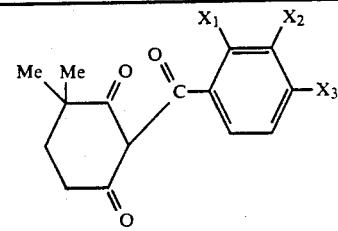

| X₁ | X₂ | X₃ |
|---|---|---|
| Cl | X206 | CF₃ |
| Cl | X212 | Ms |
| Cl | X212 | Cl |
| Cl | X212 | CF₃ |
| Cl | X213 | Ms |
| Cl | X213 | Cl |
| Cl | X213 | CF₃ |
| Cl | X214 | Ms |
| Cl | X214 | Cl |
| Cl | X214 | CF₃ |
| Cl | X216 | Ms |
| Cl | X216 | Cl |
| Cl | X216 | CF₃ |
| Cl | X217 | Ms |
| Cl | X217 | Cl |
| Cl | X217 | CF₃ |
| Cl | X218 | Ms |
| Cl | X218 | Cl |
| Cl | X218 | CF₃ |
| Cl | X220 | Ms |
| Cl | X220 | Cl |
| Cl | X220 | CF₃ |
| Cl | X222 | Ms |
| Cl | X222 | Cl |
| Cl | X222 | CF₃ |
| Cl | X226 | Ms |
| Cl | X226 | Cl |
| Cl | X226 | CF₃ |
| Cl | X227 | Ms |
| Cl | X227 | Cl |
| Cl | X227 | CF₃ |
| Me | X203 | Ms |
| Me | X203 | Cl |
| Me | X203 | CF₃ |
| Me | X204 | Ms |
| Me | X204 | Cl |
| Me | X204 | CF₃ |
| Me | X206 | Ms |
| Me | X206 | Cl |
| Me | X206 | CF₃ |
| Me | X212 | Ms |
| Me | X212 | Cl |
| Me | X212 | CF₃ |
| Me | X213 | Ms |
| Me | X213 | Cl |
| Me | X213 | CF₃ |
| Me | X214 | Ms |
| Me | X214 | Cl |
| Me | X214 | CF₃ |
| Me | X216 | Ms |
| Me | X216 | Cl |
| Me | X216 | CF₃ |
| Me | X217 | Ms |
| Me | X217 | Cl |
| Me | X217 | CF₃ |
| Me | X218 | Ms |
| Me | X218 | Cl |
| Me | X218 | CF₃ |
| Me | X220 | Ms |
| Me | X220 | Cl |
| Me | X220 | CF₃ |
| Me | X222 | Ms |
| Me | X222 | Cl |
| Me | X222 | CF₃ |
| Me | X226 | Ms |
| Me | X226 | Cl |
| Me | X226 | CF₃ |
| Me | X227 | Ms |
| Me | X227 | Cl |

TABLE 3-continued

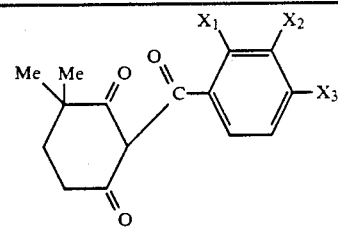

| X₁ | X₂ | X₃ |
|---|---|---|
| Me | X227 | CF₃ |
| Cl | X211 | Ms |
| Cl | X211 | Cl |
| Cl | X211 | CF₃ |
| Cl | X215 | Ms |
| Cl | X215 | Cl |
| Cl | X215 | CF₃ |
| Cl | X219 | Ms |
| Cl | X219 | Cl |
| Cl | X219 | CF₃ |
| Cl | X221 | Ms |
| Cl | X221 | Cl |
| Cl | X221 | CF₃ |
| Cl | X223 | Ms |
| Cl | X223 | Cl |
| Cl | X223 | CF₃ |
| Cl | X224 | Ms |
| Cl | X224 | Cl |
| Cl | X224 | CF₃ |
| Cl | X225 | Ms |
| Cl | X225 | Cl |
| Cl | X225 | CF₃ |
| Me | X211 | Ms |
| Me | X211 | Cl |
| Me | X211 | CF₃ |
| Me | X215 | Ms |
| Me | X215 | Cl |
| Me | X215 | CF₃ |
| Me | X219 | Ms |
| Me | X219 | Cl |
| Me | X219 | CF₃ |
| Me | X221 | Ms |
| Me | X221 | Cl |
| Me | X221 | CF₃ |
| Me | X223 | Ms |
| Me | X223 | Cl |
| Me | X223 | CF₃ |
| Me | X224 | Ms |
| Me | X224 | Cl |
| Me | X224 | CF₃ |
| Me | X225 | Ms |
| Me | X225 | Cl |
| Me | X225 | CF₃ |
| NO₂ | X201 | Ms |
| NO₂ | X201 | Cl |
| NO₂ | X201 | CF₃ |
| NO₂ | X202 | Ms |
| NO₂ | X202 | Cl |
| NO₂ | X202 | CF₃ |
| NO₂ | X205 | Ms |
| NO₂ | X205 | Cl |
| NO₂ | X205 | CF₃ |
| NO₂ | X207 | Ms |
| NO₂ | X207 | Cl |
| NO₂ | X207 | CF₃ |
| NO₂ | X208 | Ms |
| NO₂ | X208 | Cl |
| NO₂ | X208 | CF₃ |
| NO₂ | X209 | Ms |
| NO₂ | X209 | Cl |
| NO₂ | X209 | CF₃ |
| NO₂ | X210 | Ms |
| NO₂ | X210 | Cl |
| NO₂ | X210 | CF₃ |
| Et | X201 | Ms |
| Et | X201 | Cl |
| Et | X201 | CF₃ |
| Et | X202 | Ms |
| Et | X202 | Cl |
| Et | X202 | CF₃ |
| Et | X205 | Ms |
| Et | X205 | Cl |
| Et | X205 | CF₃ |
| Et | X207 | Ms |
| Et | X207 | Cl |
| Et | X207 | CF₃ |
| Et | X208 | Ms |
| Et | X208 | Cl |
| Et | X208 | CF₃ |
| Et | X209 | Ms |
| Et | X209 | Cl |
| Et | X209 | CF₃ |
| Et | X210 | Ms |
| Et | X210 | Cl |
| Et | X210 | CF₃ |
| i-Pr | X201 | Ms |
| i-Pr | X201 | Cl |
| i-Pr | X201 | CF₃ |
| i-Pr | X202 | Ms |
| i-Pr | X202 | Cl |
| i-Pr | X202 | CF₃ |
| i-Pr | X205 | Ms |
| i-Pr | X205 | Cl |
| i-Pr | X205 | CF₃ |
| i-Pr | X207 | Ms |
| i-Pr | X207 | Cl |
| i-Pr | X207 | CF₃ |
| i-Pr | X208 | Ms |
| i-Pr | X208 | Cl |
| i-Pr | X208 | CF₃ |
| i-Pr | X209 | Ms |
| i-Pr | X209 | Cl |
| i-Pr | X209 | CF₃ |
| i-Pr | X210 | Ms |
| i-Pr | X210 | Cl |
| i-Pr | X210 | CF₃ |
| n-Pr | X201 | Ms |
| n-Pr | X201 | Cl |
| n-Pr | X201 | CF₃ |
| n-Pr | X202 | Ms |
| n-Pr | X202 | Cl |
| n-Pr | X202 | CF₃ |
| n-Pr | X205 | Ms |
| n-Pr | X205 | Cl |
| n-Pr | X205 | CF₃ |
| n-Pr | X207 | Ms |
| n-Pr | X207 | Cl |
| n-Pr | X207 | CF₃ |
| n-Pr | X208 | Ms |
| n-Pr | X208 | Cl |
| n-Pr | X208 | CF₃ |
| n-Pr | X209 | Ms |
| n-Pr | X209 | Cl |
| n-Pr | X209 | CF₃ |
| n-Pr | X210 | Ms |
| n-Pr | X210 | Cl |
| n-Pr | X210 | CF₃ |
| CN | X201 | Ms |
| CN | X201 | Cl |
| CN | X201 | CF₃ |
| CN | X202 | Ms |
| CN | X202 | Cl |
| CN | X202 | CF₃ |
| CN | X205 | Ms |
| CN | X205 | Cl |
| CN | X205 | CF₃ |
| CN | X207 | Ms |
| CN | X207 | Cl |

TABLE 3-continued

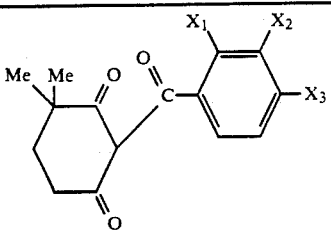
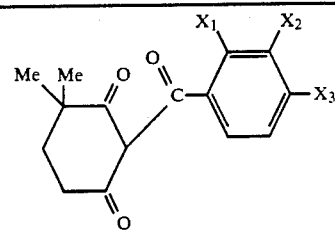

| $X_1$ | $X_2$ | $X_3$ | $X_1$ | $X_2$ | $X_3$ |
|---|---|---|---|---|---|
| CN | X207 | $CF_3$ | Br | X209 | $CF_3$ |
| CN | X208 | Ms | Br | X210 | Ms |
| CN | X208 | Cl | Br | X210 | Cl |
| CN | X208 | $CF_3$ | Br | X210 | $CF_3$ |
| CN | X209 | Ms | I | X201 | Ms |
| CN | X209 | Cl | I | X201 | Cl |
| CN | X209 | $CF_3$ | I | X201 | $CF_3$ |
| CN | X210 | Ms | I | X202 | Ms |
| CN | X210 | Cl | I | X202 | Cl |
| CN | X210 | $CF_3$ | I | X202 | $CF_3$ |
| $CF_3$ | X201 | Ms | I | X205 | Ms |
| $CF_3$ | X201 | Cl | I | X205 | Cl |
| $CF_3$ | X201 | $CF_3$ | I | X205 | $CF_3$ |
| $CF_3$ | X202 | Ms | I | X207 | Ms |
| $CF_3$ | X202 | Cl | I | X207 | Cl |
| $CF_3$ | X202 | $CF_3$ | I | X207 | $CF_3$ |
| $CF_3$ | X205 | Ms | I | X208 | Ms |
| $CF_3$ | X205 | Cl | I | X208 | Cl |
| $CF_3$ | X205 | $CF_3$ | I | X208 | $CF_3$ |
| $CF_3$ | X207 | Ms | I | X209 | Ms |
| $CF_3$ | X207 | Cl | I | X209 | Cl |
| $CF_3$ | X207 | $CF_3$ | I | X209 | $CF_3$ |
| $CF_3$ | X208 | Ms | I | X210 | Ms |
| $CF_3$ | X208 | Cl | I | X210 | Cl |
| $CF_3$ | X208 | $CF_3$ | I | X210 | $CF_3$ |
| $CF_3$ | X209 | Ms | MeO | X201 | Ms |
| $CF_3$ | X209 | Cl | MeO | X201 | Cl |
| $CF_3$ | X209 | $CF_3$ | MeO | X201 | $CF_3$ |
| $CF_3$ | X210 | Ms | MeO | X202 | Ms |
| $CF_3$ | X210 | Cl | MeO | X202 | Cl |
| $CF_3$ | X210 | $CF_3$ | MeO | X202 | $CF_3$ |
| F | X201 | Ms | MeO | X205 | Ms |
| F | X201 | Cl | MeO | X205 | Cl |
| F | X201 | $CF_3$ | MeO | X205 | $CF_3$ |
| F | X202 | Ms | MeO | X207 | Ms |
| F | X202 | Cl | MeO | X207 | Cl |
| F | X202 | $CF_3$ | MeO | X207 | $CF_3$ |
| F | X205 | Ms | MeO | X208 | Ms |
| F | X205 | Cl | MeO | X208 | Cl |
| F | X205 | $CF_3$ | MeO | X208 | $CF_3$ |
| F | X207 | Ms | MeO | X209 | Ms |
| F | X207 | Cl | MeO | X209 | Cl |
| F | X207 | $CF_3$ | MeO | X209 | $CF_3$ |
| F | X208 | Ms | MeO | X210 | Ms |
| F | X208 | Cl | MeO | X210 | Cl |
| F | X208 | $CF_3$ | MeO | X210 | $CF_3$ |
| F | X209 | Ms | EtO | X201 | Ms |
| F | X209 | Cl | EtO | X201 | Cl |
| F | X209 | $CF_3$ | EtO | X201 | $CF_3$ |
| F | X210 | Ms | EtO | X202 | Ms |
| F | X210 | Cl | EtO | X202 | Cl |
| F | X210 | $CF_3$ | EtO | X202 | $CF_3$ |
| Br | X201 | Ms | EtO | X205 | Ms |
| Br | X201 | Cl | EtO | X205 | Cl |
| Br | X201 | $CF_3$ | EtO | X205 | $CF_3$ |
| Br | X202 | Ms | EtO | X207 | Ms |
| Br | X202 | Cl | EtO | X207 | Cl |
| Br | X202 | $CF_3$ | EtO | X207 | $CF_3$ |
| Br | X205 | Ms | EtO | X208 | Ms |
| Br | X205 | Cl | EtO | X208 | Cl |
| Br | X205 | $CF_3$ | EtO | X208 | $CF_3$ |
| Br | X207 | Ms | EtO | X209 | Ms |
| Br | X207 | Cl | EtO | X209 | Cl |
| Br | X207 | $CF_3$ | EtO | X209 | $CF_3$ |
| Br | X208 | Ms | EtO | X210 | Ms |
| Br | X208 | Cl | EtO | X210 | Cl |
| Br | X208 | $CF_3$ | EtO | X210 | $CF_3$ |
| Br | X209 | Ms | i-PrO | X201 | Ms |
| Br | X209 | Cl | i-PrO | X201 | Cl |

TABLE 3-continued

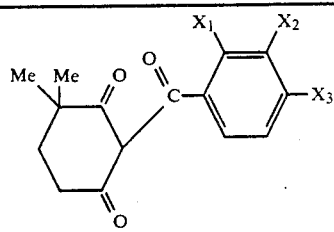

| $X_1$ | $X_2$ | $X_3$ |
|---|---|---|
| i-PrO | X201 | $CF_3$ |
| i-PrO | X202 | Ms |
| i-PrO | X202 | Cl |
| i-PrO | X202 | $CF_3$ |
| i-PrO | X205 | Ms |
| i-PrO | X205 | Cl |
| i-PrO | X205 | $CF_3$ |
| i-PrO | X207 | Ms |
| i-PrO | X207 | Cl |
| i-PrO | X207 | $CF_3$ |
| i-PrO | X208 | Ms |
| i-PrO | X208 | Cl |
| i-PrO | X208 | $CF_3$ |
| i-PrO | X209 | Ms |
| i-PrO | X209 | Cl |
| i-PrO | X209 | $CF_3$ |
| i-PrO | X210 | Ms |
| i-PrO | X210 | Cl |
| i-PrO | X210 | $CF_3$ |
| n-PrO | X201 | Ms |
| n-PrO | X201 | Cl |
| n-PrO | X201 | $CF_3$ |
| n-PrO | X202 | Ms |
| n-PrO | X202 | Cl |
| n-PrO | X202 | $CF_3$ |
| n-PrO | X205 | Ms |
| n-PrO | X205 | Cl |
| n-PrO | X205 | $CF_3$ |
| n-PrO | X207 | Ms |
| n-PrO | X207 | Cl |
| n-PrO | X207 | $CF_3$ |
| n-PrO | X208 | Ms |
| n-PrO | X208 | Cl |
| n-PrO | X208 | $CF_3$ |
| n-PrO | X209 | Ms |
| n-PrO | X209 | Cl |
| n-PrO | X209 | $CF_3$ |
| n-PrO | X210 | Ms |
| n-PrO | X210 | Cl |
| n-PrO | X210 | $CF_3$ |
| $CHF_2$ | X201 | Ms |
| $CHF_2$ | X201 | Cl |
| $CHF_2$ | X201 | $CF_3$ |
| $CHF_2$ | X202 | Ms |
| $CHF_2$ | X202 | Cl |
| $CHF_2$ | X202 | $CF_3$ |
| $CHF_2$ | X205 | Ms |
| $CHF_2$ | X205 | Cl |
| $CHF_2$ | X205 | $CF_3$ |
| $CHF_2$ | X207 | Ms |
| $CHF_2$ | X207 | Cl |
| $CHF_2$ | X207 | $CF_3$ |
| $CHF_2$ | X208 | Ms |
| $CHF_2$ | X208 | Cl |
| $CHF_2$ | X208 | $CF_3$ |
| $CHF_2$ | X209 | Ms |
| $CHF_2$ | X209 | Cl |
| $CHF_2$ | X209 | $CF_3$ |
| $CHF_2$ | X210 | Ms |
| $CHF_2$ | X210 | Cl |
| $CHF_2$ | X210 | $CF_3$ |
| $CH_2CF_3$ | X201 | Ms |
| $CH_2CF_3$ | X201 | Cl |
| $CH_2CF_3$ | X201 | $CF_3$ |
| $CH_2CF_3$ | X202 | Ms |
| $CH_2CF_3$ | X202 | Cl |
| $CH_2CF_3$ | X202 | $CF_3$ |
| $CH_2CF_3$ | X205 | Ms |
| $CH_2CF_3$ | X205 | Cl |

TABLE 3-continued

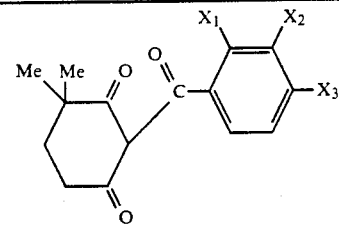

| $X_1$ | $X_2$ | $X_3$ |
|---|---|---|
| $CH_2CF_3$ | X205 | $CF_3$ |
| $CH_2CF_3$ | X207 | Ms |
| $CH_2CF_3$ | X207 | Cl |
| $CH_2CF_3$ | X207 | $CF_3$ |
| $CH_2CF_3$ | X208 | Ms |
| $CH_2CF_3$ | X208 | Cl |
| $CH_2CF_3$ | X208 | $CF_3$ |
| $CH_2CF_3$ | X209 | Ms |
| $CH_2CF_3$ | X209 | Cl |
| $CH_2CF_3$ | X209 | $CF_3$ |
| $CH_2CF_3$ | X210 | Ms |
| $CH_2CF_3$ | X210 | Cl |
| $CH_2CF_3$ | X210 | $CF_3$ |
| X201 | X201 | Ms |
| X201 | X201 | Cl |
| X201 | X201 | $CF_3$ |
| X201 | X202 | Ms |
| X201 | X202 | Cl |
| X201 | X202 | $CF_3$ |
| X201 | X205 | Ms |
| X201 | X205 | Cl |
| X201 | X205 | $CF_3$ |
| X201 | X207 | Ms |
| X201 | X207 | Cl |
| X201 | X207 | $CF_3$ |
| X201 | X208 | Ms |
| X201 | X208 | Cl |
| X201 | X208 | $CF_3$ |
| X201 | X209 | Ms |
| X201 | X209 | Cl |
| X201 | X209 | $CF_3$ |
| X201 | X210 | Ms |
| X201 | X210 | Cl |
| X201 | X210 | $CF_3$ |
| X201 | X203 | Ms |
| X201 | X203 | Cl |
| X201 | X203 | $CF_3$ |
| X201 | X204 | Ms |
| X201 | X204 | Cl |
| X201 | X204 | $CF_3$ |
| X201 | X206 | Ms |
| X201 | X206 | Cl |
| X201 | X206 | $CF_3$ |
| X201 | X212 | Ms |
| X201 | X212 | Cl |
| X201 | X212 | $CF_3$ |
| X201 | X213 | Ms |
| X201 | X213 | Cl |
| X201 | X213 | $CF_3$ |
| X201 | X214 | Ms |
| X201 | X214 | Cl |
| X201 | X214 | $CF_3$ |
| X201 | X216 | Ms |
| X201 | X216 | Cl |
| X201 | X216 | $CF_3$ |
| X201 | X217 | Ms |
| X201 | X217 | Cl |
| X201 | X217 | $CF_3$ |
| X201 | X218 | Ms |
| X201 | X218 | Cl |
| X201 | X218 | $CF_3$ |
| X201 | X220 | Ms |
| X201 | X220 | Cl |
| X201 | X220 | $CF_3$ |
| X201 | X222 | Ms |
| X201 | X222 | Cl |
| X201 | X222 | $CF_3$ |
| X201 | X226 | Ms |
| X201 | X226 | Cl |

TABLE 3-continued

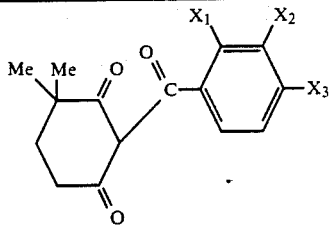

| $X_1$ | $X_2$ | $X_3$ |
|---|---|---|
| X201 | X226 | $CF_3$ |
| X201 | X227 | Ms |
| X201 | X227 | Cl |
| X201 | X227 | $CF_3$ |
| X201 | X228 | Ms |
| X201 | X228 | Cl |
| X201 | X228 | $CF_3$ |
| X201 | X229 | Ms |
| X201 | X229 | Cl |
| X201 | X229 | $CF_3$ |
| X201 | X230 | Ms |
| X201 | X230 | Cl |
| X201 | X230 | $CF_3$ |
| X201 | X231 | Ms |
| X201 | X231 | Cl |
| X201 | X231 | $CF_3$ |
| X201 | X232 | Ms |
| X201 | X232 | Cl |
| X201 | X232 | $CF_3$ |
| X201 | X233 | Ms |
| X201 | X233 | Cl |
| X201 | X233 | $CF_3$ |
| X201 | X234 | Ms |
| X201 | X234 | Cl |
| X201 | X234 | $CF_3$ |
| X201 | X235 | Ms |
| X201 | X235 | Cl |
| X201 | X235 | $CF_3$ |
| X202 | X201 | Ms |
| X202 | X201 | Cl |
| X202 | X201 | $CF_3$ |
| X202 | X202 | Ms |
| X202 | X202 | Cl |
| X202 | X202 | $CF_3$ |
| X202 | X205 | Ms |
| X202 | X205 | Cl |
| X202 | X205 | $CF_3$ |
| X202 | X207 | Ms |
| X202 | X207 | Cl |
| X202 | X207 | $CF_3$ |
| X202 | X208 | Ms |
| X202 | X208 | Cl |
| X202 | X208 | $CF_3$ |
| X202 | X209 | Ms |
| X202 | X209 | Cl |
| X202 | X209 | $CF_3$ |
| X202 | X210 | Ms |
| X202 | X210 | Cl |
| X202 | X210 | $CF_3$ |
| X202 | X203 | Ms |
| X202 | X203 | Cl |
| X202 | X203 | $CF_3$ |
| X202 | X204 | Ms |
| X202 | X204 | Cl |
| X202 | X204 | $CF_3$ |
| X202 | X206 | Ms |
| X202 | X206 | Cl |
| X202 | X206 | $CF_3$ |
| X202 | X212 | Ms |
| X202 | X212 | Cl |
| X202 | X212 | $CF_3$ |
| X202 | X213 | Ms |
| X202 | X213 | Cl |
| X202 | X213 | $CF_3$ |
| X202 | X214 | Ms |
| X202 | X214 | Cl |
| X202 | X214 | $CF_3$ |
| X202 | X216 | Ms |
| X202 | X216 | Cl |

TABLE 3-continued

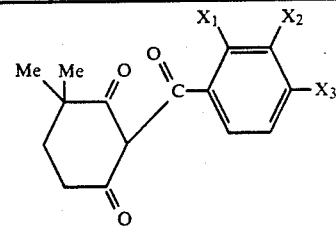

| $X_1$ | $X_2$ | $X_3$ |
|---|---|---|
| X202 | X216 | $CF_3$ |
| X202 | X217 | Ms |
| X202 | X217 | Cl |
| X202 | X217 | $CF_3$ |
| X202 | X218 | Ms |
| X202 | X218 | Cl |
| X202 | X218 | $CF_3$ |
| X202 | X220 | Ms |
| X202 | X220 | Cl |
| X202 | X220 | $CF_3$ |
| X202 | X222 | Ms |
| X202 | X222 | Cl |
| X202 | X222 | $CF_3$ |
| X202 | X226 | Ms |
| X202 | X226 | Cl |
| X202 | X226 | $CF_3$ |
| X202 | X227 | Ms |
| X202 | X227 | Cl |
| X202 | X227 | $CF_3$ |
| X202 | X228 | Ms |
| X202 | X228 | Cl |
| X202 | X228 | $CF_3$ |
| X202 | X229 | Ms |
| X202 | X229 | Cl |
| X202 | X229 | $CF_3$ |
| X202 | X230 | Ms |
| X202 | X230 | Cl |
| X202 | X230 | $CF_3$ |
| X202 | X231 | Ms |
| X202 | X231 | Cl |
| X202 | X231 | $CF_3$ |
| X202 | X232 | Ms |
| X202 | X232 | Cl |
| X202 | X232 | $CF_3$ |
| X202 | X233 | Ms |
| X202 | X233 | Cl |
| X202 | X233 | $CF_3$ |
| X202 | X234 | Ms |
| X202 | X234 | Cl |
| X202 | X234 | $CF_3$ |
| X202 | X235 | Ms |
| X202 | X235 | Cl |
| X202 | X235 | $CF_3$ |
| X205 | X201 | Ms |
| X205 | X201 | Cl |
| X205 | X201 | $CF_3$ |
| X205 | X202 | Ms |
| X205 | X202 | Cl |
| X205 | X202 | $CF_3$ |
| X205 | X205 | Ms |
| X205 | X205 | Cl |
| X205 | X205 | $CF_3$ |
| X205 | X207 | Ms |
| X205 | X207 | Cl |
| X205 | X207 | $CF_3$ |
| X205 | X208 | Ms |
| X205 | X208 | Cl |
| X205 | X208 | $CF_3$ |
| X205 | X209 | Ms |
| X205 | X209 | Cl |
| X205 | X209 | $CF_3$ |
| X205 | X210 | Ms |
| X205 | X210 | Cl |
| X205 | X210 | $CF_3$ |
| X205 | X203 | Ms |
| X205 | X203 | Cl |
| X205 | X203 | $CF_3$ |
| X205 | X204 | Ms |
| X205 | X204 | Cl |

TABLE 3-continued

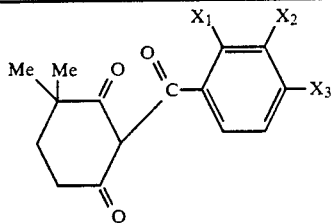

| $X_1$ | $X_2$ | $X_3$ |
|---|---|---|
| X205 | X204 | CF₃ |
| X205 | X206 | Ms |
| X205 | X206 | Cl |
| X205 | X206 | CF₃ |
| X205 | X212 | Ms |
| X205 | X212 | Cl |
| X205 | X212 | CF₃ |
| X205 | X213 | Ms |
| X205 | X213 | Cl |
| X205 | X213 | CF₃ |
| X205 | X214 | Ms |
| X205 | X214 | Cl |
| X205 | X214 | CF₃ |
| X205 | X216 | Ms |
| X205 | X216 | Cl |
| X205 | X216 | CF₃ |
| X205 | X217 | Ms |
| X205 | X217 | Cl |
| X205 | X217 | CF₃ |
| X205 | X218 | Ms |
| X205 | X218 | Cl |
| X205 | X218 | CF₃ |
| X205 | X220 | Ms |
| X205 | X220 | Cl |
| X205 | X220 | CF₃ |
| X205 | X222 | Ms |
| X205 | X222 | Cl |
| X205 | X222 | CF₃ |
| X205 | X226 | Ms |
| X205 | X226 | Cl |
| X205 | X226 | CF₃ |
| X205 | X227 | Ms |
| X205 | X227 | Cl |
| X205 | X227 | CF₃ |
| X205 | X228 | Ms |
| X205 | X228 | Cl |
| X205 | X228 | CF₃ |
| X205 | X229 | Ms |
| X205 | X229 | Cl |
| X205 | X229 | CF₃ |
| X205 | X230 | Ms |
| X205 | X230 | Cl |
| X205 | X230 | CF₃ |
| X205 | X231 | Ms |
| X205 | X231 | Cl |
| X205 | X231 | CF₃ |
| X205 | X232 | Ms |
| X205 | X232 | Cl |
| X205 | X232 | CF₃ |
| X205 | X233 | Ms |
| X205 | X233 | Cl |
| X205 | X233 | CF₃ |
| X205 | X234 | Ms |
| X205 | X234 | Cl |
| X205 | X234 | CF₃ |
| X207 | X201 | Ms |
| X207 | X201 | Cl |
| X207 | X201 | CF₃ |
| X207 | X202 | Ms |
| X207 | X202 | Cl |
| X207 | X202 | CF₃ |
| X207 | X205 | Ms |
| X207 | X205 | Cl |
| X207 | X205 | CF₃ |
| X207 | X207 | Ms |
| X207 | X207 | Cl |
| X207 | X207 | CF₃ |
| X207 | X208 | Ms |
| X207 | X208 | Cl |

TABLE 3-continued

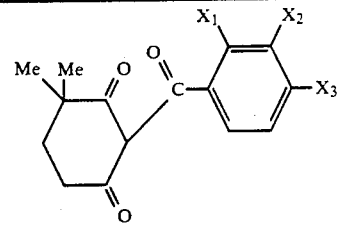

| $X_1$ | $X_2$ | $X_3$ |
|---|---|---|
| X207 | X208 | CF₃ |
| X207 | X209 | Ms |
| X207 | X209 | Cl |
| X207 | X209 | CF₃ |
| X207 | X210 | Ms |
| X207 | X210 | Cl |
| X207 | X210 | CF₃ |
| X207 | X203 | Ms |
| X207 | X203 | Cl |
| X207 | X203 | CF₃ |
| X207 | X204 | Ms |
| X207 | X204 | Cl |
| X207 | X204 | CF₃ |
| X207 | X206 | Ms |
| X207 | X206 | Cl |
| X207 | X206 | CF₃ |
| X207 | X212 | Ms |
| X207 | X212 | Cl |
| X207 | X212 | CF₃ |
| X207 | X213 | Ms |
| X207 | X213 | Cl |
| X207 | X213 | CF₃ |
| X207 | X214 | Ms |
| X207 | X214 | Cl |
| X207 | X214 | CF₃ |
| X207 | X216 | Ms |
| X207 | X216 | Cl |
| X207 | X216 | CF₃ |
| X207 | X217 | Ms |
| X207 | X217 | Cl |
| X207 | X217 | CF₃ |
| X207 | X218 | Ms |
| X207 | X218 | Cl |
| X207 | X218 | CF₃ |
| X207 | X220 | Ms |
| X207 | X220 | Cl |
| X207 | X220 | CF₃ |
| X207 | X222 | Ms |
| X207 | X222 | Cl |
| X207 | X222 | CF₃ |
| X207 | X226 | Ms |
| X207 | X226 | Cl |
| X207 | X226 | CF₃ |
| X207 | X227 | Ms |
| X207 | X227 | Cl |
| X207 | X227 | CF₃ |
| X208 | X201 | Ms |
| X208 | X201 | Cl |
| X208 | X201 | CF₃ |
| X208 | X202 | Ms |
| X208 | X202 | Cl |
| X208 | X202 | CF₃ |
| X208 | X205 | Ms |
| X208 | X205 | Cl |
| X208 | X205 | CF₃ |
| X208 | X207 | Ms |
| X208 | X207 | Cl |
| X208 | X207 | CF₃ |
| X208 | X208 | Ms |
| X208 | X208 | Cl |
| X208 | X208 | CF₃ |
| X208 | X209 | Ms |
| X208 | X209 | Cl |
| X208 | X209 | CF₃ |
| X208 | X210 | Ms |
| X208 | X210 | Cl |
| X208 | X210 | CF₃ |
| X208 | X203 | Ms |
| X208 | X203 | Cl |

TABLE 3-continued

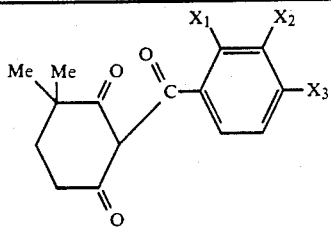
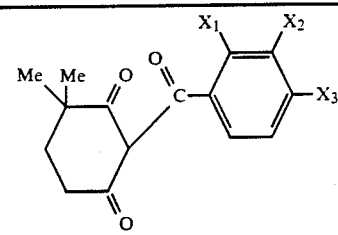

| $X_1$ | $X_2$ | $X_3$ | $X_1$ | $X_2$ | $X_3$ |
|---|---|---|---|---|---|
| X208 | X203 | CF$_3$ | X209 | X212 | CF$_3$ |
| X208 | X204 | Ms | X209 | X213 | Ms |
| X208 | X204 | Cl | X209 | X213 | Cl |
| X208 | X204 | CF$_3$ | X209 | X213 | CF$_3$ |
| X208 | X206 | Ms | X209 | X214 | Ms |
| X208 | X206 | Cl | X209 | X214 | Cl |
| X208 | X206 | CF$_3$ | X209 | X214 | CF$_3$ |
| X208 | X212 | Ms | X209 | X216 | Ms |
| X208 | X212 | Cl | X209 | X216 | Cl |
| X208 | X212 | CF$_3$ | X209 | X216 | CF$_3$ |
| X208 | X213 | Ms | X209 | X217 | Ms |
| X208 | X213 | Cl | X209 | X217 | Cl |
| X208 | X213 | CF$_3$ | X209 | X217 | CF$_3$ |
| X208 | X214 | Ms | X209 | X218 | Ms |
| X208 | X214 | Cl | X209 | X218 | Cl |
| X208 | X214 | CF$_3$ | X209 | X218 | CF$_3$ |
| X208 | X216 | Ms | X209 | X220 | Ms |
| X208 | X216 | Cl | X209 | X220 | Cl |
| X208 | X216 | CF$_3$ | X209 | X220 | CF$_3$ |
| X208 | X217 | Ms | X209 | X222 | Ms |
| X208 | X217 | Cl | X209 | X222 | Cl |
| X208 | X217 | CF$_3$ | X209 | X222 | CF$_3$ |
| X208 | X218 | Ms | X209 | X226 | Ms |
| X208 | X218 | Cl | X209 | X226 | Cl |
| X208 | X218 | CF$_3$ | X209 | X226 | CF$_3$ |
| X208 | X220 | Ms | X209 | X227 | Ms |
| X208 | X220 | Cl | X209 | X227 | Cl |
| X208 | X220 | CF$_3$ | X209 | X227 | CF$_3$ |
| X208 | X222 | Ms | X210 | X201 | Ms |
| X208 | X222 | Cl | X210 | X201 | Cl |
| X208 | X222 | CF$_3$ | X210 | X201 | CF$_3$ |
| X208 | X226 | Ms | X210 | X202 | Ms |
| X208 | X226 | Cl | X210 | X202 | Cl |
| X208 | X226 | CF$_3$ | X210 | X202 | CF$_3$ |
| X208 | X227 | Ms | X210 | X205 | Ms |
| X208 | X227 | Cl | X210 | X205 | Cl |
| X208 | X227 | CF$_3$ | X210 | X205 | CF$_3$ |
| X209 | X201 | Ms | X210 | X207 | Ms |
| X209 | X201 | Cl | X210 | X207 | Cl |
| X209 | X201 | CF$_3$ | X210 | X207 | CF$_3$ |
| X209 | X202 | Ms | X210 | X208 | Ms |
| X209 | X202 | Cl | X210 | X208 | Cl |
| X209 | X202 | CF$_3$ | X210 | X208 | CF$_3$ |
| X209 | X205 | Ms | X210 | X209 | Ms |
| X209 | X205 | Cl | X210 | X209 | Cl |
| X209 | X205 | CF$_3$ | X210 | X209 | CF$_3$ |
| X209 | X207 | Ms | X210 | X210 | Ms |
| X209 | X207 | Cl | X210 | X210 | Cl |
| X209 | X207 | CF$_3$ | X210 | X210 | CF$_3$ |
| X209 | X208 | Ms | X210 | X203 | Ms |
| X209 | X208 | Cl | X210 | X203 | Cl |
| X209 | X208 | CF$_3$ | X210 | X203 | CF$_3$ |
| X209 | X209 | Ms | X210 | X204 | Ms |
| X209 | X209 | Cl | X210 | X204 | Cl |
| X209 | X209 | CF$_3$ | X210 | X204 | CF$_3$ |
| X209 | X210 | Ms | X210 | X206 | Ms |
| X209 | X210 | Cl | X210 | X206 | Cl |
| X209 | X210 | CF$_3$ | X210 | X206 | CF$_3$ |
| X209 | X203 | Ms | X210 | X212 | Ms |
| X209 | X203 | Cl | X210 | X212 | Cl |
| X209 | X203 | CF$_3$ | X210 | X212 | CF$_3$ |
| X209 | X204 | Ms | X210 | X213 | Ms |
| X209 | X204 | Cl | X210 | X213 | Cl |
| X209 | X204 | CF$_3$ | X210 | X213 | CF$_3$ |
| X209 | X206 | Ms | X210 | X214 | Ms |
| X209 | X206 | Cl | X210 | X214 | Cl |
| X209 | X206 | CF$_3$ | X210 | X214 | CF$_3$ |
| X209 | X212 | Ms | X210 | X216 | Ms |
| X209 | X212 | Cl | X210 | X216 | Cl |

TABLE 3-continued

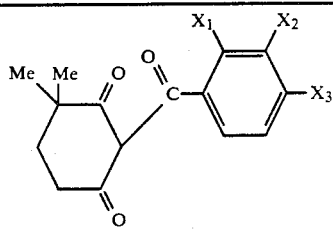

| $X_1$ | $X_2$ | $X_3$ |
|---|---|---|
| X210 | X216 | $CF_3$ |
| X210 | X217 | Ms |
| X210 | X217 | Cl |
| X210 | X217 | $CF_3$ |
| X210 | X218 | Ms |
| X210 | X218 | Cl |
| X210 | X218 | $CF_3$ |
| X210 | X220 | Ms |
| X210 | X220 | Cl |
| X210 | X220 | $CF_3$ |
| X210 | X222 | Ms |
| X210 | X222 | Cl |
| X210 | X222 | $CF_3$ |
| X210 | X226 | Ms |
| X210 | X226 | Cl |
| X210 | X226 | $CF_3$ |
| X210 | X227 | Ms |
| X210 | X227 | Cl |
| X210 | X227 | $CF_3$ |
| Cl | X201 | $NO_2$ |
| Cl | X201 | MeO |
| Cl | X201 | CN |
| Cl | X201 | SMe |
| Cl | X201 | SOMe |
| Cl | X201 | $SO_2CF_3$ |
| Cl | X201 | Br |
| Cl | X201 | I |
| Cl | X201 | EtO |
| Cl | X202 | $NO_2$ |
| Cl | X202 | MeO |
| Cl | X202 | CN |
| Cl | X202 | SMe |
| Cl | X202 | SOMe |
| Cl | X202 | $SO_2CF_3$ |
| Cl | X202 | Br |
| Cl | X202 | I |
| Cl | X202 | EtO |
| Cl | X205 | $NO_2$ |
| Cl | X205 | MeO |
| Cl | X205 | CN |
| Cl | X205 | SMe |
| Cl | X205 | SOMe |
| Cl | X205 | $SO_2CF_3$ |
| Cl | X205 | Br |
| Cl | X205 | I |
| Cl | X205 | EtO |
| Cl | X207 | $NO_2$ |
| Cl | X207 | MeO |
| Cl | X207 | CN |
| Cl | X207 | SMe |
| Cl | X207 | SOMe |
| Cl | X207 | $SO_2CF_3$ |
| Cl | X207 | Br |
| Cl | X207 | I |
| Cl | X207 | EtO |
| Cl | X208 | $NO_2$ |
| Cl | X208 | MeO |
| Cl | X208 | CN |
| Cl | X208 | SMe |
| Cl | X208 | SOMe |
| Cl | X208 | $SO_2CF_3$ |
| Cl | X208 | Br |
| Cl | X208 | I |
| Cl | X208 | EtO |
| Cl | X209 | $NO_2$ |
| Cl | X209 | MeO |
| Cl | X209 | CN |
| Cl | X209 | SMe |
| Cl | X209 | SOMe |

TABLE 3-continued

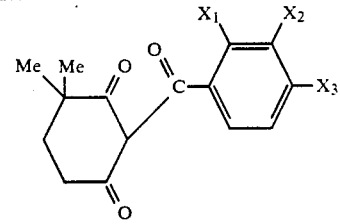

| $X_1$ | $X_2$ | $X_3$ |
|---|---|---|
| Cl | X209 | $SO_2CF_3$ |
| Cl | X209 | Br |
| Cl | X209 | I |
| Cl | X209 | EtO |
| Cl | X210 | $NO_2$ |
| Cl | X210 | MeO |
| Cl | X210 | CN |
| Cl | X210 | SMe |
| Cl | X210 | SOMe |
| Cl | X210 | $SO_2CF_3$ |
| Cl | X210 | Br |
| Cl | X210 | I |
| Cl | X210 | EtO |
| Me | X201 | $NO_2$ |
| Me | X201 | MeO |
| Me | X201 | CN |
| Me | X201 | SMe |
| Me | X201 | SOMe |
| Me | X201 | $SO_2CF_3$ |
| Me | X201 | Br |
| Me | X201 | I |
| Me | X201 | EtO |
| Me | X202 | $NO_2$ |
| Me | X202 | MeO |
| Me | X202 | CN |
| Me | X202 | SMe |
| Me | X202 | SOMe |
| Me | X202 | $SO_2CF_3$ |
| Me | X202 | Br |
| Me | X202 | I |
| Me | X202 | EtO |
| Me | X205 | $NO_2$ |
| Me | X205 | MeO |
| Me | X205 | CN |
| Me | X205 | SMe |
| Me | X205 | SOMe |
| Me | X205 | $SO_2CF_3$ |
| Me | X205 | Br |
| Me | X205 | I |
| Me | X205 | EtO |
| Me | X207 | $NO_2$ |
| Me | X207 | MeO |
| Me | X207 | CN |
| Me | X207 | SMe |
| Me | X207 | SOMe |
| Me | X207 | $SO_2CF_3$ |
| Me | X207 | Br |
| Me | X207 | I |
| Me | X207 | EtO |
| Me | X208 | $NO_2$ |
| Me | X208 | MeO |
| Me | X208 | CN |
| Me | X208 | SMe |
| Me | X208 | SOMe |
| Me | X208 | $SO_2CF_3$ |
| Me | X208 | Br |
| Me | X208 | I |
| Me | X208 | EtO |
| Me | X209 | $NO_2$ |
| Me | X209 | MeO |
| Me | X209 | CN |
| Me | X209 | SMe |
| Me | X209 | SOMe |
| Me | X209 | $SO_2CF_3$ |
| Me | X209 | Br |
| Me | X209 | I |
| Me | X209 | EtO |
| Me | X210 | $NO_2$ |
| Me | X210 | MeO |

TABLE 3-continued

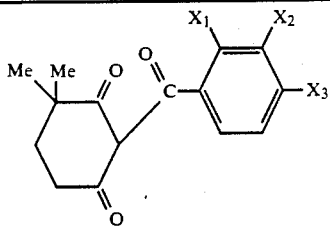

| $X_1$ | $X_2$ | $X_3$ |
|---|---|---|
| Me | X210 | CN |
| Me | X210 | SMe |
| Me | X210 | SOMe |
| Me | X210 | $SO_2CF_3$ |
| Me | X210 | Br |
| Me | X210 | I |
| Me | X210 | EtO |

TABLE 4

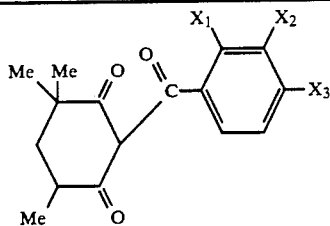

| $X_1$ | $X_2$ | $X_3$ |
|---|---|---|
| Cl | X201 | Ms |
| Cl | X201 | Cl |
| Cl | X202 | Ms |
| Cl | X202 | Cl |
| Cl | X205 | Ms |
| Cl | X205 | Cl |
| Cl | X207 | Ms |
| Cl | X207 | Cl |
| Cl | X208 | Ms |
| Cl | X208 | Cl |
| Cl | X209 | Ms |
| Cl | X209 | Cl |
| Cl | X210 | Ms |
| Cl | X210 | Cl |
| Cl | X201 | $CF_3$ |
| Cl | X202 | $CF_3$ |
| Cl | X205 | $CF_3$ |
| Cl | X207 | $CF_3$ |
| Cl | X208 | $CF_3$ |
| Cl | X209 | $CF_3$ |
| Cl | X210 | $CF_3$ |
| Me | X201 | Ms |
| Me | X201 | Cl |
| Me | X201 | $CF_3$ |
| Me | X202 | Ms |
| Me | X202 | Cl |
| Me | X202 | $CF_3$ |
| Me | X205 | Ms |
| Me | X205 | Cl |
| Me | X205 | $CF_3$ |
| Me | X207 | Ms |
| Me | X207 | Cl |
| Me | X207 | $CF_3$ |
| Me | X208 | Ms |
| Me | X208 | Cl |
| Me | X208 | $CF_3$ |
| Me | X209 | Ms |
| Me | X209 | Cl |
| Me | X209 | $CF_3$ |
| Me | X210 | Ms |
| Me | X210 | Cl |
| Me | X210 | $CF_3$ |
| Cl | X203 | Ms |
| Cl | X203 | Cl |
| Cl | X203 | $CF_3$ |

TABLE 4-continued

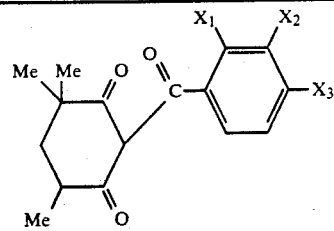

| $X_1$ | $X_2$ | $X_3$ |
|---|---|---|
| Cl | X204 | Ms |
| Cl | X204 | Cl |
| Cl | X204 | $CF_3$ |
| Cl | X206 | Ms |
| Cl | X206 | Cl |
| Cl | X206 | $CF_3$ |
| Cl | X212 | Ms |
| Cl | X212 | Cl |
| Cl | X212 | $CF_3$ |
| Cl | X213 | Ms |
| Cl | X213 | Cl |
| Cl | X213 | $CF_3$ |
| Cl | X214 | Ms |
| Cl | X214 | Cl |
| Cl | X214 | $CF_3$ |
| Cl | X216 | Ms |
| Cl | X216 | Cl |
| Cl | X216 | $CF_3$ |
| Cl | X217 | Ms |
| Cl | X217 | Cl |
| Cl | X217 | $CF_3$ |
| Cl | X218 | Ms |
| Cl | X218 | Cl |
| Cl | X218 | $CF_3$ |
| Cl | X220 | Ms |
| Cl | X220 | Cl |
| Cl | X220 | $CF_3$ |
| Cl | X222 | Ms |
| Cl | X222 | Cl |
| Cl | X222 | $CF_3$ |
| Cl | X226 | Ms |
| Cl | X226 | Cl |
| Cl | X226 | $CF_3$ |
| Cl | X227 | Ms |
| Cl | X227 | Cl |
| Cl | X227 | $CF_3$ |
| Me | X203 | Ms |
| Me | X203 | Cl |
| Me | X203 | $CF_3$ |
| Me | X204 | Ms |
| Me | X204 | Cl |
| Me | X204 | $CF_3$ |
| Me | X206 | Ms |
| Me | X206 | Cl |
| Me | X206 | $CF_3$ |
| Me | X212 | Ms |
| Me | X212 | Cl |
| Me | X212 | $CF_3$ |
| Me | X213 | Ms |
| Me | X213 | Cl |
| Me | X213 | $CF_3$ |
| Me | X214 | Ms |
| Me | X214 | Cl |
| Me | X214 | $CF_3$ |
| Me | X216 | Ms |
| Me | X216 | Cl |
| Me | X216 | $CF_3$ |
| Me | X217 | Ms |
| Me | X217 | Cl |
| Me | X217 | $CF_3$ |
| Me | X218 | Ms |
| Me | X218 | Cl |
| Me | X218 | $CF_3$ |
| Me | X220 | Ms |
| Me | X220 | Cl |
| Me | X220 | $CF_3$ |
| Me | X222 | Ms |
| Me | X222 | Cl |
| Me | X222 | $CF_3$ |

TABLE 4-continued

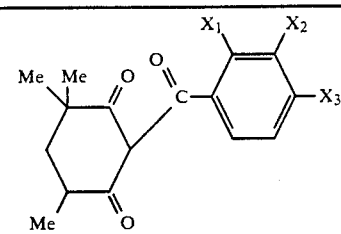

| X₁ | X₂ | X₃ |
|---|---|---|
| Me | X226 | Ms |
| Me | X226 | Cl |
| Me | X226 | CF₃ |
| Me | X227 | Ms |
| Me | X227 | Cl |
| Me | X227 | CF₃ |
| Cl | X211 | Ms |
| Cl | X211 | Cl |
| Cl | X211 | CF₃ |
| Cl | X215 | Ms |
| Cl | X215 | Cl |
| Cl | X215 | CF₃ |
| Cl | X219 | Ms |
| Cl | X219 | Cl |
| Cl | X219 | CF₃ |
| Cl | X221 | Ms |
| Cl | X221 | Cl |
| Cl | X221 | CF₃ |
| Cl | X223 | Ms |
| Cl | X223 | Cl |
| Cl | X223 | CF₃ |
| Cl | X224 | Ms |
| Cl | X224 | Cl |
| Cl | X224 | CF₃ |
| Cl | X225 | Ms |
| Cl | X225 | Cl |
| Cl | X225 | CF₃ |
| Me | X211 | Ms |
| Me | X211 | Cl |
| Me | X211 | CF₃ |
| Me | X215 | Ms |
| Me | X215 | Cl |
| Me | X215 | CF₃ |
| Me | X219 | Ms |
| Me | X219 | Cl |
| Me | X219 | CF₃ |
| Me | X221 | Ms |
| Me | X221 | Cl |
| Me | X221 | CF₃ |
| Me | X223 | Ms |
| Me | X223 | Cl |
| Me | X223 | CF₃ |
| Me | X224 | Ms |
| Me | X224 | Cl |
| Me | X224 | CF₃ |
| Me | X225 | Ms |
| Me | X225 | Cl |
| Me | X225 | CF₃ |
| NO₂ | X201 | Ms |
| NO₂ | X201 | Cl |
| NO₂ | X201 | CF₃ |
| NO₂ | X202 | Ms |
| NO₂ | X202 | Cl |
| NO₂ | X202 | CF₃ |
| NO₂ | X205 | Ms |
| NO₂ | X205 | Cl |
| NO₂ | X205 | CF₃ |
| NO₂ | X207 | Ms |
| NO₂ | X207 | Cl |
| NO₂ | X207 | CF₃ |
| NO₂ | X208 | Ms |
| NO₂ | X208 | Cl |
| NO₂ | X208 | CF₃ |
| NO₂ | X209 | Ms |
| NO₂ | X209 | Cl |
| NO₂ | X209 | CF₃ |
| NO₂ | X210 | Ms |
| NO₂ | X210 | Cl |
| NO₂ | X210 | CF₃ |

TABLE 4-continued

| X₁ | X₂ | X₃ |
|---|---|---|
| Et | X201 | Ms |
| Et | X201 | Cl |
| Et | X201 | CF₃ |
| Et | X202 | Ms |
| Et | X202 | Cl |
| Et | X202 | CF₃ |
| Et | X205 | Ms |
| Et | X205 | Cl |
| Et | X205 | CF₃ |
| Et | X207 | Ms |
| Et | X207 | Cl |
| Et | X207 | CF₃ |
| Et | X208 | Ms |
| Et | X208 | Cl |
| Et | X208 | CF₃ |
| Et | X209 | Ms |
| Et | X209 | Cl |
| Et | X209 | CF₃ |
| Et | X210 | Ms |
| Et | X210 | Cl |
| Et | X210 | CF₃ |
| i-Pr | X201 | Ms |
| i-Pr | X201 | Cl |
| i-Pr | X201 | CF₃ |
| i-Pr | X202 | Ms |
| i-Pr | X202 | Cl |
| i-Pr | X202 | CF₃ |
| i-Pr | X205 | Ms |
| i-Pr | X205 | Cl |
| i-Pr | X205 | CF₃ |
| i-Pr | X207 | Ms |
| i-Pr | X207 | Cl |
| i-Pr | X207 | CF₃ |
| i-Pr | X208 | Ms |
| i-Pr | X208 | Cl |
| i-Pr | X208 | CF₃ |
| i-Pr | X209 | Ms |
| i-Pr | X209 | Cl |
| i-Pr | X209 | CF₃ |
| i-Pr | X210 | Ms |
| i-Pr | X210 | Cl |
| i-Pr | X210 | CF₃ |
| n-Pr | X201 | Ms |
| n-Pr | X201 | Cl |
| n-Pr | X201 | CF₃ |
| n-Pr | X202 | Ms |
| n-Pr | X202 | Cl |
| n-Pr | X202 | CF₃ |
| n-Pr | X205 | Ms |
| n-Pr | X205 | Cl |
| n-Pr | X205 | CF₃ |
| n-Pr | X207 | Ms |
| n-Pr | X207 | Cl |
| n-Pr | X207 | CF₃ |
| n-Pr | X208 | Ms |
| n-Pr | X208 | Cl |
| n-Pr | X208 | CF₃ |
| n-Pr | X209 | Ms |
| n-Pr | X209 | Cl |
| n-Pr | X209 | CF₃ |
| n-Pr | X210 | Ms |
| n-Pr | X210 | Cl |
| n-Pr | X210 | CF₃ |
| CN | X201 | Ms |
| CN | X201 | Cl |
| CN | X201 | CF₃ |
| CN | X202 | Ms |
| CN | X202 | Cl |
| CN | X202 | CF₃ |

TABLE 4-continued

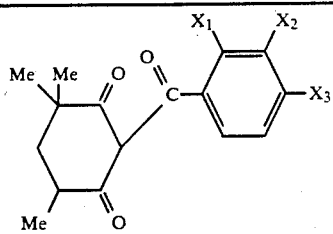

| X₁ | X₂ | X₃ |
|---|---|---|
| CN | X205 | Ms |
| CN | X205 | Cl |
| CN | X205 | CF₃ |
| CN | X207 | Ms |
| CN | X207 | Cl |
| CN | X207 | CF₃ |
| CN | X208 | Ms |
| CN | X208 | Cl |
| CN | X208 | CF₃ |
| CN | X209 | Ms |
| CN | X209 | Cl |
| CN | X209 | CF₃ |
| CN | X210 | Ms |
| CN | X210 | Cl |
| CN | X210 | CF₃ |
| CF₃ | X201 | Ms |
| CF₃ | X201 | Cl |
| CF₃ | X201 | CF₃ |
| CF₃ | X202 | Ms |
| CF₃ | X202 | Cl |
| CF₃ | X202 | CF₃ |
| CF₃ | X205 | Ms |
| CF₃ | X205 | Cl |
| CF₃ | X205 | CF₃ |
| CF₃ | X207 | Ms |
| CF₃ | X207 | Cl |
| CF₃ | X207 | CF₃ |
| CF₃ | X208 | Ms |
| CF₃ | X208 | Cl |
| CF₃ | X208 | CF₃ |
| CF₃ | X209 | Ms |
| CF₃ | X209 | Cl |
| CF₃ | X209 | CF₃ |
| CF₃ | X210 | Ms |
| CF₃ | X210 | Cl |
| CF₃ | X210 | CF₃ |
| F | X201 | Ms |
| F | X201 | Cl |
| F | X201 | CF₃ |
| F | X202 | Ms |
| F | X202 | Cl |
| F | X202 | CF₃ |
| F | X205 | Ms |
| F | X205 | Cl |
| F | X205 | CF₃ |
| F | X207 | Ms |
| F | X207 | Cl |
| F | X207 | CF₃ |
| F | X208 | Ms |
| F | X208 | Cl |
| F | X208 | CF₃ |
| F | X209 | Ms |
| F | X209 | Cl |
| F | X209 | CF₃ |
| F | X210 | Ms |
| F | X210 | Cl |
| F | X210 | CF₃ |
| Br | X201 | Ms |
| Br | X201 | Cl |
| Br | X201 | CF₃ |
| Br | X202 | Ms |
| Br | X202 | Cl |
| Br | X202 | CF₃ |
| Br | X205 | Ms |
| Br | X205 | Cl |
| Br | X205 | CF₃ |
| Br | X207 | Ms |
| Br | X207 | Cl |
| Br | X207 | CF₃ |

TABLE 4-continued

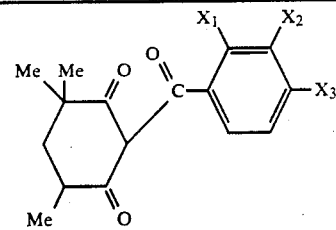

| X₁ | X₂ | X₃ |
|---|---|---|
| Br | X208 | Ms |
| Br | X208 | Cl |
| Br | X208 | CF₃ |
| Br | X209 | Ms |
| Br | X209 | Cl |
| Br | X209 | CF₃ |
| Br | X210 | Ms |
| Br | X210 | Cl |
| Br | X210 | CF₃ |
| I | X201 | Ms |
| I | X201 | Cl |
| I | X201 | CF₃ |
| I | X202 | Ms |
| I | X202 | Cl |
| I | X202 | CF₃ |
| I | X205 | Ms |
| I | X205 | Cl |
| I | X205 | CF₃ |
| I | X207 | Ms |
| I | X207 | Cl |
| I | X207 | CF₃ |
| I | X208 | Ms |
| I | X208 | Cl |
| I | X208 | CF₃ |
| I | X209 | Ms |
| I | X209 | Cl |
| I | X209 | CF₃ |
| I | X210 | Ms |
| I | X210 | Cl |
| I | X210 | CF₃ |
| MeO | X201 | Ms |
| MeO | X201 | Cl |
| MeO | X201 | CF₃ |
| MeO | X202 | Ms |
| MeO | X202 | Cl |
| MeO | X202 | CF₃ |
| MeO | X205 | Ms |
| MeO | X205 | Cl |
| MeO | X205 | CF₃ |
| MeO | X207 | Ms |
| MeO | X207 | Cl |
| MeO | X207 | CF₃ |
| MeO | X208 | Ms |
| MeO | X208 | Cl |
| MeO | X208 | CF₃ |
| MeO | X209 | Ms |
| MeO | X209 | Cl |
| MeO | X209 | CF₃ |
| MeO | X210 | Ms |
| MeO | X210 | Cl |
| MeO | X210 | CF₃ |
| EtO | X201 | Ms |
| EtO | X201 | Cl |
| EtO | X201 | CF₃ |
| EtO | X202 | Ms |
| EtO | X202 | Cl |
| EtO | X202 | CF₃ |
| EtO | X205 | Ms |
| EtO | X205 | Cl |
| EtO | X205 | CF₃ |
| EtO | X207 | Ms |
| EtO | X207 | Cl |
| EtO | X207 | CF₃ |
| EtO | X208 | Ms |
| EtO | X208 | Cl |
| EtO | X208 | CF₃ |
| EtO | X209 | Ms |
| EtO | X209 | Cl |
| EtO | X209 | CF₃ |

TABLE 4-continued

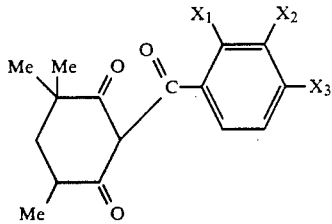

| $X_1$ | $X_2$ | $X_3$ |
|---|---|---|
| EtO | X210 | Ms |
| EtO | X210 | Cl |
| EtO | X210 | $CF_3$ |
| i-PrO | X201 | Ms |
| i-PrO | X201 | Cl |
| i-PrO | X201 | $CF_3$ |
| i-PrO | X202 | Ms |
| i-PrO | X202 | Cl |
| i-PrO | X202 | $CF_3$ |
| i-PrO | X205 | Ms |
| i-PrO | X205 | Cl |
| i-PrO | X205 | $CF_3$ |
| i-PrO | X207 | Ms |
| i-PrO | X207 | Cl |
| i-PrO | X207 | $CF_3$ |
| i-PrO | X208 | Ms |
| i-PrO | X208 | Cl |
| i-PrO | X208 | $CF_3$ |
| i-PrO | X209 | Ms |
| i-PrO | X209 | Cl |
| i-PrO | X209 | $CF_3$ |
| i-PrO | X210 | Ms |
| i-PrO | X210 | Cl |
| i-PrO | X210 | $CF_3$ |
| n-PrO | X201 | Ms |
| n-PrO | X201 | Cl |
| n-PrO | X201 | $CF_3$ |
| n-PrO | X202 | Ms |
| n-PrO | X202 | Cl |
| n-PrO | X202 | $CF_3$ |
| n-PrO | X205 | Ms |
| n-PrO | X205 | Cl |
| n-PrO | X205 | $CF_3$ |
| n-PrO | X207 | Ms |
| n-PrO | X207 | Cl |
| n-PrO | X207 | $CF_3$ |
| n-PrO | X208 | Ms |
| n-PrO | X208 | Cl |
| n-PrO | X208 | $CF_3$ |
| n-PrO | X209 | Ms |
| n-PrO | X209 | Cl |
| n-PrO | X209 | $CF_3$ |
| n-PrO | X210 | Ms |
| n-PrO | X210 | Cl |
| n-PrO | X210 | $CF_3$ |
| $CHF_2$ | X201 | Ms |
| $CHF_2$ | X201 | Cl |
| $CHF_2$ | X201 | $CF_3$ |
| $CHF_2$ | X202 | Ms |
| $CHF_2$ | X202 | Cl |
| $CHF_2$ | X202 | $CF_3$ |
| $CHF_2$ | X205 | Ms |
| $CHF_2$ | X205 | Cl |
| $CHF_2$ | X205 | $CF_3$ |
| $CHF_2$ | X207 | Ms |
| $CHF_2$ | X207 | Cl |
| $CHF_2$ | X207 | $CF_3$ |
| $CHF_2$ | X208 | Ms |
| $CHF_2$ | X208 | Cl |
| $CHF_2$ | X208 | $CF_3$ |
| $CHF_2$ | X209 | Ms |
| $CHF_2$ | X209 | Cl |
| $CHF_2$ | X209 | $CF_3$ |
| $CHF_2$ | X210 | Ms |
| $CHF_2$ | X210 | Cl |
| $CHF_2$ | X210 | $CF_3$ |
| $CH_2CF_3$ | X201 | Ms |
| $CH_2CF_3$ | X201 | Cl |
| $CH_2CF_3$ | X201 | $CF_3$ |

TABLE 4-continued

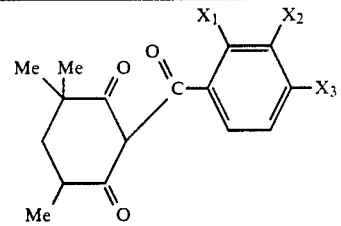

| $X_1$ | $X_2$ | $X_3$ |
|---|---|---|
| $CH_2CF_3$ | X202 | Ms |
| $CH_2CF_3$ | X202 | Cl |
| $CH_2CF_3$ | X202 | $CF_3$ |
| $CH_2CF_3$ | X205 | Ms |
| $CH_2CF_3$ | X205 | Cl |
| $CH_2CF_3$ | X205 | $CF_3$ |
| $CH_2CF_3$ | X207 | Ms |
| $CH_2CF_3$ | X207 | Cl |
| $CH_2CF_3$ | X207 | $CF_3$ |
| $CH_2CF_3$ | X208 | Ms |
| $CH_2CF_3$ | X208 | Cl |
| $CH_2CF_3$ | X208 | $CF_3$ |
| $CH_2CF_3$ | X209 | Ms |
| $CH_2CF_3$ | X209 | Cl |
| $CH_2CF_3$ | X209 | $CF_3$ |
| $CH_2CF_3$ | X210 | Ms |
| $CH_2CF_3$ | X210 | Cl |
| $CH_2CF_3$ | X210 | $CF_3$ |
| X201 | X201 | Ms |
| X201 | X201 | Cl |
| X201 | X201 | $CF_3$ |
| X201 | X202 | Ms |
| X201 | X202 | Cl |
| X201 | X202 | $CF_3$ |
| X201 | X205 | Ms |
| X201 | X205 | Cl |
| X201 | X205 | $CF_3$ |
| X201 | X207 | Ms |
| X201 | X207 | Cl |
| X201 | X207 | $CF_3$ |
| X201 | X208 | Ms |
| X201 | X208 | Cl |
| X201 | X208 | $CF_3$ |
| X201 | X209 | Ms |
| X201 | X209 | Cl |
| X201 | X209 | $CF_3$ |
| X201 | X210 | Ms |
| X201 | X210 | Cl |
| X201 | X210 | $CF_3$ |
| X201 | X203 | Ms |
| X201 | X203 | Cl |
| X201 | X203 | $CF_3$ |
| X201 | X204 | Ms |
| X201 | X204 | Cl |
| X201 | X204 | $CF_3$ |
| X201 | X206 | Ms |
| X201 | X206 | Cl |
| X201 | X206 | $CF_3$ |
| X201 | X212 | Ms |
| X201 | X212 | Cl |
| X201 | X212 | $CF_3$ |
| X201 | X213 | Ms |
| X201 | X213 | Cl |
| X201 | X213 | $CF_3$ |
| X201 | X214 | Ms |
| X201 | X214 | Cl |
| X201 | X214 | $CF_3$ |
| X201 | X216 | Ms |
| X201 | X216 | Cl |
| X201 | X216 | $CF_3$ |
| X201 | X217 | Ms |
| X201 | X217 | Cl |
| X201 | X217 | $CF_3$ |
| X201 | X218 | Ms |
| X201 | X218 | Cl |
| X201 | X218 | $CF_3$ |
| X201 | X220 | Ms |
| X201 | X220 | Cl |
| X201 | X220 | $CF_3$ |

TABLE 4-continued

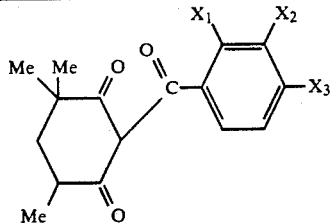

| $X_1$ | $X_2$ | $X_3$ |
|---|---|---|
| X201 | X222 | Ms |
| X201 | X222 | Cl |
| X201 | X222 | CF$_3$ |
| X201 | X226 | Ms |
| X201 | X226 | Cl |
| X201 | X226 | CF$_3$ |
| X201 | X227 | Ms |
| X201 | X227 | Cl |
| X201 | X227 | CF$_3$ |
| X201 | X228 | Ms |
| X201 | X228 | Cl |
| X201 | X228 | CF$_3$ |
| X201 | X229 | Ms |
| X201 | X229 | Cl |
| X201 | X229 | CF$_3$ |
| X201 | X230 | Ms |
| X201 | X230 | Cl |
| X201 | X230 | CF$_3$ |
| X201 | X231 | Ms |
| X201 | X231 | Cl |
| X201 | X231 | CF$_3$ |
| X201 | X232 | Ms |
| X201 | X232 | Cl |
| X201 | X232 | CF$_3$ |
| X201 | X233 | Ms |
| X201 | X233 | Cl |
| X201 | X233 | CF$_3$ |
| X201 | X234 | Ms |
| X201 | X234 | Cl |
| X201 | X234 | CF$_3$ |
| X201 | X235 | Ms |
| X201 | X235 | Cl |
| X201 | X235 | CF$_3$ |
| X202 | X201 | Ms |
| X202 | X201 | Cl |
| X202 | X201 | CF$_3$ |
| X202 | X202 | Ms |
| X202 | X202 | Cl |
| X202 | X202 | CF$_3$ |
| X202 | X205 | Ms |
| X202 | X205 | Cl |
| X202 | X205 | CF$_3$ |
| X202 | X207 | Ms |
| X202 | X207 | Cl |
| X202 | X207 | CF$_3$ |
| X202 | X208 | Ms |
| X202 | X208 | Cl |
| X202 | X208 | CF$_3$ |
| X202 | X209 | Ms |
| X202 | X209 | Cl |
| X202 | X209 | CF$_3$ |
| X202 | X210 | Ms |
| X202 | X210 | Cl |
| X202 | X210 | CF$_3$ |
| X202 | X203 | Ms |
| X202 | X203 | Cl |
| X202 | X203 | CF$_3$ |
| X202 | X204 | Ms |
| X202 | X204 | Cl |
| X202 | X204 | CF$_3$ |
| X202 | X206 | Ms |
| X202 | X206 | Cl |
| X202 | X206 | CF$_3$ |
| X202 | X212 | Ms |
| X202 | X212 | Cl |
| X202 | X212 | CF$_3$ |
| X202 | X213 | Ms |
| X202 | X213 | Cl |
| X202 | X213 | CF$_3$ |

TABLE 4-continued

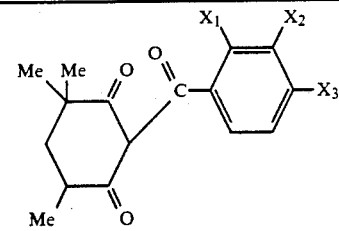

| $X_1$ | $X_2$ | $X_3$ |
|---|---|---|
| X202 | X214 | Ms |
| X202 | X214 | Cl |
| X202 | X214 | CF$_3$ |
| X202 | X216 | Ms |
| X202 | X216 | Cl |
| X202 | X216 | CF$_3$ |
| X202 | X217 | Ms |
| X202 | X217 | Cl |
| X202 | X217 | CF$_3$ |
| X202 | X218 | Ms |
| X202 | X218 | Cl |
| X202 | X218 | CF$_3$ |
| X202 | X220 | Ms |
| X202 | X220 | Cl |
| X202 | X220 | CF$_3$ |
| X202 | X222 | Ms |
| X202 | X222 | Cl |
| X202 | X222 | CF$_3$ |
| X202 | X226 | Ms |
| X202 | X226 | Cl |
| X202 | X226 | CF$_3$ |
| X202 | X227 | Ms |
| X202 | X227 | Cl |
| X202 | X227 | CF$_3$ |
| X202 | X228 | Ms |
| X202 | X228 | Cl |
| X202 | X228 | CF$_3$ |
| X202 | X229 | Ms |
| X202 | X229 | Cl |
| X202 | X229 | CF$_3$ |
| X202 | X230 | Ms |
| X202 | X230 | Cl |
| X202 | X230 | CF$_3$ |
| X202 | X231 | Ms |
| X202 | X231 | Cl |
| X202 | X231 | CF$_3$ |
| X202 | X232 | Ms |
| X202 | X232 | Cl |
| X202 | X232 | CF$_3$ |
| X202 | X233 | Ms |
| X202 | X233 | Cl |
| X202 | X233 | CF$_3$ |
| X202 | X234 | Ms |
| X202 | X234 | Cl |
| X202 | X234 | CF$_3$ |
| X202 | X235 | Ms |
| X202 | X235 | Cl |
| X202 | X235 | CF$_3$ |
| X205 | X201 | Ms |
| X205 | X201 | Cl |
| X205 | X201 | CF$_3$ |
| X205 | X202 | Ms |
| X205 | X202 | Cl |
| X205 | X202 | CF$_3$ |
| X205 | X205 | Ms |
| X205 | X205 | Cl |
| X205 | X205 | CF$_3$ |
| X205 | X207 | Ms |
| X205 | X207 | Cl |
| X205 | X207 | CF$_3$ |
| X205 | X208 | Ms |
| X205 | X208 | Cl |
| X205 | X208 | CF$_3$ |
| X205 | X209 | Ms |
| X205 | X209 | Cl |
| X205 | X209 | CF$_3$ |
| X205 | X210 | Ms |
| X205 | X210 | Cl |
| X205 | X210 | CF$_3$ |

TABLE 4-continued

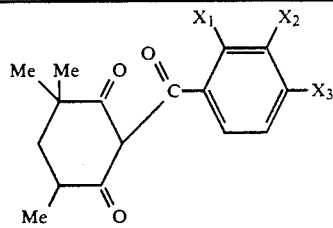

| $X_1$ | $X_2$ | $X_3$ |
|---|---|---|
| X205 | X203 | Ms |
| X205 | X203 | Cl |
| X205 | X203 | $CF_3$ |
| X205 | X204 | Ms |
| X205 | X204 | Cl |
| X205 | X204 | $CF_3$ |
| X205 | X206 | Ms |
| X205 | X206 | Cl |
| X205 | X206 | $CF_3$ |
| X205 | X212 | Ms |
| X205 | X212 | Cl |
| X205 | X212 | $CF_3$ |
| X205 | X213 | Ms |
| X205 | X213 | Cl |
| X205 | X213 | $CF_3$ |
| X205 | X214 | Ms |
| X205 | X214 | Cl |
| X205 | X214 | $CF_3$ |
| X205 | X216 | Ms |
| X205 | X216 | Cl |
| X205 | X216 | $CF_3$ |
| X205 | X217 | Ms |
| X205 | X217 | Cl |
| X205 | X217 | $CF_3$ |
| X205 | X218 | Ms |
| X205 | X218 | Cl |
| X205 | X218 | $CF_3$ |
| X205 | X220 | Ms |
| X205 | X220 | Cl |
| X205 | X220 | $CF_3$ |
| X205 | X222 | Ms |
| X205 | X222 | Cl |
| X205 | X222 | $CF_3$ |
| X205 | X226 | Ms |
| X205 | X226 | Cl |
| X205 | X226 | $CF_3$ |
| X205 | X227 | Ms |
| X205 | X227 | Cl |
| X205 | X227 | $CF_3$ |
| X205 | X228 | Ms |
| X205 | X228 | Cl |
| X205 | X228 | $CF_3$ |
| X205 | X229 | Ms |
| X205 | X229 | Cl |
| X205 | X229 | $CF_3$ |
| X205 | X230 | Ms |
| X205 | X230 | Cl |
| X205 | X230 | $CF_3$ |
| X205 | X231 | Ms |
| X205 | X231 | Cl |
| X205 | X231 | $CF_3$ |
| X205 | X232 | Ms |
| X205 | X232 | Cl |
| X205 | X232 | $CF_3$ |
| X205 | X233 | Ms |
| X205 | X233 | Cl |
| X205 | X233 | $CF_3$ |
| X205 | X234 | Ms |
| X205 | X234 | Cl |
| X205 | X234 | $CF_3$ |
| X207 | X201 | Ms |
| X207 | X201 | Cl |
| X207 | X201 | $CF_3$ |
| X207 | X202 | Ms |
| X207 | X202 | Cl |
| X207 | X202 | $CF_3$ |
| X207 | X205 | Ms |
| X207 | X205 | Cl |
| X207 | X205 | $CF_3$ |

TABLE 4-continued

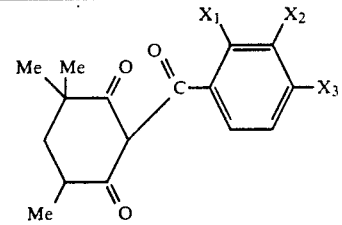

| $X_1$ | $X_2$ | $X_3$ |
|---|---|---|
| X207 | X207 | Ms |
| X207 | X207 | Cl |
| X207 | X207 | $CF_3$ |
| X207 | X208 | Ms |
| X207 | X208 | Cl |
| X207 | X208 | $CF_3$ |
| X207 | X209 | Ms |
| X207 | X209 | Cl |
| X207 | X209 | $CF_3$ |
| X207 | X210 | Ms |
| X207 | X210 | Cl |
| X207 | X210 | $CF_3$ |
| X207 | X203 | Ms |
| X207 | X203 | Cl |
| X207 | X203 | $CF_3$ |
| X207 | X204 | Ms |
| X207 | X204 | Cl |
| X207 | X204 | $CF_3$ |
| X207 | X206 | Ms |
| X207 | X206 | Cl |
| X207 | X206 | $CF_3$ |
| X207 | X212 | Ms |
| X207 | X212 | Cl |
| X207 | X212 | $CF_3$ |
| X207 | X213 | Ms |
| X207 | X213 | Cl |
| X207 | X213 | $CF_3$ |
| X207 | X214 | Ms |
| X207 | X214 | Cl |
| X207 | X214 | $CF_3$ |
| X207 | X216 | Ms |
| X207 | X216 | Cl |
| X207 | X216 | $CF_3$ |
| X207 | X217 | Ms |
| X207 | X217 | Cl |
| X207 | X217 | $CF_3$ |
| X207 | X218 | Ms |
| X207 | X218 | Cl |
| X207 | X218 | $CF_3$ |
| X207 | X220 | Ms |
| X207 | X220 | Cl |
| X207 | X220 | $CF_3$ |
| X207 | X222 | Ms |
| X207 | X222 | Cl |
| X207 | X222 | $CF_3$ |
| X207 | X226 | Ms |
| X207 | X226 | Cl |
| X207 | X226 | $CF_3$ |
| X207 | X227 | Ms |
| X207 | X227 | Cl |
| X207 | X227 | $CF_3$ |
| X208 | X201 | Ms |
| X208 | X201 | Cl |
| X208 | X201 | $CF_3$ |
| X208 | X202 | Ms |
| X208 | X202 | Cl |
| X208 | X202 | $CF_3$ |
| X208 | X205 | Ms |
| X208 | X205 | Cl |
| X208 | X205 | $CF_3$ |
| X208 | X207 | Ms |
| X208 | X207 | Cl |
| X208 | X207 | $CF_3$ |
| X208 | X208 | Ms |
| X208 | X208 | Cl |
| X208 | X208 | $CF_3$ |
| X208 | X209 | Ms |
| X208 | X209 | Cl |
| X208 | X209 | $CF_3$ |

TABLE 4-continued

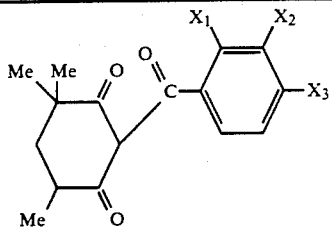

| $X_1$ | $X_2$ | $X_3$ |
|---|---|---|
| X208 | X210 | Ms |
| X208 | X210 | Cl |
| X208 | X210 | $CF_3$ |
| X208 | X203 | Ms |
| X208 | X203 | Cl |
| X208 | X203 | $CF_3$ |
| X208 | X204 | Ms |
| X208 | X204 | Cl |
| X208 | X204 | $CF_3$ |
| X208 | X206 | Ms |
| X208 | X206 | Cl |
| X208 | X206 | $CF_3$ |
| X208 | X212 | Ms |
| X208 | X212 | Cl |
| X208 | X212 | $CF_3$ |
| X208 | X213 | Ms |
| X208 | X213 | Cl |
| X208 | X213 | $CF_3$ |
| X208 | X214 | Ms |
| X208 | X214 | Cl |
| X208 | X214 | $CF_3$ |
| X208 | X216 | Ms |
| X208 | X216 | Cl |
| X208 | X216 | $CF_3$ |
| X208 | X217 | Ms |
| X208 | X217 | Cl |
| X208 | X217 | $CF_3$ |
| X208 | X218 | Ms |
| X208 | X218 | Cl |
| X208 | X218 | $CF_3$ |
| X208 | X220 | Ms |
| X208 | X220 | Cl |
| X208 | X220 | $CF_3$ |
| X208 | X222 | Ms |
| X208 | X222 | Cl |
| X208 | X222 | $CF_3$ |
| X208 | X226 | Ms |
| X208 | X226 | Cl |
| X208 | X226 | $CF_3$ |
| X208 | X227 | Ms |
| X208 | X227 | Cl |
| X208 | X227 | $CF_3$ |
| X209 | X201 | Ms |
| X209 | X201 | Cl |
| X209 | X201 | $CF_3$ |
| X209 | X202 | Ms |
| X209 | X202 | Cl |
| X209 | X202 | $CF_3$ |
| X209 | X205 | Ms |
| X209 | X205 | Cl |
| X209 | X205 | $CF_3$ |
| X209 | X207 | Ms |
| X209 | X207 | Cl |
| X209 | X207 | $CF_3$ |
| X209 | X208 | Ms |
| X209 | X208 | Cl |
| X209 | X208 | $CF_3$ |
| X209 | X209 | Ms |
| X209 | X209 | Cl |
| X209 | X209 | $CF_3$ |
| X209 | X210 | Ms |
| X209 | X210 | Cl |
| X209 | X210 | $CF_3$ |
| X209 | X203 | Ms |
| X209 | X203 | Cl |
| X209 | X203 | $CF_3$ |
| X209 | X204 | Ms |
| X209 | X204 | Cl |
| X209 | X204 | $CF_3$ |

TABLE 4-continued

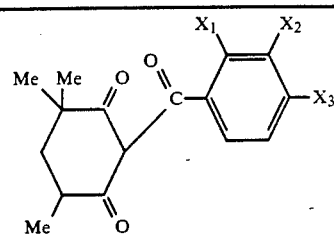

| $X_1$ | $X_2$ | $X_3$ |
|---|---|---|
| X209 | X206 | Ms |
| X209 | X206 | Cl |
| X209 | X206 | $CF_3$ |
| X209 | X212 | Ms |
| X209 | X212 | Cl |
| X209 | X212 | $CF_3$ |
| X209 | X213 | Ms |
| X209 | X213 | Cl |
| X209 | X213 | $CF_3$ |
| X209 | X214 | Ms |
| X209 | X214 | Cl |
| X209 | X214 | $CF_3$ |
| X209 | X216 | Ms |
| X209 | X216 | Cl |
| X209 | X216 | $CF_3$ |
| X209 | X217 | Ms |
| X209 | X217 | Cl |
| X209 | X217 | $CF_3$ |
| X209 | X218 | Ms |
| X209 | X218 | Cl |
| X209 | X218 | $CF_3$ |
| X209 | X220 | Ms |
| X209 | X220 | Cl |
| X209 | X220 | $CF_3$ |
| X209 | X222 | Ms |
| X209 | X222 | Cl |
| X209 | X222 | $CF_3$ |
| X209 | X226 | Ms |
| X209 | X226 | Cl |
| X209 | X226 | $CF_3$ |
| X209 | X227 | Ms |
| X209 | X227 | Cl |
| X209 | X227 | $CF_3$ |
| X210 | X201 | Ms |
| X210 | X201 | Cl |
| X210 | X201 | $CF_3$ |
| X210 | X202 | Ms |
| X210 | X202 | Cl |
| X210 | X202 | $CF_3$ |
| X210 | X205 | Ms |
| X210 | X205 | Cl |
| X210 | X205 | $CF_3$ |
| X210 | X207 | Ms |
| X210 | X207 | Cl |
| X210 | X207 | $CF_3$ |
| X210 | X208 | Ms |
| X210 | X208 | Cl |
| X210 | X208 | $CF_3$ |
| X210 | X209 | Ms |
| X210 | X209 | Cl |
| X210 | X209 | $CF_3$ |
| X210 | X210 | Ms |
| X210 | X210 | Cl |
| X210 | X210 | $CF_3$ |
| X210 | X203 | Ms |
| X210 | X203 | Cl |
| X210 | X203 | $CF_3$ |
| X210 | X204 | Ms |
| X210 | X204 | Cl |
| X210 | X204 | $CF_3$ |
| X210 | X206 | Ms |
| X210 | X206 | Cl |
| X210 | X206 | $CF_3$ |
| X210 | X212 | Ms |
| X210 | X212 | Cl |
| X210 | X212 | $CF_3$ |
| X210 | X213 | Ms |
| X210 | X213 | Cl |
| X210 | X213 | $CF_3$ |

TABLE 4-continued

[Structure: 4,4,6-trimethyl-cyclohexane-1,3-dione substituted at 2-position with C(=O)-phenyl bearing X₁ (ortho), X₂ (meta), X₃ (para)]

| X₁ | X₂ | X₃ |
|---|---|---|
| X210 | X214 | Ms |
| X210 | X214 | Cl |
| X210 | X214 | CF₃ |
| X210 | X216 | Ms |
| X210 | X216 | Cl |
| X210 | X216 | CF₃ |
| X210 | X217 | Ms |
| X210 | X217 | Cl |
| X210 | X217 | CF₃ |
| X210 | X218 | Ms |
| X210 | X218 | Cl |
| X210 | X218 | CF₃ |
| X210 | X220 | Ms |
| X210 | X220 | Cl |
| X210 | X220 | CF₃ |
| X210 | X222 | Ms |
| X210 | X222 | Cl |
| X210 | X222 | CF₃ |
| X210 | X226 | Ms |
| X210 | X226 | Cl |
| X210 | X226 | CF₃ |
| X210 | X227 | Ms |
| X210 | X227 | Cl |
| X210 | X227 | CF₃ |
| Cl | X201 | NO₂ |
| Cl | X201 | MeO |
| Cl | X201 | CN |
| Cl | X201 | SMe |
| Cl | X201 | SOMe |
| Cl | X201 | SO₂CF₃ |
| Cl | X201 | Br |
| Cl | X201 | I |
| Cl | X201 | EtO |
| Cl | X202 | NO₂ |
| Cl | X202 | MeO |
| Cl | X202 | CN |
| Cl | X202 | SMe |
| Cl | X202 | SOMe |
| Cl | X202 | SO₂CF₃ |
| Cl | X202 | Br |
| Cl | X202 | I |
| Cl | X202 | EtO |
| Cl | X205 | NO₂ |
| Cl | X205 | MeO |
| Cl | X205 | CN |
| Cl | X205 | SMe |
| Cl | X205 | SOMe |
| Cl | X205 | SO₂CF₃ |
| Cl | X205 | Br |
| Cl | X205 | I |
| Cl | X205 | EtO |
| Cl | X207 | NO₂ |
| Cl | X207 | MeO |
| Cl | X207 | CN |
| Cl | X207 | SMe |
| Cl | X207 | SOMe |
| Cl | X207 | SO₂CF₃ |
| Cl | X207 | Br |
| Cl | X207 | I |
| Cl | X207 | EtO |
| Cl | X208 | NO₂ |
| Cl | X208 | MeO |
| Cl | X208 | CN |
| Cl | X208 | SMe |
| Cl | X208 | SOMe |
| Cl | X208 | SO₂CF₃ |
| Cl | X208 | Br |
| Cl | X208 | I |
| Cl | X208 | EtO |

TABLE 4-continued

[Structure: 4,4,6-trimethyl-cyclohexane-1,3-dione substituted at 2-position with C(=O)-phenyl bearing X₁ (ortho), X₂ (meta), X₃ (para)]

| X₁ | X₂ | X₃ |
|---|---|---|
| Cl | X209 | NO₂ |
| Cl | X209 | MeO |
| Cl | X209 | CN |
| Cl | X209 | SMe |
| Cl | X209 | SOMe |
| Cl | X209 | SO₂CF₃ |
| Cl | X209 | Br |
| Cl | X209 | I |
| Cl | X209 | EtO |
| Cl | X210 | NO₂ |
| Cl | X210 | MeO |
| Cl | X210 | CN |
| Cl | X210 | SMe |
| Cl | X210 | SOMe |
| Cl | X210 | SO₂CF₃ |
| Cl | X210 | Br |
| Cl | X210 | I |
| Cl | X210 | EtO |
| Me | X201 | NO₂ |
| Me | X201 | MeO |
| Me | X201 | CN |
| Me | X201 | SMe |
| Me | X201 | SOMe |
| Me | X201 | SO₂CF₃ |
| Me | X201 | Br |
| Me | X201 | I |
| Me | X201 | EtO |
| Me | X202 | NO₂ |
| Me | X202 | MeO |
| Me | X202 | CN |
| Me | X202 | SMe |
| Me | X202 | SOMe |
| Me | X202 | SO₂CF₃ |
| Me | X202 | Br |
| Me | X202 | I |
| Me | X202 | EtO |
| Me | X205 | NO₂ |
| Me | X205 | MeO |
| Me | X205 | CN |
| Me | X205 | SMe |
| Me | X205 | SOMe |
| Me | X205 | SO₂CF₃ |
| Me | X205 | Br |
| Me | X205 | I |
| Me | X205 | EtO |
| Me | X207 | NO₂ |
| Me | X207 | MeO |
| Me | X207 | CN |
| Me | X207 | SMe |
| Me | X207 | SOMe |
| Me | X207 | SO₂CF₃ |
| Me | X207 | Br |
| Me | X207 | I |
| Me | X207 | EtO |
| Me | X208 | NO₂ |
| Me | X208 | MeO |
| Me | X208 | CN |
| Me | X208 | SMe |
| Me | X208 | SOMe |
| Me | X208 | SO₂CF₃ |
| Me | X208 | Br |
| Me | X208 | I |
| Me | X208 | EtO |
| Me | X209 | NO₂ |
| Me | X209 | MeO |
| Me | X209 | CN |
| Me | X209 | SMe |
| Me | X209 | SOMe |
| Me | X209 | SO₂CF₃ |

TABLE 4-continued

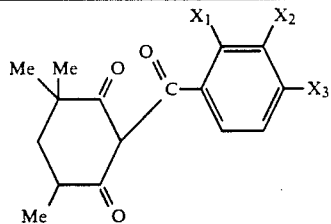

| X₁ | X₂ | X₃ |
|---|---|---|
| Me | X209 | Br |
| Me | X209 | I |
| Me | X209 | EtO |
| Me | X210 | $NO_2$ |
| Me | X210 | MeO |
| Me | X210 | CN |
| Me | X210 | SMe |
| Me | X210 | SOMe |
| Me | X210 | $SO_2CF_3$ |
| Me | X210 | Br |
| Me | X210 | I |
| Me | X210 | EtO |

TABLE 5

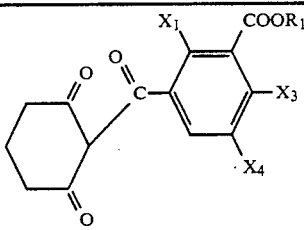

| X₁ | X₃ | X₄ | R₁ |
|---|---|---|---|
| Cl | $SO_2Me$ | H | H |
| Cl | $SO_2Me$ | H | Me |
| Cl | $SO_2Me$ | H | Et |
| Cl | $SO_2Me$ | H | Pr-i |
| Cl | $SO_2Me$ | H | Pr-n |
| Cl | $SO_2Me$ | H | Bu-t |
| Cl | $SO_2Me$ | H | $CH_2C{\equiv}CH$ |
| Cl | $SO_2Me$ | H | $CH_2C{=}CH_2$ |
| Cl | $SO_2Me$ | H | $CH_2CH_2OMe$ |
| Cl | $SO_2Me$ | H | $CH_2CH_2Cl$ |
| Cl | $SO_2Me$ | H | $CH_2CF_3$ |
| Cl | $SO_2Me$ | H | $CH_2CH_2CN$ |
| Cl | $SO_2Me$ | F | Me |
| Cl | $SO_2Me$ | F | Et |
| Cl | $SO_2Me$ | F | Pr-i |
| Cl | $SO_2Me$ | Cl | Me |
| Cl | $SO_2Me$ | Cl | Et |
| Cl | $SO_2Me$ | Cl | Pr-i |
| Cl | $SO_2Me$ | Me | Me |
| Cl | $SO_2Me$ | Me | Et |
| Cl | $SO_2Me$ | OMe | Me |
| Cl | $SO_2Me$ | OMe | Et |
| Cl | $SO_2Me$ | OMe | Pr-i |
| Cl | SOMe | H | Me |
| Cl | SOMe | H | Et |
| Cl | SOMe | H | Pr-i |
| Cl | SMe | H | Me |
| Cl | SMe | H | Et |
| Cl | SMe | H | Pr-i |
| Cl | $SO_2CF_3$ | H | Me |
| Cl | $SO_2CF_3$ | H | Et |
| Cl | $SO_2CF_3$ | H | Pr-i |
| Cl | $SO_2CF_3$ | H | Pr-n |
| Cl | $SOCF_3$ | H | Me |
| Cl | $SOCF_3$ | H | Et |
| Cl | $SOCF_3$ | H | Pr-i |
| Cl | $SCF_3$ | H | Me |
| Cl | $SCF_3$ | H | Et |
| Cl | $SCF_3$ | H | Pr-i |
| Cl | Cl | H | Me |

TABLE 5-continued

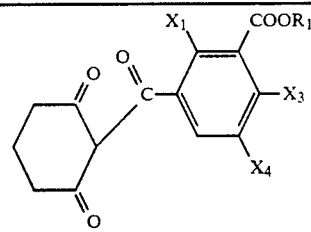

| X₁ | X₃ | X₄ | R₁ |
|---|---|---|---|
| Cl | Cl | H | Et |
| Cl | Cl | H | Pr-i |
| Cl | Cl | H | Pr-n |
| Cl | Br | H | Me |
| Cl | Br | H | Et |
| Cl | Br | H | Pr-i |
| Cl | $NO_2$ | H | Me |
| Cl | $NO_2$ | H | Et |
| Cl | $NO_2$ | H | Pr-i |
| Cl | $CF_3$ | H | Me |
| Cl | $CF_3$ | H | Et |
| Cl | $CF_3$ | H | Pr-i |
| Cl | CN | H | Me |
| Cl | CN | H | Et |
| Cl | OMe | H | Me |
| Cl | OMe | H | Et |
| OMe | $SO_2Me$ | H | H |
| OMe | $SO_2Me$ | H | Me |
| OMe | $SO_2Me$ | H | Et |
| OMe | $SO_2Me$ | H | Pr-i |
| OMe | $SO_2Me$ | H | Pr-n |
| OMe | $SO_2Me$ | H | Bu-t |
| OMe | $SO_2Me$ | H | $CH_2C{\equiv}CH$ |
| OMe | $SO_2Me$ | H | $CH_2C{=}CH_2$ |
| OMe | $SO_2Me$ | H | $CH_2CH_2OMe$ |
| OMe | $SO_2Me$ | H | $CH_2CH_2Cl$ |
| OMe | $SO_2Me$ | H | $CH_2CF_3$ |
| OMe | $SO_2Me$ | H | $CH_2CH_2CN$ |
| OMe | $SO_2Me$ | F | Me |
| OMe | $SO_2Me$ | F | Et |
| OMe | $SO_2Me$ | F | Pr-i |
| OMe | $SO_2Me$ | F | Pr-n |
| OMe | $SO_2Me$ | Cl | Me |
| OMe | $SO_2Me$ | Cl | Et |
| OMe | $SO_2Me$ | Cl | Pr-i |
| OMe | $SO_2Me$ | Cl | Pr-n |
| OMe | $SO_2Me$ | Me | Me |
| OMe | $SO_2Me$ | Me | Et |
| OMe | $SO_2Me$ | Me | Pr-i |
| OMe | $SO_2Me$ | Me | Pr-n |
| OMe | $SO_2Me$ | OMe | Me |
| OMe | $SO_2Me$ | OMe | Et |
| OMe | $SO_2Me$ | OMe | Pr-i |
| OMe | $SO_2Me$ | OMe | Pr-n |
| OMe | SOMe | H | Me |
| OMe | SOMe | H | Et |
| OMe | SOMe | H | Pr-i |
| OMe | SMe | H | Me |
| OMe | SMe | H | Et |
| OMe | SMe | H | Pr-i |
| OMe | $SO_2CF_3$ | H | Me |
| OMe | $SO_2CF_3$ | H | Et |
| OMe | $SO_2CF_3$ | H | Pr-i |
| OMe | $SO_2CF_3$ | H | Pr-n |
| OMe | $SOCF_3$ | H | Me |
| OMe | $SOCF_3$ | H | Et |
| OMe | $SOCF_3$ | H | Pr-i |
| OMe | $SCF_3$ | H | Me |
| OMe | $SCF_3$ | H | Et |
| OMe | $SCF_3$ | H | Pr-i |
| OMe | Cl | H | Me |
| OMe | Cl | H | Et |
| OMe | Cl | H | Pr-i |
| OMe | Cl | H | Pr-n |
| OMe | Br | H | Me |
| OMe | Br | H | Et |
| OMe | Br | H | Pr-i |
| OMe | $NO_2$ | H | Me |
| OMe | $NO_2$ | H | Et |

TABLE 5-continued

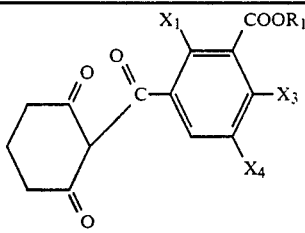

| $X_1$ | $X_3$ | $X_4$ | $R_1$ |
|---|---|---|---|
| OMe | NO$_2$ | H | Pr-i |
| OMe | CF$_3$ | H | Me |
| OMe | CF$_3$ | H | Et |
| OMe | CF$_3$ | H | Pr-i |
| OMe | CN | H | Me |
| OMe | CN | H | Et |
| OMe | OMe | H | Me |
| OMe | OMe | H | Et |
| Br | SO$_2$Me | H | Me |
| Br | SO$_2$Me | H | Et |
| Br | SO$_2$Me | H | Pr-i |
| Br | SO$_2$Me | H | Pr-n |
| Br | SOMe | H | Me |
| Br | SOMe | H | Et |
| Br | SMe | H | Me |
| Br | SMe | H | Et |
| Br | SO$_2$CF$_3$ | H | Me |
| Br | SO$_2$CF$_3$ | H | Et |
| Br | SOCF$_3$ | H | Me |
| Br | SOCF$_3$ | H | Et |
| Br | SCF$_3$ | H | Me |
| Br | SCF$_3$ | H | Et |
| Br | Cl | H | Me |
| Br | Cl | H | Et |
| Br | Cl | H | Pr-i |
| Br | Cl | H | Pr-n |
| Br | Br | H | Me |
| Br | Br | H | Et |
| Br | NO$_2$ | H | Me |
| Br | NO$_2$ | H | Et |
| Br | CF$_3$ | H | Me |
| Br | CF$_3$ | H | Et |
| I | SO$_2$Me | H | Me |
| I | SO$_2$Me | H | Et |
| I | SO$_2$Me | H | Pr-i |
| I | SO$_2$Me | H | Pr-n |
| I | SO$_2$Me | H | Bu-t |
| I | SOMe | H | Me |
| I | SOMe | H | Et |
| I | SMe | H | Me |
| I | SMe | H | Et |
| I | SO$_2$CF$_3$ | H | Me |
| I | SO$_2$CF$_3$ | H | Et |
| I | SOCF$_3$ | H | Me |
| I | SOCF$_3$ | H | Et |
| I | SCF$_3$ | H | Me |
| I | SCF$_3$ | H | Et |
| I | Cl | H | Me |
| I | Cl | H | Et |
| I | Cl | H | Pr-i |
| I | Cl | H | Pr-n |
| I | Br | H | Me |
| I | Br | H | Et |
| I | NO$_2$ | H | Me |
| I | NO$_2$ | H | Et |
| I | CF$_3$ | H | Me |
| I | CF$_3$ | H | Et |
| CH$_2$OMe | SO$_2$Me | H | Me |
| CH$_2$OMe | SO$_2$Me | H | Et |
| CH$_2$OMe | SO$_2$Me | H | Pr-i |
| CH$_2$OMe | SO$_2$Me | H | Pr-n |
| CH$_2$OMe | SO$_2$Me | H | Bu-t |
| CH$_2$OMe | SOMe | H | Me |
| CH$_2$OMe | SOMe | H | Et |
| CH$_2$OMe | SMe | H | Me |
| CH$_2$OMe | SMe | H | Et |
| CH$_2$OMe | SO$_2$CF$_3$ | H | Me |
| CH$_2$OMe | SO$_2$CF$_3$ | H | Et |
| CH$_2$OMe | SOCF$_3$ | H | Me |

TABLE 5-continued

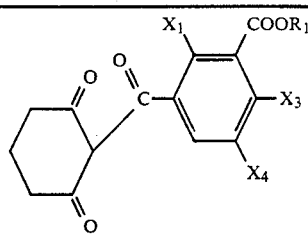

| $X_1$ | $X_3$ | $X_4$ | $R_1$ |
|---|---|---|---|
| CH$_2$OMe | SOCF$_3$ | H | Et |
| CH$_2$OMe | SCF$_3$ | H | Me |
| CH$_2$OMe | SCF$_3$ | H | Et |
| CH$_2$OMe | Cl | H | Me |
| CH$_2$OMe | Cl | H | Et |
| CH$_2$OMe | Cl | H | Pr-i |
| CH$_2$OMe | Cl | H | Pr-n |
| CH$_2$OMe | Br | H | Me |
| CH$_2$OMe | Br | H | Et |
| CH$_2$OMe | NO$_2$ | H | Me |
| CH$_2$OMe | NO$_2$ | H | Et |
| CH$_2$OMe | CF$_3$ | H | Me |
| CH$_2$OMe | CF$_3$ | H | Et |
| F | SO$_2$Me | H | Me |
| F | SO$_2$Me | H | Et |
| F | SO$_2$CF$_3$ | H | Me |
| F | SO$_2$CF$_3$ | H | Et |
| F | Cl | H | Me |
| F | Cl | H | Et |
| OEt | SO$_2$Me | H | Me |
| OEt | SO$_2$Me | H | Et |
| OEt | SO$_2$CF$_3$ | H | Me |
| OEt | SO$_2$CF$_3$ | H | Et |
| OEt | Cl | H | Me |
| OEt | Cl | H | Et |
| OPr-i | SO$_2$Me | H | Me |
| OPr-i | SO$_2$Me | H | Et |
| OPr-i | SO$_2$CF$_3$ | H | Me |
| OPr-i | SO$_2$CF$_3$ | H | Et |
| OPr-i | Cl | H | Me |
| OPr-i | Cl | H | Et |
| OCHF$_2$ | SO$_2$Me | H | Me |
| OCHF$_2$ | SO$_2$Me | H | Et |
| OCHF$_2$ | SO$_2$CF$_3$ | H | Me |
| OCHF$_2$ | SO$_2$CF$_3$ | H | Et |
| OCHF$_2$ | Cl | H | Me |
| OCHF$_2$ | Cl | H | Et |
| OCF$_3$ | SO$_2$Me | H | Me |
| OCF$_3$ | SO$_2$Me | H | Et |
| OCF$_3$ | SO$_2$CF$_3$ | H | Me |
| OCF$_3$ | SO$_2$CF$_3$ | H | Et |
| OCF$_3$ | Cl | H | Me |
| OCF$_3$ | Cl | H | Et |
| OCH$_2$CF$_3$ | SO$_2$Me | H | Me |
| OCH$_2$CF$_3$ | SO$_2$Me | H | Et |
| OCH$_2$CF$_3$ | SO$_2$CF$_3$ | H | Me |
| OCH$_2$CF$_3$ | SO$_2$CF$_3$ | H | Et |
| OCH$_2$CF$_3$ | Cl | H | Me |
| OCH$_2$CF$_3$ | Cl | H | Et |
| CH$_2$OEt | SO$_2$Me | H | Me |
| CH$_2$OEt | SO$_2$Me | H | Et |
| CH$_2$OEt | SO$_2$CF$_3$ | H | Me |
| CH$_2$OEt | SO$_2$CF$_3$ | H | Et |
| CH$_2$OEt | Cl | H | Me |
| CH$_2$OEt | Cl | H | Et |
| CH$_2$SMe | SO$_2$Me | H | Me |
| CH$_2$SMe | SO$_2$Me | H | Et |
| CH$_2$SMe | SO$_2$CF$_3$ | H | Me |
| CH$_2$SMe | SO$_2$CF$_3$ | H | Et |
| CH$_2$SMe | Cl | H | Me |
| CH$_2$SMe | Cl | H | Et |

TABLE 6

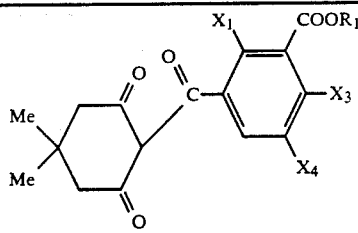

| $X_1$ | $X_3$ | $X_4$ | $R_1$ |
|---|---|---|---|
| Cl | SO$_2$Me | H | H |
| Cl | SO$_2$Me | H | Me |
| Cl | SO$_2$Me | H | Et |
| Cl | SO$_2$Me | H | Pr-i |
| Cl | SO$_2$Me | H | Pr-n |
| Cl | SO$_2$Me | H | Bu-t |
| Cl | SO$_2$Me | H | CH$_2$C≡CH |
| Cl | SO$_2$Me | H | CH$_2$C=CH$_2$ |
| Cl | SO$_2$Me | H | CH$_2$CH$_2$OMe |
| Cl | SO$_2$Me | H | CH$_2$CH$_2$Cl |
| Cl | SO$_2$Me | H | CH$_2$CF$_3$ |
| Cl | SO$_2$Me | H | CH$_2$CH$_2$CN |
| Cl | SO$_2$Me | F | Me |
| Cl | SO$_2$Me | F | Et |
| Cl | SO$_2$Me | F | Pr-i |
| Cl | SO$_2$Me | Cl | Me |
| Cl | SO$_2$Me | Cl | Et |
| Cl | SO$_2$Me | Cl | Pr-i |
| Cl | SO$_2$Me | Me | Me |
| Cl | SO$_2$Me | Me | Et |
| Cl | SO$_2$Me | OMe | Me |
| Cl | SO$_2$Me | OMe | Et |
| Cl | SO$_2$Me | OMe | Pr-i |
| Cl | SOMe | H | Me |
| Cl | SOMe | H | Et |
| Cl | SOMe | H | Pr-i |
| Cl | SMe | H | Me |
| Cl | SMe | H | Et |
| Cl | SMe | H | Pr-i |
| Cl | SO$_2$CF$_3$ | H | Me |
| Cl | SO$_2$CF$_3$ | H | Et |
| Cl | SO$_2$CF$_3$ | H | Pr-i |
| Cl | SO$_2$CF$_3$ | H | Pr-n |
| Cl | SOCF$_3$ | H | Me |
| Cl | SOCF$_3$ | H | Et |
| Cl | SOCF$_3$ | H | Pr-i |
| Cl | SCF$_3$ | H | Me |
| Cl | SCF$_3$ | H | Et |
| Cl | SCF$_3$ | H | Pr-i |
| Cl | Cl | H | Me |
| Cl | Cl | H | Et |
| Cl | Cl | H | Pr-i |
| Cl | Cl | H | Pr-n |
| Cl | Br | H | Me |
| Cl | Br | H | Et |
| Cl | Br | H | Pr-i |
| Cl | NO$_2$ | H | Me |
| Cl | NO$_2$ | H | Et |
| Cl | NO$_2$ | H | Pr-i |
| Cl | CF$_3$ | H | Me |
| Cl | CF$_3$ | H | Et |
| Cl | CF$_3$ | H | Pr-i |
| Cl | CN | H | Me |
| Cl | CN | H | Et |
| Cl | OMe | H | Me |
| Cl | OMe | H | Et |
| OMe | SO$_2$Me | H | H |
| OMe | SO$_2$Me | H | Me |
| OMe | SO$_2$Me | H | Et |
| OMe | SO$_2$Me | H | Pr-i |
| OMe | SO$_2$Me | H | Pr-n |
| OMe | SO$_2$Me | H | Bu-t |
| OMe | SO$_2$Me | H | CH$_2$C≡CH |
| OMe | SO$_2$Me | H | CH$_2$C=CH$_2$ |
| OMe | SO$_2$Me | H | CH$_2$CH$_2$OMe |
| OMe | SO$_2$Me | H | CH$_2$CH$_2$Cl |
| OMe | SO$_2$Me | H | CH$_2$CF$_3$ |
| OMe | SO$_2$Me | H | CH$_2$CH$_2$CN |
| OMe | SO$_2$Me | F | Me |

TABLE 6-continued

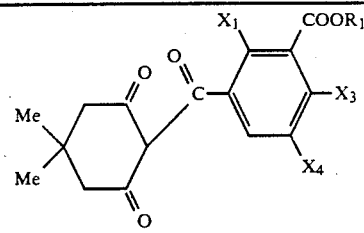

| $X_1$ | $X_3$ | $X_4$ | $R_1$ |
|---|---|---|---|
| OMe | SO$_2$Me | F | Et |
| OMe | SO$_2$Me | F | Pr-i |
| OMe | SO$_2$Me | F | Pr-n |
| OMe | SO$_2$Me | Cl | Me |
| OMe | SO$_2$Me | Cl | Et |
| OMe | SO$_2$Me | Cl | Pr-i |
| OMe | SO$_2$Me | Cl | Pr-n |
| OMe | SO$_2$Me | Me | Me |
| OMe | SO$_2$Me | Me | Et |
| OMe | SO$_2$Me | Me | Pr-i |
| OMe | SO$_2$Me | Me | Pr-n |
| OMe | SO$_2$Me | OMe | Me |
| OMe | SO$_2$Me | OMe | Et |
| OMe | SO$_2$Me | OMe | Pr-i |
| OMe | SO$_2$Me | OMe | Pr-n |
| OMe | SOMe | H | Me |
| OMe | SOMe | H | Et |
| OMe | SOMe | H | Pr-i |
| OMe | SMe | H | Me |
| OMe | SMe | H | Et |
| OMe | SMe | H | Pr-i |
| OMe | SO$_2$CF$_3$ | H | Me |
| OMe | SO$_2$CF$_3$ | H | Et |
| OMe | SO$_2$CF$_3$ | H | Pr-i |
| OMe | SO$_2$CF$_3$ | H | Pr-n |
| OMe | SOCF$_3$ | H | Me |
| OMe | SOCF$_3$ | H | Et |
| OMe | SOCF$_3$ | H | Pr-i |
| OMe | SCF$_3$ | H | Me |
| OMe | SCF$_3$ | H | Et |
| OMe | SCF$_3$ | H | Pr-i |
| OMe | Cl | H | Me |
| OMe | Cl | H | Et |
| OMe | Cl | H | Pr-i |
| OMe | Cl | H | Pr-n |
| OMe | Br | H | Me |
| OMe | Br | H | Et |
| OMe | Br | H | Pr-i |
| OMe | NO$_2$ | H | Me |
| OMe | NO$_2$ | H | Et |
| OMe | NO$_2$ | H | Pr-i |
| OMe | CF$_3$ | H | Me |
| OMe | CF$_3$ | H | Et |
| OMe | CF$_3$ | H | Pr-i |
| OMe | CN | H | Me |
| OMe | CN | H | Et |
| OMe | OMe | H | Me |
| OMe | OMe | H | Et |
| Br | SO$_2$Me | H | Me |
| Br | SO$_2$Me | H | Et |
| Br | SO$_2$Me | H | Pr-i |
| Br | SO$_2$Me | H | Pr-n |
| Br | SOMe | H | Me |
| Br | SOMe | H | Et |
| Br | SMe | H | Me |
| Br | SMe | H | Et |
| Br | SO$_2$CF$_3$ | H | Me |
| Br | SO$_2$CF$_3$ | H | Et |
| Br | SOCF$_3$ | H | Me |
| Br | SOCF$_3$ | H | Et |
| Br | SCF$_3$ | H | Me |
| Br | SCF$_3$ | H | Et |
| Br | Cl | H | Me |
| Br | Cl | H | Et |
| Br | Cl | H | Pr-i |
| Br | Cl | H | Pr-n |
| Br | Br | H | Me |
| Br | Br | H | Et |
| Br | NO$_2$ | H | Me |

TABLE 6-continued

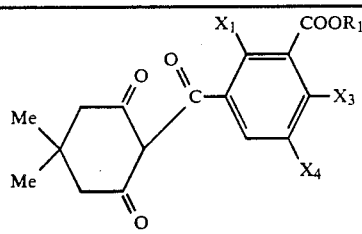

| X₁ | X₃ | X₄ | R₁ |
|---|---|---|---|
| Br | NO₂ | H | Et |
| Br | CF₃ | H | Me |
| Br | CF₃ | H | Et |
| I | SO₂Me | H | Me |
| I | SO₂Me | H | Et |
| I | SO₂Me | H | Pr-i |
| I | SO₂Me | H | Pr-n |
| I | SO₂Me | H | Bu-t |
| I | SOMe | H | Me |
| I | SOMe | H | Et |
| I | SMe | H | Me |
| I | SMe | H | Et |
| I | SO₂CF₃ | H | Me |
| I | SO₂CF₃ | H | Et |
| I | SOCF₃ | H | Me |
| I | SOCF₃ | H | Et |
| I | SCF₃ | H | Me |
| I | SCF₃ | H | Et |
| I | Cl | H | Me |
| I | Cl | H | Et |
| I | Cl | H | Pr-i |
| I | Cl | H | Pr-n |
| I | Br | H | Me |
| I | Br | H | Et |
| I | NO₂ | H | Me |
| I | NO₂ | H | Et |
| I | CF₃ | H | Me |
| I | CF₃ | H | Et |
| CH₂OMe | SO₂Me | H | Me |
| CH₂OMe | SO₂Me | H | Et |
| CH₂OMe | SO₂Me | H | Pr-i |
| CH₂OMe | SO₂Me | H | Pr-n |
| CH₂OMe | SO₂Me | H | Bu-t |
| CH₂OMe | SOMe | H | Me |
| CH₂OMe | SOMe | H | Et |
| CH₂OMe | SMe | H | Me |
| CH₂OMe | SMe | H | Et |
| CH₂OMe | SO₂CF₃ | H | Me |
| CH₂OMe | SO₂CF₃ | H | Et |
| CH₂OMe | SOCF₃ | H | Me |
| CH₂OMe | SOCF₃ | H | Et |
| CH₂OMe | SCF₃ | H | Me |
| CH₂OMe | SCF₃ | H | Et |
| CH₂OMe | Cl | H | Me |
| CH₂OMe | Cl | H | Et |
| CH₂OMe | Cl | H | Pr-i |
| CH₂OMe | Cl | H | Pr-n |
| CH₂OMe | Br | H | Me |
| CH₂OMe | Br | H | Et |
| CH₂OMe | NO₂ | H | Me |
| CH₂OMe | NO₂ | H | Et |
| CH₂OMe | CF₃ | H | Me |
| CH₂OMe | CF₃ | H | Et |
| F | SO₂Me | H | Me |
| F | SO₂Me | H | Et |
| F | SO₂CF₃ | H | Me |
| F | SO₂CF₃ | H | Et |
| F | Cl | H | Me |
| F | Cl | H | Et |
| OEt | SO₂Me | H | Me |
| OEt | SO₂Me | H | Et |
| OEt | SO₂CF₃ | H | Me |
| OEt | SO₂CF₃ | H | Et |
| OEt | Cl | H | Me |
| OEt | Cl | H | Et |
| OPr-i | SO₂Me | H | Me |
| OPr-i | SO₂Me | H | Et |
| OPr-i | SO₂CF₃ | H | Me |
| OPr-i | SO₂CF₃ | H | Et |

TABLE 6-continued

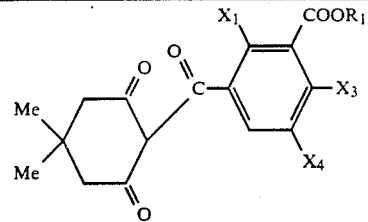

| X₁ | X₃ | X₄ | R₁ |
|---|---|---|---|
| OPr-i | Cl | H | Me |
| OPr-i | Cl | H | Et |
| OCHF₂ | SO₂Me | H | Me |
| OCHF₂ | SO₂Me | H | Et |
| OCHF₂ | SO₂CF₃ | H | Me |
| OCHF₂ | SO₂CF₃ | H | Et |
| OCHF₂ | Cl | H | Me |
| OCHF₂ | Cl | H | Et |
| OCF₃ | SO₂Me | H | Me |
| OCF₃ | SO₂Me | H | Et |
| OCF₃ | SO₂CF₃ | H | Me |
| OCF₃ | SO₂CF₃ | H | Et |
| OCF₃ | Cl | H | Me |
| OCF₃ | Cl | H | Et |
| OCH₂CF₃ | SO₂Me | H | Me |
| OCH₂CF₃ | SO₂Me | H | Et |
| OCH₂CF₃ | SO₂CF₃ | H | Me |
| OCH₂CF₃ | SO₂CF₃ | H | Et |
| OCH₂CF₃ | Cl | H | Me |
| OCH₂CF₃ | Cl | H | Et |
| CH₂OEt | SO₂Me | H | Me |
| CH₂OEt | SO₂Me | H | Et |
| CH₂OEt | SO₂CF₃ | H | Me |
| CH₂OEt | SO₂CF₃ | H | Et |
| CH₂OEt | Cl | H | Me |
| CH₂OEt | Cl | H | Et |
| CH₂SMe | SO₂Me | H | Me |
| CH₂SMe | SO₂Me | H | Et |
| CH₂SMe | SO₂CF₃ | H | Me |
| CH₂SMe | SO₂CF₃ | H | Et |
| CH₂SMe | Cl | H | Me |
| CH₂SMe | Cl | H | Et |

TABLE 7

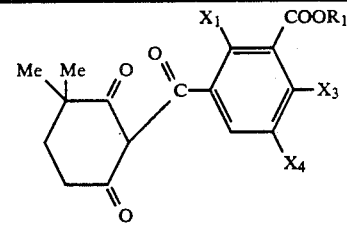

| X₁ | X₃ | X₄ | R₁ |
|---|---|---|---|
| Cl | SO₂Me | H | H |
| Cl | SO₂Me | H | Me |
| Cl | SO₂Me | H | Et |
| Cl | SO₂Me | H | Pr-i |
| Cl | SO₂Me | H | Pr-n |
| Cl | SO₂Me | H | Bu-t |
| Cl | SO₂Me | H | CH₂C≡CH |
| Cl | SO₂Me | H | CH₂C=CH₂ |
| Cl | SO₂Me | H | CH₂CH₂OMe |
| Cl | SO₂Me | H | CH₂CH₂Cl |
| Cl | SO₂Me | H | CH₂CF₃ |
| Cl | SO₂Me | H | CH₂CH₂CN |
| Cl | SO₂Me | F | Me |
| Cl | SO₂Me | F | Et |
| Cl | SO₂Me | F | Pr-i |
| Cl | SO₂Me | Cl | Me |
| Cl | SO₂Me | Cl | Et |
| Cl | SO₂Me | Cl | Pr-i |
| Cl | SO₂Me | Me | Me |
| Cl | SO₂Me | Me | Et |

TABLE 7-continued

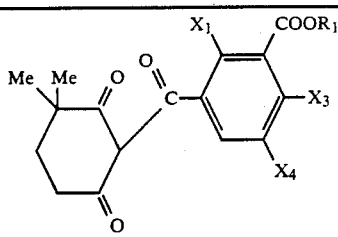

| X₁ | X₃ | X₄ | R₁ |
|---|---|---|---|
| Cl | SO₂Me | OMe | Me |
| Cl | SO₂Me | OMe | Et |
| Cl | SO₂Me | OMe | Pr-i |
| Cl | SOMe | H | Me |
| Cl | SOMe | H | Et |
| Cl | SOMe | H | Pr-i |
| Cl | SMe | H | Me |
| Cl | SMe | H | Et |
| Cl | SMe | H | Pr-i |
| Cl | SO₂CF₃ | H | Me |
| Cl | SO₂CF₃ | H | Et |
| Cl | SO₂CF₃ | H | Pr-i |
| Cl | SO₂CF₃ | H | Pr-n |
| Cl | SOCF₃ | H | Me |
| Cl | SOCF₃ | H | Et |
| Cl | SOCF₃ | H | Pr-i |
| Cl | SCF₃ | H | Me |
| Cl | SCF₃ | H | Et |
| Cl | SCF₃ | H | Pr-i |
| Cl | Cl | H | Me |
| Cl | Cl | H | Et |
| Cl | Cl | H | Pr-i |
| Cl | Cl | H | Pr-n |
| Cl | Br | H | Me |
| Cl | Br | H | Et |
| Cl | Br | H | Pr-i |
| Cl | NO₂ | H | Me |
| Cl | NO₂ | H | Et |
| Cl | NO₂ | H | Pr-i |
| Cl | CF₃ | H | Me |
| Cl | CF₃ | H | Et |
| Cl | CF₃ | H | Pr-i |
| Cl | CN | H | Me |
| Cl | CN | H | Et |
| Cl | OMe | H | Me |
| Cl | OMe | H | Et |
| OMe | SO₂Me | H | H |
| OMe | SO₂Me | H | Me |
| OMe | SO₂Me | H | Et |
| OMe | SO₂Me | H | Pr-i |
| OMe | SO₂Me | H | Pr-n |
| OMe | SO₂Me | H | Bu-t |
| OMe | SO₂Me | H | CH₂C≡CH |
| OMe | SO₂Me | H | CH₂C=CH₂ |
| OMe | SO₂Me | H | CH₂CH₂OMe |
| OMe | SO₂Me | H | CH₂CH₂Cl |
| OMe | SO₂Me | H | CH₂CF₃ |
| OMe | SO₂Me | H | CH₂CH₂CN |
| OMe | SO₂Me | F | Me |
| OMe | SO₂Me | F | Et |
| OMe | SO₂Me | F | Pr-i |
| OMe | SO₂Me | F | Pr-n |
| OMe | SO₂Me | Cl | Me |
| OMe | SO₂Me | Cl | Et |
| OMe | SO₂Me | Cl | Pr-i |
| OMe | SO₂Me | Cl | Pr-n |
| OMe | SO₂Me | Me | Me |
| OMe | SO₂Me | Me | Et |
| OMe | SO₂Me | Me | Pr-i |
| OMe | SO₂Me | Me | Pr-n |
| OMe | SO₂Me | OMe | Me |
| OMe | SO₂Me | OMe | Et |
| OMe | SO₂Me | OMe | Pr-i |
| OMe | SO₂Me | OMe | Pr-n |
| OMe | SOMe | H | Me |
| OMe | SOMe | H | Et |
| OMe | SOMe | H | Pr-i |
| OMe | SMe | H | Me |
| OMe | SMe | H | Et |

TABLE 7-continued

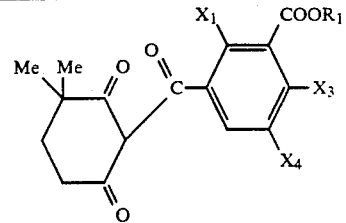

| X₁ | X₃ | X₄ | R₁ |
|---|---|---|---|
| OMe | SMe | H | Pr-i |
| OMe | SO₂CF₃ | H | Me |
| OMe | SO₂CF₃ | H | Et |
| OMe | SO₂CF₃ | H | Pr-i |
| OMe | SO₂CF₃ | H | Pr-n |
| OMe | SOCF₃ | H | Me |
| OMe | SOCF₃ | H | Et |
| OMe | SOCF₃ | H | Pr-i |
| OMe | SCF₃ | H | Me |
| OMe | SCF₃ | H | Et |
| OMe | SCF₃ | H | Pr-i |
| OMe | Cl | H | Me |
| OMe | Cl | H | Et |
| OMe | Cl | H | Pr-i |
| OMe | Cl | H | Pr-n |
| OMe | Br | H | Me |
| OMe | Br | H | Et |
| OMe | Br | H | Pr-i |
| OMe | NO₂ | H | Me |
| OMe | NO₂ | H | Et |
| OMe | NO₂ | H | Pr-i |
| OMe | CF₃ | H | Me |
| OMe | CF₃ | H | Et |
| OMe | CF₃ | H | Pr-i |
| OMe | CN | H | Me |
| OMe | CN | H | Et |
| OMe | OMe | H | Me |
| OMe | OMe | H | Et |
| Br | SO₂Me | H | Me |
| Br | SO₂Me | H | Et |
| Br | SO₂Me | H | Pr-i |
| Br | SO₂Me | H | Pr-n |
| Br | SOMe | H | Me |
| Br | SOMe | H | Et |
| Br | SMe | H | Me |
| Br | SMe | H | Et |
| Br | SO₂CF₃ | H | Me |
| Br | SO₂CF₃ | H | Et |
| Br | SOCF₃ | H | Me |
| Br | SOCF₃ | H | Et |
| Br | SCF₃ | H | Me |
| Br | SCF₃ | H | Et |
| Br | Cl | H | Me |
| Br | Cl | H | Et |
| Br | Cl | H | Pr-i |
| Br | Cl | H | Pr-n |
| Br | Br | H | Me |
| Br | Br | H | Et |
| Br | NO₂ | H | Me |
| Br | NO₂ | H | Et |
| Br | CF₃ | H | Me |
| Br | CF₃ | H | Et |
| I | SO₂Me | H | Me |
| I | SO₂Me | H | Et |
| I | SO₂Me | H | Pr-i |
| I | SO₂Me | H | Pr-n |
| I | SO₂Me | H | Bu-t |
| I | SOMe | H | Me |
| I | SOMe | H | Et |
| I | SMe | H | Me |
| I | SMe | H | Et |
| I | SO₂CF₃ | H | Me |
| I | SO₂CF₃ | H | Et |
| I | SOCF₃ | H | Me |
| I | SOCF₃ | H | Et |
| I | SCF₃ | H | Me |
| I | SCF₃ | H | Et |
| I | Cl | H | Me |
| I | Cl | H | Et |

TABLE 7-continued

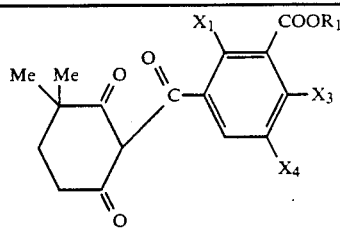

| X1 | X3 | X4 | R1 |
|---|---|---|---|
| I | Cl | H | Pr-i |
| I | Cl | H | Pr-n |
| I | Br | H | Me |
| I | Br | H | Et |
| I | NO2 | H | Me |
| I | NO2 | H | Et |
| I | CF3 | H | Me |
| I | CF3 | H | Et |
| CH2OMe | SO2Me | H | Me |
| CH2OMe | SO2Me | H | Et |
| CH2OMe | SO2Me | H | Pr-i |
| CH2OMe | SO2Me | H | Pr-n |
| CH2OMe | SO2Me | H | Bu-t |
| CH2OMe | SOMe | H | Me |
| CH2OMe | SOMe | H | Et |
| CH2OMe | SMe | H | Me |
| CH2OMe | SMe | H | Et |
| CH2OMe | SO2CF3 | H | Me |
| CH2OMe | SO2CF3 | H | Et |
| CH2OMe | SOCF3 | H | Me |
| CH2OMe | SOCF3 | H | Et |
| CH2OMe | SCF3 | H | Me |
| CH2OMe | SCF3 | H | Et |
| CH2OMe | Cl | H | Me |
| CH2OMe | Cl | H | Et |
| CH2OMe | Cl | H | Pr-i |
| CH2OMe | Cl | H | Pr-n |
| CH2OMe | Br | H | Me |
| CH2OMe | Br | H | Et |
| CH2OMe | NO2 | H | Me |
| CH2OMe | NO2 | H | Et |
| CH2OMe | CF3 | H | Me |
| CH2OMe | CF3 | H | Et |
| F | SO2Me | H | Me |
| F | SO2Me | H | Et |
| F | SO2CF3 | H | Me |
| F | SO2CF3 | H | Et |
| F | Cl | H | Me |
| F | Cl | H | Et |
| OEt | SO2Me | H | Me |
| OEt | SO2Me | H | Et |
| OEt | SO2CF3 | H | Me |
| OEt | SO2CF3 | H | Et |
| OEt | Cl | H | Me |
| OEt | Cl | H | Et |
| OPr-i | SO2Me | H | Me |
| OPr-i | SO2Me | H | Et |
| OPr-i | SO2CF3 | H | Me |
| OPr-i | SO2CF3 | H | Et |
| OPr-i | Cl | H | Me |
| OPr-i | Cl | H | Et |
| OCHF2 | SO2Me | H | Me |
| OCHF2 | SO2Me | H | Et |
| OCHF2 | SO2CF3 | H | Me |
| OCHF2 | SO2CF3 | H | Et |
| OCHF2 | Cl | H | Me |
| OCHF2 | Cl | H | Et |
| OCF3 | SO2Me | H | Me |
| OCF3 | SO2Me | H | Et |
| OCF3 | SO2CF3 | H | Me |
| OCF3 | SO2CF3 | H | Et |
| OCF3 | Cl | H | Me |
| OCF3 | Cl | H | Et |
| OCH2CF3 | SO2Me | H | Me |
| OCH2CF3 | SO2Me | H | Et |
| OCH2CF3 | SO2CF3 | H | Me |
| OCH2CF3 | SO2CF3 | H | Et |
| OCH2CF3 | Cl | H | Me |
| OCH2CF3 | Cl | H | Et |

TABLE 7-continued

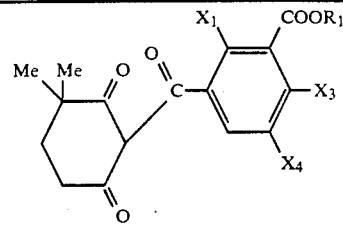

| X1 | X3 | X4 | R1 |
|---|---|---|---|
| CH2OEt | SO2Me | H | Me |
| CH2OEt | SO2Me | H | Et |
| CH2OEt | SO2CF3 | H | Me |
| CH2OEt | SO2CF3 | H | Et |
| CH2OEt | Cl | H | Me |
| CH2OEt | Cl | H | Et |
| CH2SMe | SO2Me | H | Me |
| CH2SMe | SO2Me | H | Et |
| CH2SMe | SO2CF3 | H | Me |
| CH2SMe | SO2CF3 | H | Et |
| CH2SMe | Cl | H | Me |
| CH2SMe | Cl | H | Et |

TABLE 8

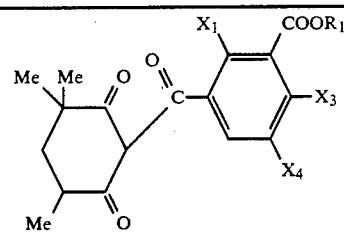

| X1 | X3 | X4 | R1 |
|---|---|---|---|
| Cl | SO2Me | H | H |
| Cl | SO2Me | H | Me |
| Cl | SO2Me | H | Et |
| Cl | SO2Me | H | Pr-i |
| Cl | SO2Me | H | Pr-n |
| Cl | SO2Me | H | Bu-t |
| Cl | SO2Me | H | CH2C≡CH |
| Cl | SO2Me | H | CH2C=CH2 |
| Cl | SO2Me | H | CH2CH2OMe |
| Cl | SO2Me | H | CH2CH2Cl |
| Cl | SO2Me | H | CH2CF3 |
| Cl | SO2Me | H | CH2CH2CN |
| Cl | SO2Me | F | Me |
| Cl | SO2Me | F | Et |
| Cl | SO2Me | F | Pr-i |
| Cl | SO2Me | Cl | Me |
| Cl | SO2Me | Cl | Et |
| Cl | SO2Me | Cl | Pr-i |
| Cl | SO2Me | Me | Me |
| Cl | SO2Me | Me | Et |
| Cl | SO2Me | OMe | Me |
| Cl | SO2Me | OMe | Et |
| Cl | SO2Me | OMe | Pr-i |
| Cl | SOMe | H | Me |
| Cl | SOMe | H | Et |
| Cl | SOMe | H | Pr-i |
| Cl | SMe | H | Me |
| Cl | SMe | H | Et |
| Cl | SMe | H | Pr-i |
| Cl | SO2CF3 | H | Me |
| Cl | SO2CF3 | H | Et |
| Cl | SO2CF3 | H | Pr-i |
| Cl | SO2CF3 | H | Pr-n |
| Cl | SOCF3 | H | Me |
| Cl | SOCF3 | H | Et |
| Cl | SOCF3 | H | Pr-i |
| Cl | SCF3 | H | Me |
| Cl | SCF3 | H | Et |
| Cl | SCF3 | H | Pr-i |
| Cl | Cl | H | Me |

TABLE 8-continued

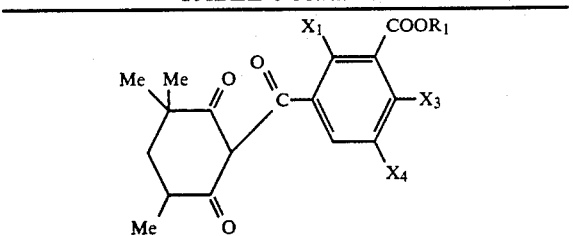
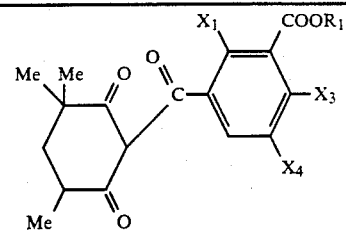

| X₁ | X₃ | X₄ | R₁ |
|---|---|---|---|
| Cl | Cl | H | Et |
| Cl | Cl | H | Pr-i |
| Cl | Cl | H | Pr-n |
| Cl | Br | H | Me |
| Cl | Br | H | Et |
| Cl | Br | H | Pr-i |
| Cl | NO₂ | H | Me |
| Cl | NO₂ | H | Et |
| Cl | NO₂ | H | Pr-i |
| Cl | CF₃ | H | Me |
| Cl | CF₃ | H | Et |
| Cl | CF₃ | H | Pr-i |
| Cl | CN | H | Me |
| Cl | CN | H | Et |
| Cl | OMe | H | Me |
| Cl | OMe | H | Et |
| OMe | SO₂Me | H | H |
| OMe | SO₂Me | H | Me |
| OMe | SO₂Me | H | Et |
| OMe | SO₂Me | H | Pr-i |
| OMe | SO₂Me | H | Pr-n |
| OMe | SO₂Me | H | Bu-t |
| OMe | SO₂Me | H | CH₂C≡CH |
| OMe | SO₂Me | H | CH₂C=CH₂ |
| OMe | SO₂Me | H | CH₂CH₂OMe |
| OMe | SO₂Me | H | CH₂CH₂Cl |
| OMe | SO₂Me | H | CH₂CF₃ |
| OMe | SO₂Me | H | CH₂CH₂CN |
| OMe | SO₂Me | F | Me |
| OMe | SO₂Me | F | Et |
| OMe | SO₂Me | F | Pr-i |
| OMe | SO₂Me | F | Pr-n |
| OMe | SO₂Me | Cl | Me |
| OMe | SO₂Me | Cl | Et |
| OMe | SO₂Me | Cl | Pr-i |
| OMe | SO₂Me | Cl | Pr-n |
| OMe | SO₂Me | Me | Me |
| OMe | SO₂Me | Me | Et |
| OMe | SO₂Me | Me | Pr-i |
| OMe | SO₂Me | Me | Pr-n |
| OMe | SO₂Me | OMe | Me |
| OMe | SO₂Me | OMe | Et |
| OMe | SO₂Me | OMe | Pr-i |
| OMe | SO₂Me | OMe | Pr-n |
| OMe | SOMe | H | Me |
| OMe | SOMe | H | Et |
| OMe | SOMe | H | Pr-i |
| OMe | SMe | H | Me |
| OMe | SMe | H | Et |
| OMe | SMe | H | Pr-i |
| OMe | SO₂CF₃ | H | Me |
| OMe | SO₂CF₃ | H | Et |
| OMe | SO₂CF₃ | H | Pr-i |
| OMe | SO₂CF₃ | H | Pr-n |
| OMe | SOCF₃ | H | Me |
| OMe | SOCF₃ | H | Et |
| OMe | SOCF₃ | H | Pr-i |
| OMe | SCF₃ | H | Me |
| OMe | SCF₃ | H | Et |
| OMe | SCF₃ | H | Pr-i |
| OMe | Cl | H | Me |
| OMe | Cl | H | Et |
| OMe | Cl | H | Pr-i |
| OMe | Cl | H | Pr-n |
| OMe | Br | H | Me |
| OMe | Br | H | Et |
| OMe | Br | H | Pr-i |
| OMe | NO₂ | H | Me |
| OMe | NO₂ | H | Et |
| OMe | NO₂ | H | Pr-i |
| OMe | CF₃ | H | Me |
| OMe | CF₃ | H | Et |
| OMe | CF₃ | H | Pr-i |
| OMe | CN | H | Me |
| OMe | CN | H | Et |
| OMe | OMe | H | Me |
| OMe | OMe | H | Et |
| Br | SO₂Me | H | Me |
| Br | SO₂Me | H | Et |
| Br | SO₂Me | H | Pr-i |
| Br | SO₂Me | H | Pr-n |
| Br | SOMe | H | Me |
| Br | SOMe | H | Et |
| Br | SMe | H | Me |
| Br | SMe | H | Et |
| Br | SO₂CF₃ | H | Me |
| Br | SO₂CF₃ | H | Et |
| Br | SOCF₃ | H | Me |
| Br | SOCF₃ | H | Et |
| Br | SCF₃ | H | Me |
| Br | SCF₃ | H | Et |
| Br | Cl | H | Me |
| Br | Cl | H | Et |
| Br | Cl | H | Pr-i |
| Br | Cl | H | Pr-n |
| Br | Br | H | Me |
| Br | Br | H | Et |
| Br | NO₂ | H | Me |
| Br | NO₂ | H | Et |
| Br | CF₃ | H | Me |
| Br | CF₃ | H | Et |
| I | SO₂Me | H | Me |
| I | SO₂Me | H | Et |
| I | SO₂Me | H | Pr-i |
| I | SO₂Me | H | Pr-n |
| I | SO₂Me | H | Bu-t |
| I | SOMe | H | Me |
| I | SOMe | H | Et |
| I | SMe | H | Me |
| I | SMe | H | Et |
| I | SO₂CF₃ | H | Me |
| I | SO₂CF₃ | H | Et |
| I | SOCF₃ | H | Me |
| I | SOCF₃ | H | Et |
| I | SCF₃ | H | Me |
| I | SCF₃ | H | Et |
| I | Cl | H | Me |
| I | Cl | H | Et |
| I | Cl | H | Pr-i |
| I | Cl | H | Pr-n |
| I | Br | H | Me |
| I | Br | H | Et |
| I | NO₂ | H | Me |
| I | NO₂ | H | Et |
| I | CF₃ | H | Me |
| I | CF₃ | H | Et |
| CH₂OMe | SO₂Me | H | Me |
| CH₂OMe | SO₂Me | H | Et |
| CH₂OMe | SO₂Me | H | Pr-i |
| CH₂OMe | SO₂Me | H | Pr-n |
| CH₂OMe | SO₂Me | H | Bu-t |
| CH₂OMe | SOMe | H | Me |
| CH₂OMe | SOMe | H | Et |
| CH₂OMe | SMe | H | Me |
| CH₂OMe | SMe | H | Et |
| CH₂OMe | SO₂CF₃ | H | Me |
| CH₂OMe | SO₂CF₃ | H | Et |
| CH₂OMe | SOCF₃ | H | Me |

TABLE 8-continued

[Structure: cyclohexane-1,3-dione with Me, Me at one position and Me at another, bearing a C(=O) group connected to a benzene ring substituted with X₁, COOR₁, X₃, X₄]

| X₁ | X₃ | X₄ | R₁ |
|---|---|---|---|
| CH₂OMe | SOCF₃ | H | Et |
| CH₂OMe | SCF₃ | H | Me |
| CH₂OMe | SCF₃ | H | Et |
| CH₂OMe | Cl | H | Me |
| CH₂OMe | Cl | H | Et |
| CH₂OMe | Cl | H | Pr-i |
| CH₂OMe | Cl | H | Pr-n |
| CH₂OMe | Br | H | Me |
| CH₂OMe | Br | H | Et |
| CH₂OMe | NO₂ | H | Me |
| CH₂OMe | NO₂ | H | Et |
| CH₂OMe | CF₃ | H | Me |
| CH₂OMe | CF₃ | H | Et |
| F | SO₂Me | H | Me |
| F | SO₂Me | H | Et |
| F | SO₂CF₃ | H | Me |
| F | SO₂CF₃ | H | Et |
| F | Cl | H | Me |
| F | Cl | H | Et |
| OEt | SO₂Me | H | Me |
| OEt | SO₂Me | H | Et |
| OEt | SO₂CF₃ | H | Me |
| OEt | SO₂CF₃ | H | Et |
| OEt | Cl | H | Me |
| OEt | Cl | H | Et |
| OPr-i | SO₂Me | H | Me |
| OPr-i | SO₂Me | H | Et |
| OPr-i | SO₂CF₃ | H | Me |
| OPr-i | SO₂CF₃ | H | Et |
| OPr-i | Cl | H | Me |
| OPr-i | Cl | H | Et |
| OCHF₂ | SO₂Me | H | Me |
| OCHF₂ | SO₂Me | H | Et |
| OCHF₂ | SO₂CF₃ | H | Me |
| OCHF₂ | SO₂CF₃ | H | Et |
| OCHF₂ | Cl | H | Me |
| OCHF₂ | Cl | H | Et |
| OCF₃ | SO₂Me | H | Me |
| OCF₃ | SO₂Me | H | Et |
| OCF₃ | SO₂CF₃ | H | Me |
| OCF₃ | SO₂CF₃ | H | Et |
| OCF₃ | Cl | H | Me |
| OCF₃ | Cl | H | Et |
| OCH₂CF₃ | SO₂Me | H | Me |
| OCH₂CF₃ | SO₂Me | H | Et |
| OCH₂CF₃ | SO₂CF₃ | H | Me |
| OCH₂CF₃ | SO₂CF₃ | H | Et |
| OCH₂CF₃ | Cl | H | Me |
| OCH₂CF₃ | Cl | H | Et |
| CH₂OEt | SO₂Me | H | Me |
| CH₂OEt | SO₂Me | H | Et |
| CH₂OEt | SO₂CF₃ | H | Me |
| CH₂OEt | SO₂CF₃ | H | Et |
| CH₂OEt | Cl | H | Me |
| CH₂OEt | Cl | H | Et |
| CH₂SMe | SO₂Me | H | Me |
| CH₂SMe | SO₂Me | H | Et |
| CH₂SMe | SO₂CF₃ | H | Me |
| CH₂SMe | SO₂CF₃ | H | Et |
| CH₂SMe | Cl | H | Me |
| CH₂SMe | Cl | H | Et |

When the compound of the present invention is to be used as an agricultural or horticultural herbicide, it is usually mixed with a suitable carrier, for instance, a solid carrier such as clay, talc, bentonite or diatomaceous earth, or a liquid carrier such as water, an alcohol (such as methanol or ethanol), an aromatic hydrocarbon (such as benzene, toluene or xylene), a chlorinated hydrocarbon, an ether, a ketone, an ester (such as ethyl acetate) or an acid amide (such as dimethylformamide). If desired, an emulsifier, a dispersing agent, a suspending agent, a penetrating agent, a spreader or a stabilizer may be added to prepare an optional formulation such as a liquid formulation, an emulsifiable concentrate, a wettable powder, a dust, a granule or a flowable.

Further, if desired, other herbicides, various insecticides, bacteriocides, plant regulating agents or synergism agents may be combined at the time of the preparation of the formulations or at the time of the application of the herbicides.

As other herbicides to be combined with the herbicide of the present invention, there may be mentioned, for instance, compounds disclosed in Farm Chemicals Handbook, the 73rd Edition (1987). Among them, there may be mentioned, for example, atrazine, cyanazine, alachlor, metolachlor, EPTC, 2,4-D, butylate, dicamba, bromoxynil and tridiphane. Further, N-[(4,6-dimethoxypyrimidin-2-yl)aminocarbonyl]-3-chloro-4-methoxycarbonyl-1-methylpyrazole-5-sulfonamide or N-[(4,6-dimethoxypyrimidin-2-yl)aminocarbonyl]-3-bromo-4-methoxycarbonyl-1-methylpyrazole-5-sulfonamide as disclosed in U.S. Pat. No. 4,668,277 may also be combined with the herbicide of the present invention.

The dose varies depending upon the application site, the season for application, the method for application, the type of the crop plant, etc. In general, however, the dose is usually within a range of from 0.001 to 10 kg per hectare as the amount of the active ingredient.

Now, Formulation Examples of the herbicides containing the compounds of the present invention as active ingredients, will be given. However, it should be understood that the present invention is by no means restricted to such specific Examples. In the following Formulation Examples, "parts" means "parts by weight".

| FORMULATION EXAMPLE 1: Wettable powder | |
|---|---|
| Compound No. 1 of the present invention | 60 parts |
| Zeeklite PFP (tradename for a kaolin-type clay, manufactured by Zeeklite Industries, Co., Ltd.) | 33 parts |
| Sorpol 5039 (tradename for a mixture of a nonionic surfactant and an anionic surfactant, manufactured by Toho Chemical Co., Ltd.) | 5 parts |
| Carplex (tradename for a coagulation-preventing agent composed of a mixture of a surfactant and fine silica powder, manufactured by Shionogi Pharmaceutical Co., Ltd.) | 2 parts |

The above ingredients are homogeneously pulverized and mixed to form a wettable powder.

| FORMULATION EXAMPLE 2: Emulsifiable concentrate | |
|---|---|
| Compound No. 1 of the present invention | 1.5 parts |
| Xylene | 78.5 parts |
| N,N-dimethylformamide | 15 parts |
| Sorpol 2680 (tradename for a mixture of a nonionic surfactant and an anionic surfactant, manufactured by Toho Chemical Co., Ltd.) | 5 parts |

The above ingredients are homogeneously mixed to obtain an emulsifiable concentrate.

| FORMULATION EXAMPLE 3: Flowable | |
| --- | --- |
| Compound No. 1 of the present invention | 40 parts |
| Agrizole B-710 (tradename for a nonionic surfactant, manufactured by Kao Corporation) | 10 parts |
| Runox 1000C (tradename for an anionic surfactant, manufactured by Toho Chemical Co., Ltd.) | 0.5 part |
| 1% Rodopol water (tradename for a thickener, manufactured by Rhone-Poulenc) | 20 parts |
| Water | 29.5 parts |

The above ingredients are homogeneously mixed to form a flowable.

| FORMULATION EXAMPLE 4: Wettable powder | |
| --- | --- |
| Compound No. 2 of the present invention | 60 parts |
| Zeeklite PFP (tradename for a kaolin-type clay, manufactured by Zeeklite Industries, Co., Ltd.) | 33 parts |
| Sorpol 5039 (tradename for a mixture of a nonionic surfactant and an anionic surfactant, manufactured by Toho Chemical Co., Ltd.) | 5 parts |
| Carplex (tradename for a coagulation-preventing agent composed of a mixture of a surfactant and fine silica powder, manufactured by Shionogi Pharmaceutical Co.., Ltd.) | 2 parts |

The above ingredients are homogeneously pulverized and mixed to form a wettable powder.

| FORMULATION EXAMPLE 5: Emulsifiable concentrate | |
| --- | --- |
| Compound No. 2 of the present invention | 1.5 parts |
| Xylene | 78.5 parts |
| N,N-dimethylformamide | 15 parts |
| Sorpol 2680 (tradename for a mixture of a nonionic surfactant and an anionic surfactant, manufactured by Toho Chemical Co., Ltd.) | 5 parts |

The above ingredients are homogeneously mixed to obtain an emulsifiable concentrate.

| FORMULATION EXAMPLE 6: Flowable | |
| --- | --- |
| Compound No. 2 of the present invention | 40 parts |
| Agrizole B-710 (tradename for a nonionic surfactant, manufactured by Kao Corporation) | 10 parts |
| Runox 1000C (tradename for an anionic surfactant, manufactured by Toho Chemical Co., Ltd.) | 0.5 part |
| 1% Rodopol water (tradename for a thickener, manufactured by Rhone-Poulenc) | 20 parts |
| Water | 29.5 parts |

The above ingredients are homogeneously mixed to form a flowable.

The compounds of the present invention are applicable not only to agricultural and horticultural fields such as upland fields, paddy fields and orchards, but also to non-agricultural fields such as athletic fields, vacant fields and railway sides for the control of various weeds. The dose in their application varies depending upon the application site, the season for application, the type of crop plants, etc. However, it is usually within a range of from 0.001 to 5 kg per hectare.

Now, the herbicidal activities of the compounds of the present invention will be described with respect to specific Test Examples.

TEST EXAMPLE 1

Test on the Herbicidal Effects in Soil Treatment

A plastic box having a length of 15 cm, a width of 22 cm and a depth of 6 cm was filled with a sterilized diluvium soil, and seeds *Echinochloa crus-galli, Eleusine indica, Digitaria adscendens, Panicum dichotomiflorum, Abutilon theophrasti, Amaranthus lividus, Polygonum longisetum* and *Zea mays* were sown, and tubers of *Cyperus esculentus* were further planted. The soil was covered thereon in the thickness of about 1.5 cm, and then a herbicide solution was applied onto the surface of the soil uniformly so that the active ingredient is distributed at a predetermined concentration. The herbicide solution was prepared by diluting the wettable powder, the emulsifiable concentrate, the liquid formulation or the flowable as described in the foregoing Formulation Examples with water and applied onto the entire soil surface by means of a small spray. Three weeks after the application of the herbicidal solution, the herbicidal effects against each weed were determined on the basis of the following standard ratings. The results thereby obtained are shown in Table 9.

Standard Ratings

5: Growth control rate of more than 90% (almost completely withered)
4: Growth control rate of from 70 to 90%
3: Growth control rate of from 40 to 70%
2: Growth control rate of from 20 to 40%
1: Growth control rate of from 5 to 20%
0: Growth control rate of less than 5% (almost non-effective)

The above growth control rates were calculated by the following equation:

$$\text{Growth control rate }(\%) = (1 - T/N) \times 100$$

where
T: Weight of the weed grown above the soil surface of the treated area
N: Weight of the weed grown above the soil surface of the non-treated area

TEST EXAMPLE 2

Test on the Herbicidal Effects in Foliage Treatment

A plastic box having a length of 15 cm, a width of 22 cm and a depth of 6 cm was filled with a sterilized diluvium soil, and seeds of *Echinochloa crus-galli, Eleusine indica, Digitaria adscendens, Panicum dichotomiflorum, Xanthium strumarium, Abutilon theophrasti, Amaranthus lividus, Polygonum longisetum* and *Zea mays* were spot-wisely sown, and tubers of *Cyperus esculentus* were further planted. Then, the soil was covered thereon in a thickness of about 1.5 cm. When the various weeds and crops grew to the 2 or 3 leaf stage, a herbicidal solution was uniformly sprayed on the foliages so that the active ingredient is applied in a predetermined concentration.

The herbicidal solution was prepared by diluting the wettable powder, the emulsifiable concentrate, the liquid formulation or the flowable as described in the above Formulation Examples with water and applied onto the entire surface of the foliages of the weeds and the crop plants by a small spray. Two weeks after the application of the herbicide solution, the herbicidal effects against each weed were determined on the basis of the standard ratings described in Test Example 1, and the phytotoxicity against each crop plant was determined on the basis of the standard ratings in Test Example 1. The results are shown in Table 10.

In Tables 9 and 10, the following abbreviations are used:

Dose: Dose of active ingredient (g/are)
EC: *Echinochloa crus-galli* (barnyardgrass)
EL: *Eleusine indica* (goosegrass)
DI: *Digitaria adscendens* (large crabgrass)
PA: *Panicum dichotomiflorum* (fall panicum)
AB: *Abutilon theophrasti* (velvet leaf)
AM: *Amaranthus lividus* (livid amaranth)
PO: *Polygonum longisetum* (persicaria blumei gross)
XA: *Xanthium strumarium* (cocklebur)
CY: *Cyperus esculentus* (yellow nutsedge)
ZE: *Zea mays* (corn)

TABLE 9

| Compound No. | Dose | EC | EL | DI | PA | AB | AM | PO | CY | ZE |
|---|---|---|---|---|---|---|---|---|---|---|
| 1 | 0.5 | 5 | 5 | 5 | 5 | 5 | 5 | 5 | 5 | 0 |
|  | 1 | 5 | 5 | 5 | 5 | 5 | 5 | 5 | 5 | 0 |
|  | 2 | 5 | 5 | 5 | 5 | 5 | 5 | 5 | 5 | 0 |
| 2 | 0.5 | 5 | 5 | 5 | 5 | 5 | 5 | 5 | 5 | 0 |
|  | 1 | 5 | 5 | 5 | 5 | 5 | 5 | 5 | 5 | 0 |
|  | 2 | 5 | 5 | 5 | 5 | 5 | 5 | 5 | 5 | 0 |
| Reference Compound A | 4 | 3 | 3 | 3 | 1 | 4 | 5 | 5 | 0 | 0 |
|  | 8 | 4 | 4 | 4 | 2 | 5 | 5 | 5 | 0 | 0 |
|  | 16 | 5 | 5 | 5 | 3 | 5 | 5 | 5 | 1 | 1 |
| Reference Compound B | 4 | 5 | 5 | 5 | 5 | 1 | 1 | 1 | 2 | 0 |
|  | 8 | 5 | 5 | 5 | 5 | 2 | 2 | 2 | 3 | 0 |
|  | 16 | 5 | 5 | 5 | 5 | 3 | 3 | 3 | 4 | 1 |
| Reference Compound C | 0.5 | 3 | 3 | 3 | 2 | 4 | 1 | 1 | 3 | 0 |
|  | 1 | 4 | 4 | 4 | 3 | 5 | 2 | 2 | 4 | 0 |
|  | 2 | 5 | 5 | 5 | 4 | 5 | 3 | 3 | 5 | 0 |

TABLE 10

| Compound No. | Dose | EC | EL | DI | PA | AB | AM | PO | XA | CY | ZE |
|---|---|---|---|---|---|---|---|---|---|---|---|
| 1 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| 2 | 0.5 | 5 | 5 | 5 | 5 | 5 | 5 | 5 | 5 | 5 | 0 |
|  | 1 | 5 | 5 | 5 | 5 | 5 | 5 | 5 | 5 | 5 | 0 |
|  | 2 | 5 | 5 | 5 | 5 | 5 | 5 | 5 | 5 | 5 | 0 |
| Reference Compound A | 4 | 3 | 2 | 3 | 0 | 3 | 5 | 5 | 4 | 0 | 0 |
|  | 8 | 4 | 3 | 4 | 1 | 5 | 5 | 5 | 5 | 0 | 1 |
|  | 16 | 5 | 4 | 5 | 2 | 5 | 5 | 5 | 5 | 1 | 2 |
| Reference Compound B | 4 | 4 | 3 | 4 | 3 | 0 | 2 | 2 | 0 | 1 | 0 |
|  | 8 | 4 | 4 | 4 | 4 | 1 | 3 | 3 | 1 | 2 | 1 |
|  | 16 | 5 | 5 | 5 | 5 | 2 | 4 | 4 | 2 | 3 | 2 |
| Reference Compound C | 0.5 | 4 | 3 | 3 | 2 | 4 | 0 | 1 | 2 | 3 | 0 |
|  | 1 | 5 | 4 | 4 | 3 | 5 | 1 | 2 | 3 | 4 | 0 |
|  | 2 | 5 | 5 | 5 | 4 | 5 | 2 | 3 | 4 | 5 | 1 |

In Tables 9 and 10, the Comparative Compounds are as follows:

Reference Compound A: Atrazine

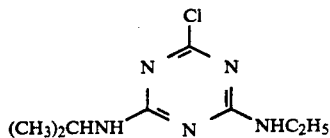

Reference Compound B: Alachlor

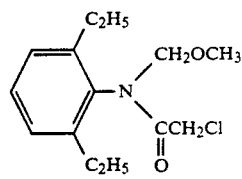

Reference Compound C

Compound disclosed in Japanese Unexamined Patent Publication No. 87238/1985

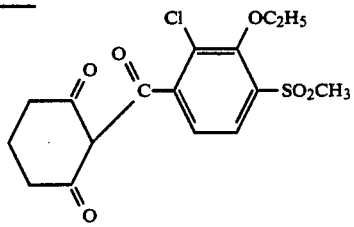

What is claimed is:
1. A substituted benzoyl derivative having the formula:

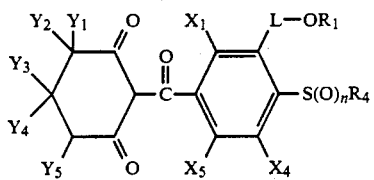

wherein:
$X_1$ is $C_1$-$C_4$ alkyl, $C_1$-$C_4$ alkoxy or halogen;
$X_4$ is hydrogen, $C_1$-$C_4$ alkyl, $C_1$-$C_4$ alkoxy or halogen;
$X_5$ is hydrogen or fluorine;
$Y_1$, $Y_2$, $Y_3$, $Y_4$ and $Y_5$ are independently hydrogen or $C_1$-$C_4$ alkyl;
$R_1$ is $C_1$-$C_4$ alkyl;
$R_4$ is $C_1$-$C_3$ is alkyl;
n is an integer of 0, 1 or 2;
L is $C_1$-$C_4$ alkylene.

2. The compound of claim 1 wherein:
$X_1$ is $C_1$-$C_4$ alkyl;
L is $C_1$-$C_4$ alkylene;
$R_1$ is $C_1$-$C_4$ alkyl;
$R_4$ is $C_1$-$C_3$ alkyl;
$X_4$ is hydrogen;
$X_5$ is hydrogen.

3. The compound of claim 2 wherein:
$X_1$ is methyl;
L is methylene;
$R_1$ is methyl;
$R_4$ is methyl.

4. A selective herbicide comprising an herbicidally effective amount of at least one substituted benzoyl derivative of claim 1 or its salt, and an agriculturally acceptable carrier.

5. A method for controlling undesirable vegetation comprising applying to the area where control is desired, an herbicidally effective amount of the compound of claim 3.

* * * * *